United States Patent
Petersheim et al.

(10) Patent No.: US 10,682,238 B2
(45) Date of Patent: Jun. 16, 2020

(54) INTERVERTEBRAL SPINAL IMPLANT

(71) Applicant: GLOBUS MEDICAL, INC., Audubon, PA (US)

(72) Inventors: Samuel Petersheim, Elverson, PA (US); Mark Miccio, Lynbrook, NY (US)

(73) Assignee: Globus Medical, Inc., Audubon, PA (US)

(*) Notice: Subject to any disclaimer, the term of this patent is extended or adjusted under 35 U.S.C. 154(b) by 0 days.

(21) Appl. No.: 16/151,737

(22) Filed: Oct. 4, 2018

(65) Prior Publication Data

US 2019/0343652 A1  Nov. 14, 2019

Related U.S. Application Data

(63) Continuation-in-part of application No. 15/973,818, filed on May 8, 2018.

(51) Int. Cl.
*A61F 2/44*     (2006.01)
*A61F 2/30*     (2006.01)

(52) U.S. Cl.
CPC ........ *A61F 2/4455* (2013.01); *A61F 2/30771* (2013.01); *A61F 2/447* (2013.01); *A61F 2/4465* (2013.01); *A61F 2002/308* (2013.01); *A61F 2002/3097* (2013.01); *A61F 2002/30593* (2013.01); *A61F 2002/30904* (2013.01); *A61F 2002/30968* (2013.01); *A61F 2002/30985* (2013.01)

(58) Field of Classification Search
CPC ................ A61F 2/4455; A61F 2/30771; A61F 2/30479; A61F 2/4465; A61F 2/447; A61F 2002/30182; A61F 2002/308; A61F 2002/30904; A61F 2002/3097; A61F 2002/30968; A61F 2002/30985; A61F 2002/4475
USPC ........................... 606/246; 623/17.11, 17.16
See application file for complete search history.

(56) References Cited

U.S. PATENT DOCUMENTS

| | | | |
|---|---|---|---|
| 4,834,757 A * | 5/1989 | Brantigan | A61B 17/1604 623/17.11 |
| 5,192,327 A * | 3/1993 | Brantigan | A61F 2/44 606/247 |
| 5,370,692 A | 12/1994 | Fink et al. | |
| 6,206,924 B1 | 3/2001 | Timm | |
| 6,520,993 B2 | 2/2003 | James et al. | |
| 6,520,996 B1 | 2/2003 | Manasas | |
| 6,802,867 B2 | 10/2004 | Manasas | |
| 7,238,203 B2 | 7/2007 | Bagga et al. | |

(Continued)

*Primary Examiner* — Pedro Philogene
*Assistant Examiner* — David C Comstock

(57) ABSTRACT

An intervertebral implant for implantation in an intervertebral space between vertebrae. The implant includes a body extending from an upper surface to a lower surface. The body has a front end, a rear end and a pair of spaced apart first and second side walls extending between the front and rear walls such that an internal chamber is defined within the front and rear ends and the first and second walls. The body defines an outer perimeter and an inner perimeter extending about the internal chamber. At least one of the side walls is defined by an integral porous structure which extends from the outer perimeter to the inner perimeter. The at least one of the side walls is free of vertical solid support structure between the upper and lower surface.

20 Claims, 49 Drawing Sheets

(56) References Cited

U.S. PATENT DOCUMENTS

| | | |
|---|---|---|
| 7,537,664 B2 | 5/2009 | O'Neill et al. |
| 7,875,075 B2 * | 1/2011 | Schwab ................ A61F 2/4465 623/17.11 |
| 7,918,891 B1 | 4/2011 | Curran et al. |
| 8,377,139 B2 | 2/2013 | Laubert et al. |
| 8,425,607 B2 | 4/2013 | Waugh et al. |
| 8,430,930 B2 | 4/2013 | Hunt |
| 8,530,560 B2 | 9/2013 | Kerr et al. |
| 8,551,173 B2 | 10/2013 | Lechmann et al. |
| D700,332 S | 2/2014 | Tyber |
| 8,728,387 B2 | 5/2014 | Jones et al. |
| 8,735,773 B2 | 5/2014 | Lang |
| 8,764,832 B2 * | 7/2014 | Schwab ................ A61F 2/4465 623/17.16 |
| 8,843,229 B2 | 9/2014 | Vanasse et al. |
| 8,992,703 B2 | 3/2015 | O'Neill et al. |
| 9,034,048 B2 | 5/2015 | Choren |
| 9,186,257 B2 | 11/2015 | Geisler et al. |
| 9,271,845 B2 | 3/2016 | Hunt et al. |
| 9,295,562 B2 | 3/2016 | Lechmann et al. |
| 9,364,896 B2 | 6/2016 | Christensen et al. |
| 9,421,108 B2 | 8/2016 | Hunt |
| 9,433,510 B2 | 9/2016 | Lechmann et al. |
| 9,456,901 B2 | 10/2016 | Jones et al. |
| 9,545,317 B2 | 1/2017 | Hunt |
| 9,549,823 B2 | 1/2017 | Hunt et al. |
| 9,572,669 B2 | 2/2017 | Hunt et al. |
| 9,636,226 B2 | 5/2017 | Hunt |
| 9,649,200 B2 | 5/2017 | Wickham |
| 9,662,157 B2 | 5/2017 | Schneider et al. |
| 9,662,226 B2 | 5/2017 | Wickham |
| D797,934 S | 9/2017 | Pimenta et al. |
| 9,757,235 B2 | 9/2017 | Hunt et al. |
| 9,775,711 B2 | 10/2017 | Li et al. |
| 9,782,270 B2 | 10/2017 | Wickham |
| 9,788,972 B2 | 10/2017 | Flickinger et al. |
| 9,801,731 B2 | 10/2017 | Sawyer et al. |
| 9,907,657 B2 | 3/2018 | Fonte et al. |
| 2004/0122518 A1 * | 6/2004 | Rhoda ................ A61F 2/44 623/17.11 |
| 2010/0228296 A1 * | 9/2010 | Vraney ................ A61F 2/447 606/279 |
| 2012/0158143 A1 | 6/2012 | Shapiro |
| 2012/0292814 A1 | 11/2012 | Spratt et al. |
| 2013/0116793 A1 * | 5/2013 | Kloss ................ A61F 2/442 623/17.16 |
| 2015/0018956 A1 | 1/2015 | Steinmann et al. |
| 2015/0045892 A1 | 2/2015 | Lynn et al. |
| 2015/0134063 A1 | 5/2015 | Steinmann et al. |
| 2016/0022431 A1 * | 1/2016 | Wickham ................ A61F 2/447 623/17.16 |
| 2016/0051371 A1 | 2/2016 | DeFelice et al. |
| 2016/0199193 A1 | 7/2016 | Willis et al. |
| 2016/0213485 A1 | 7/2016 | Shaufler et al. |
| 2016/0213486 A1 | 7/2016 | Nunley et al. |
| 2016/0213487 A1 | 7/2016 | Wilson et al. |
| 2016/0262908 A1 | 9/2016 | Arramon et al. |
| 2016/0270920 A1 | 9/2016 | Dawson et al. |
| 2016/0324656 A1 | 11/2016 | Morris et al. |
| 2017/0020685 A1 | 1/2017 | Geisler et al. |
| 2017/0042697 A1 | 2/2017 | McShane, III et al. |
| 2017/0156880 A1 | 6/2017 | Halverson et al. |
| 2017/0172758 A1 | 6/2017 | Field et al. |
| 2017/0182222 A1 | 6/2017 | Paddock et al. |
| 2017/0216035 A1 | 8/2017 | Hunt |
| 2017/0216036 A1 | 8/2017 | Cordaro |
| 2017/0239064 A1 | 8/2017 | Cordaro |
| 2017/0258606 A1 | 9/2017 | Afzal |
| 2017/0296352 A1 | 10/2017 | Richerme et al. |
| 2017/0333205 A1 | 11/2017 | Joly et al. |
| 2017/0340453 A1 | 11/2017 | Kaufmann et al. |
| 2017/0354513 A1 | 12/2017 | Maglaras et al. |
| 2017/0360563 A1 | 12/2017 | Hunt et al. |
| 2018/0014938 A1 | 1/2018 | Hagen et al. |
| 2018/0110624 A1 * | 4/2018 | Arnone ................ A61F 2/30771 |
| 2018/0256336 A1 * | 9/2018 | Mueller ................ A61F 2/30 |

* cited by examiner

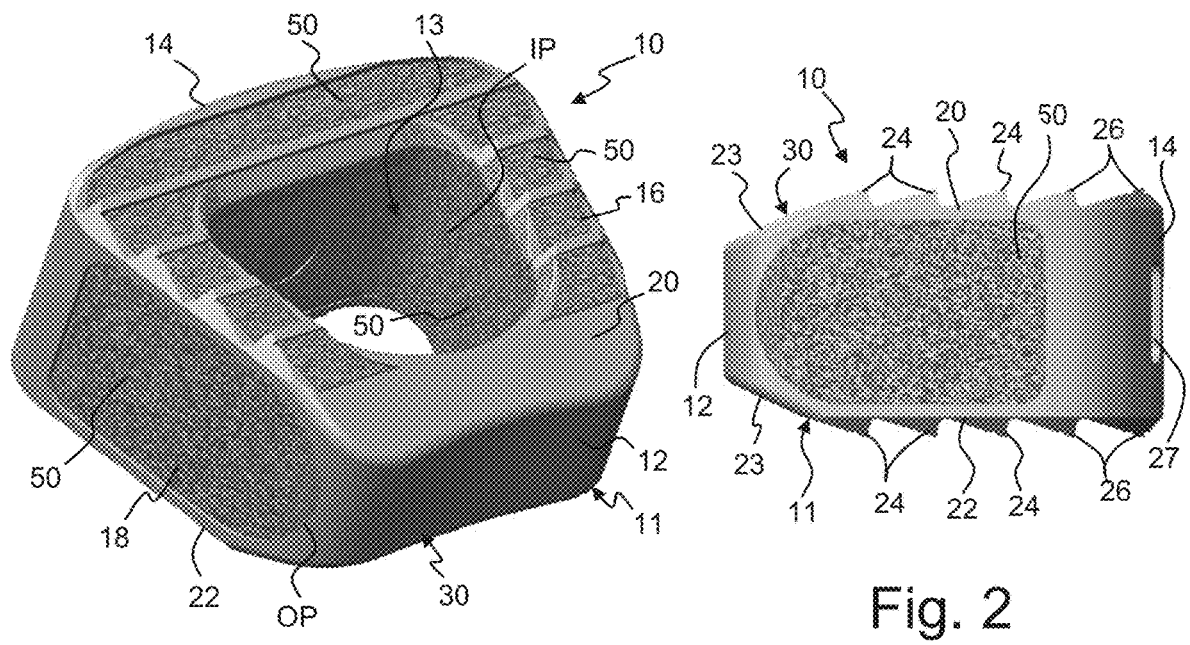
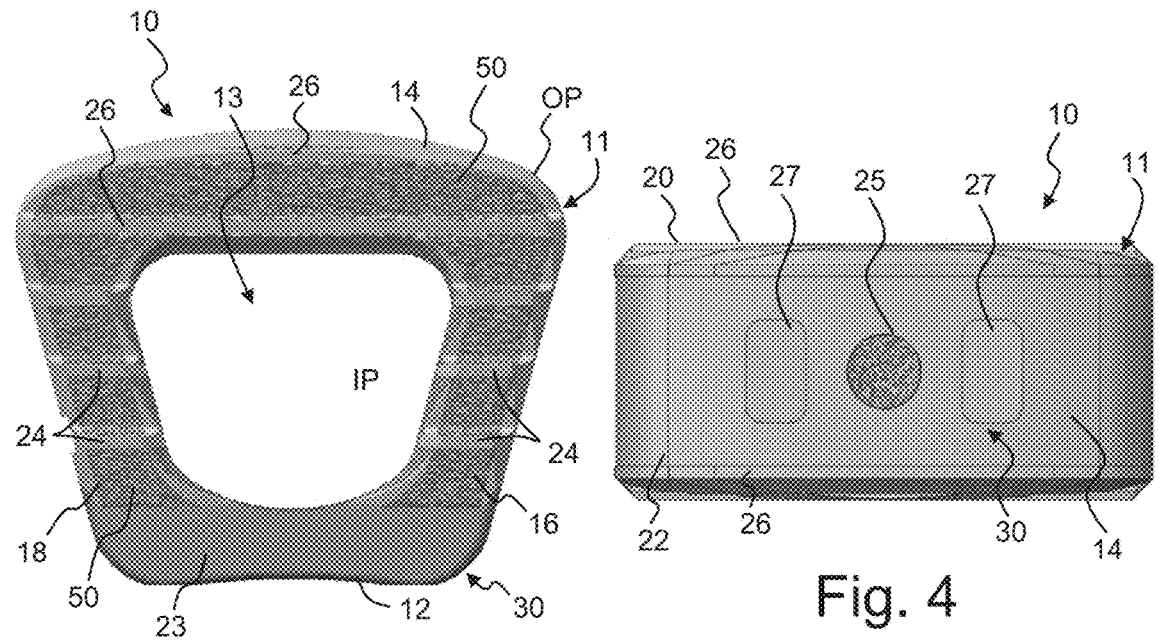

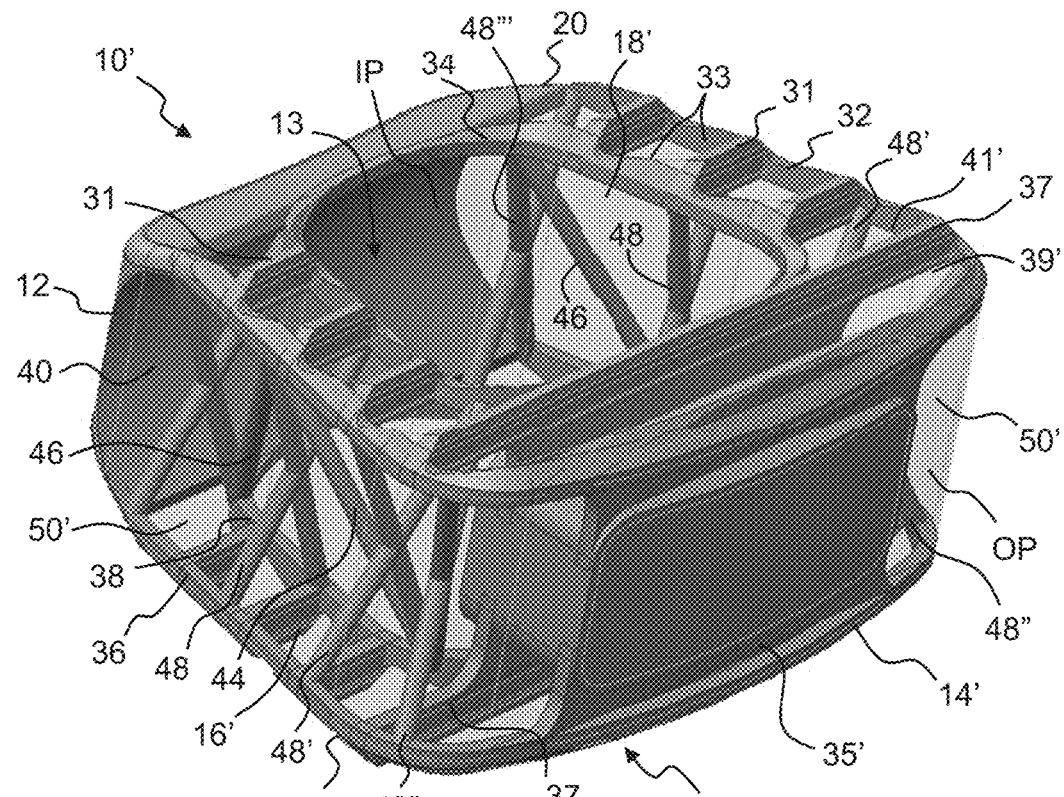
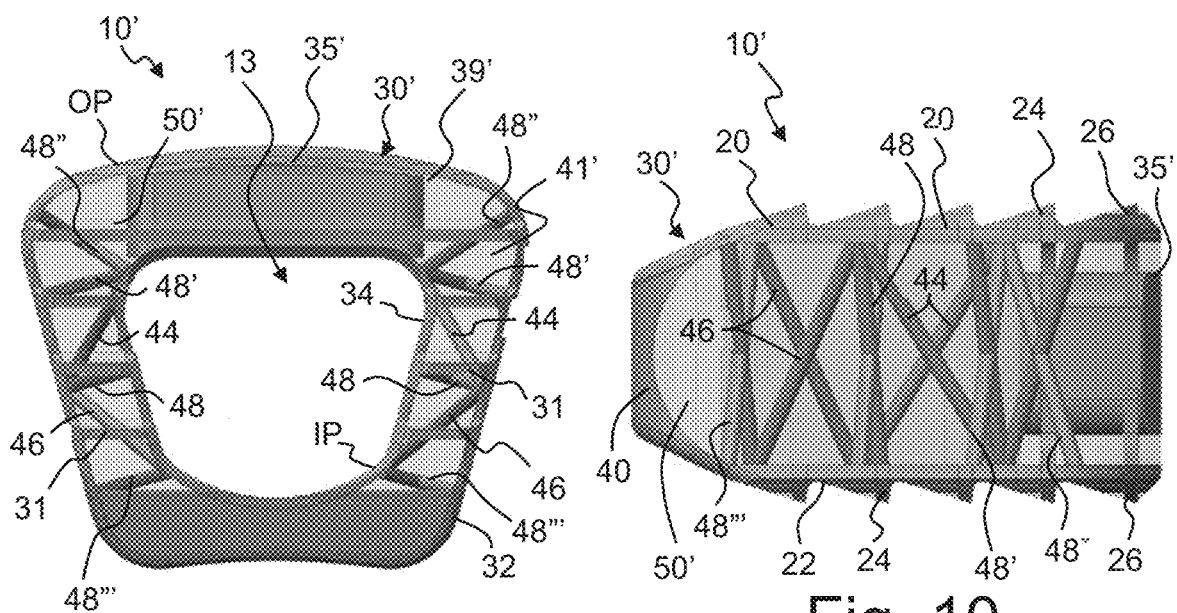

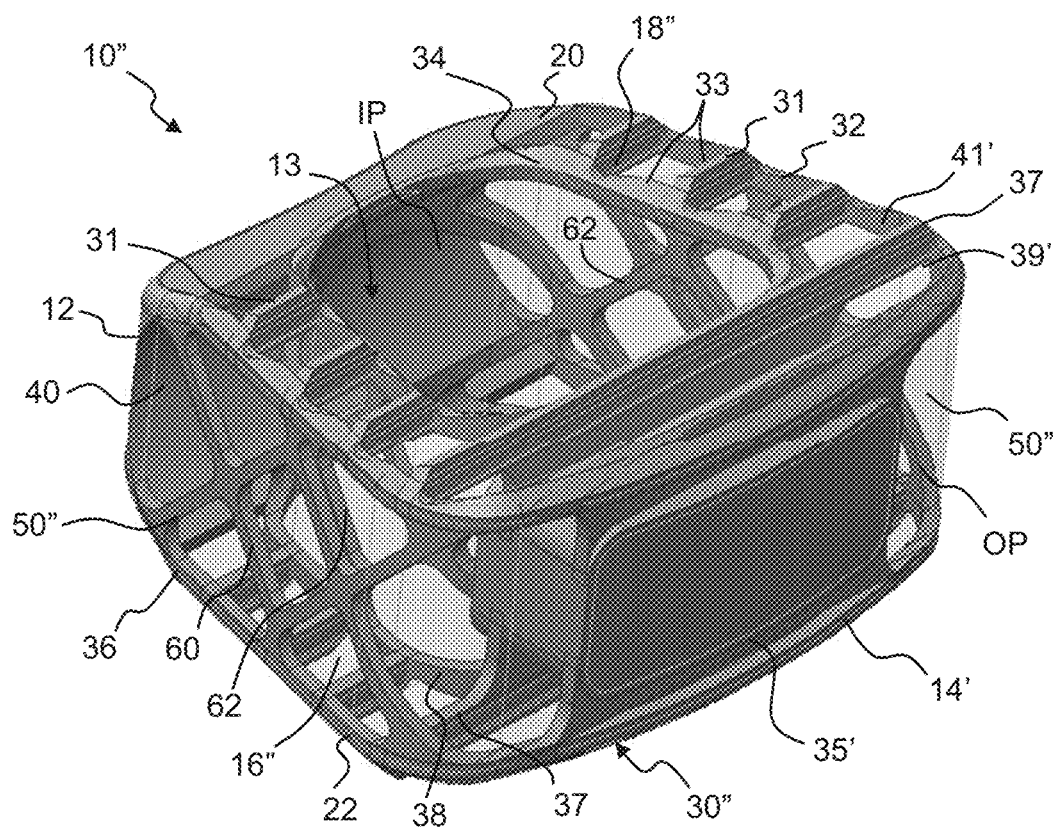
Fig. 11
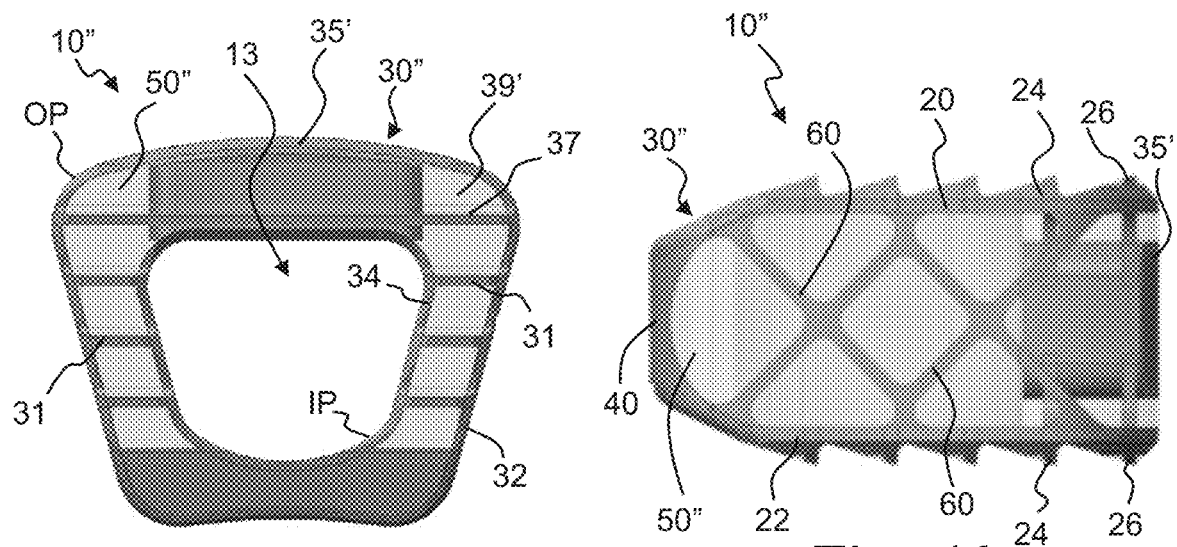
Fig. 12
Fig. 13

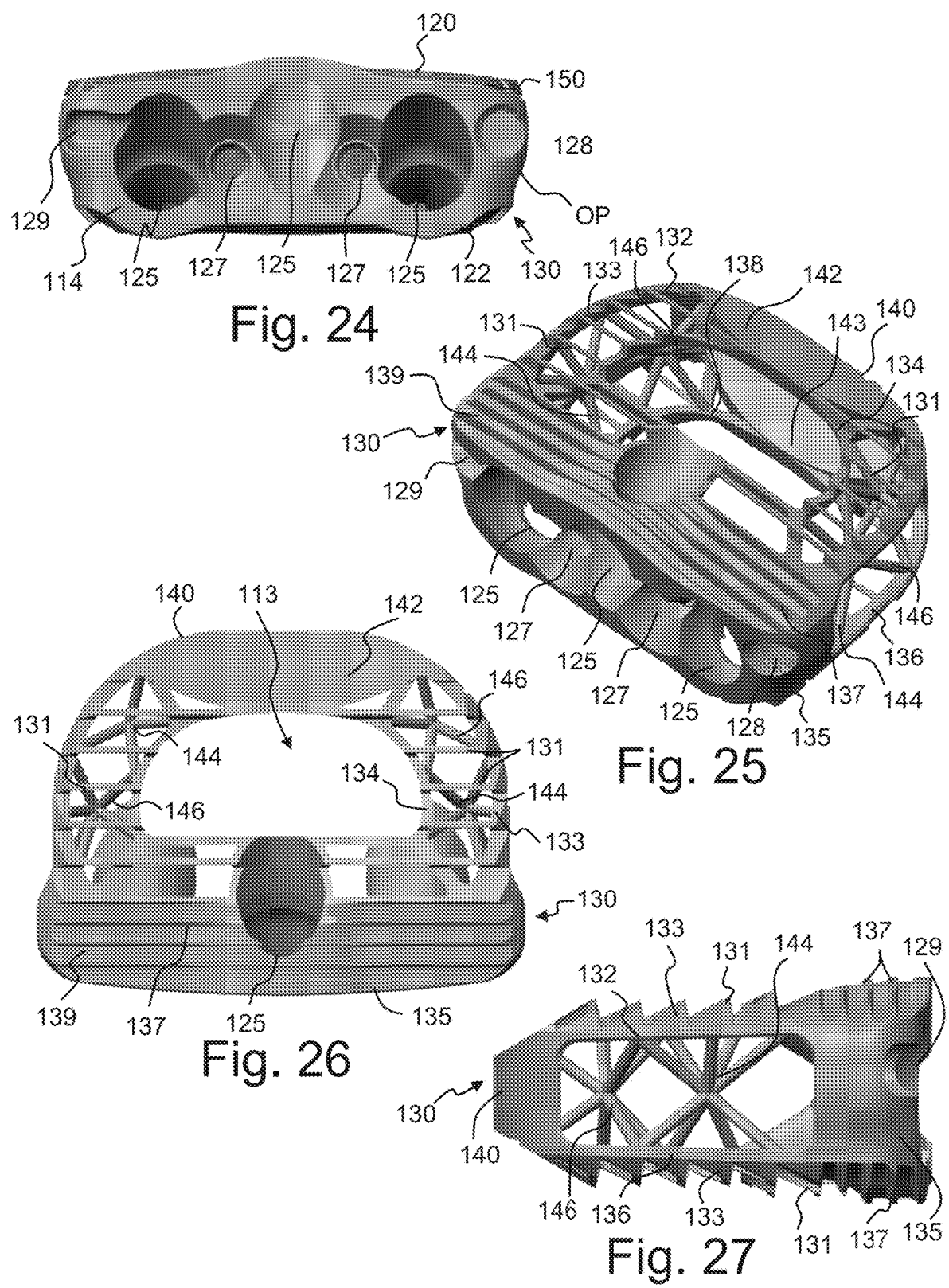

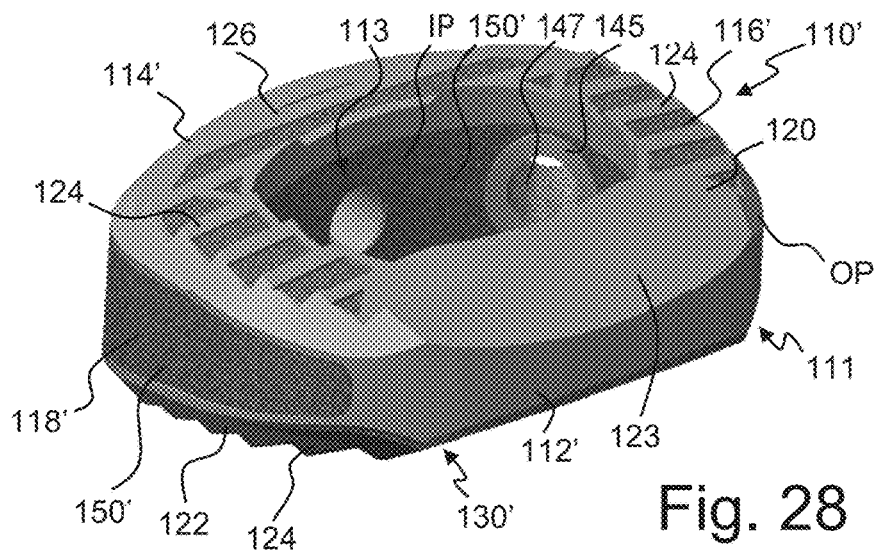
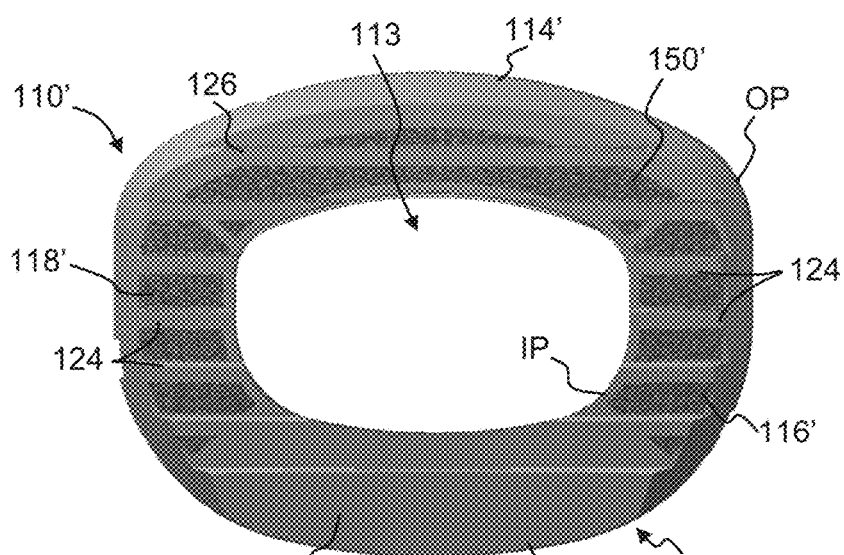
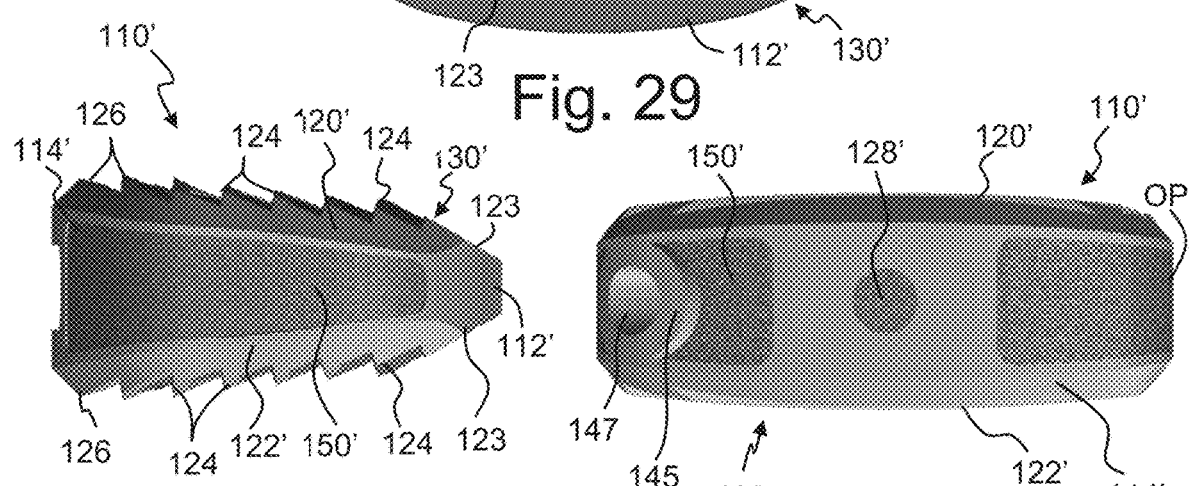

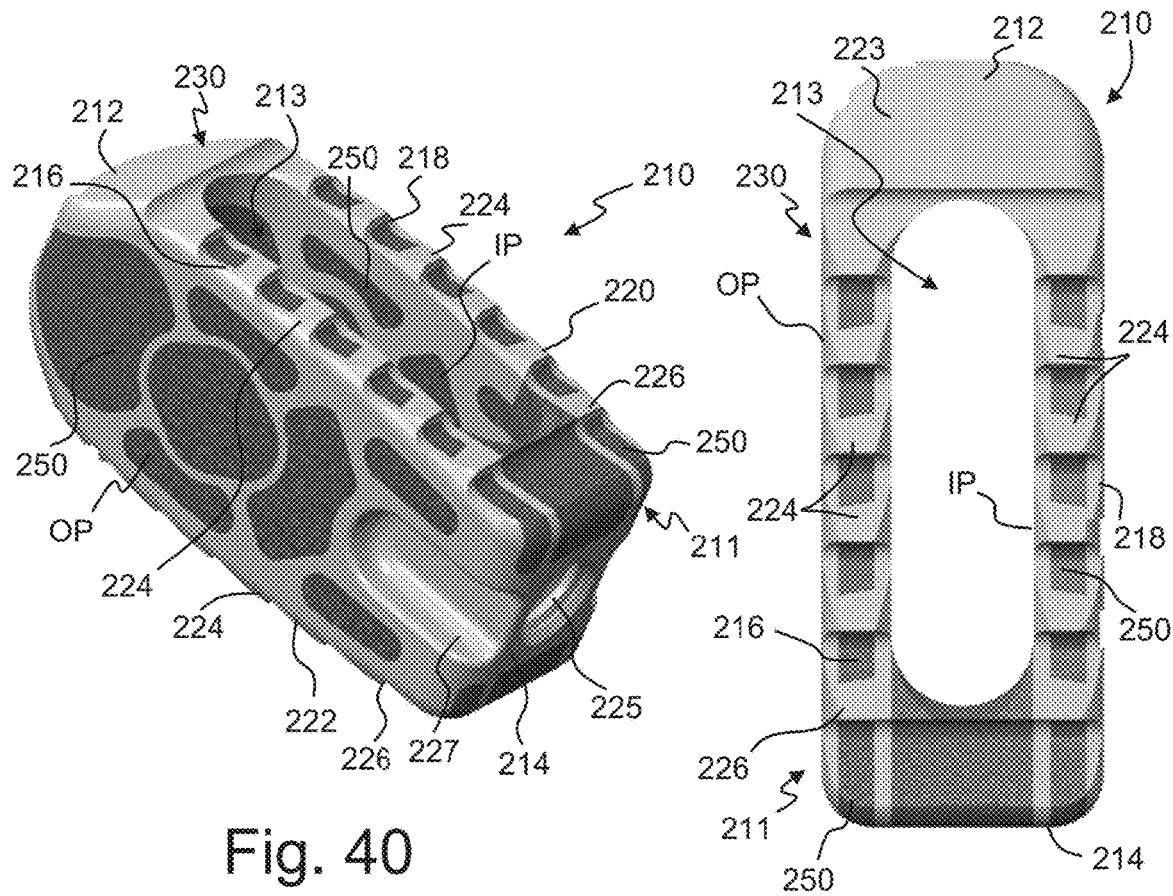
Fig. 40
Fig. 41
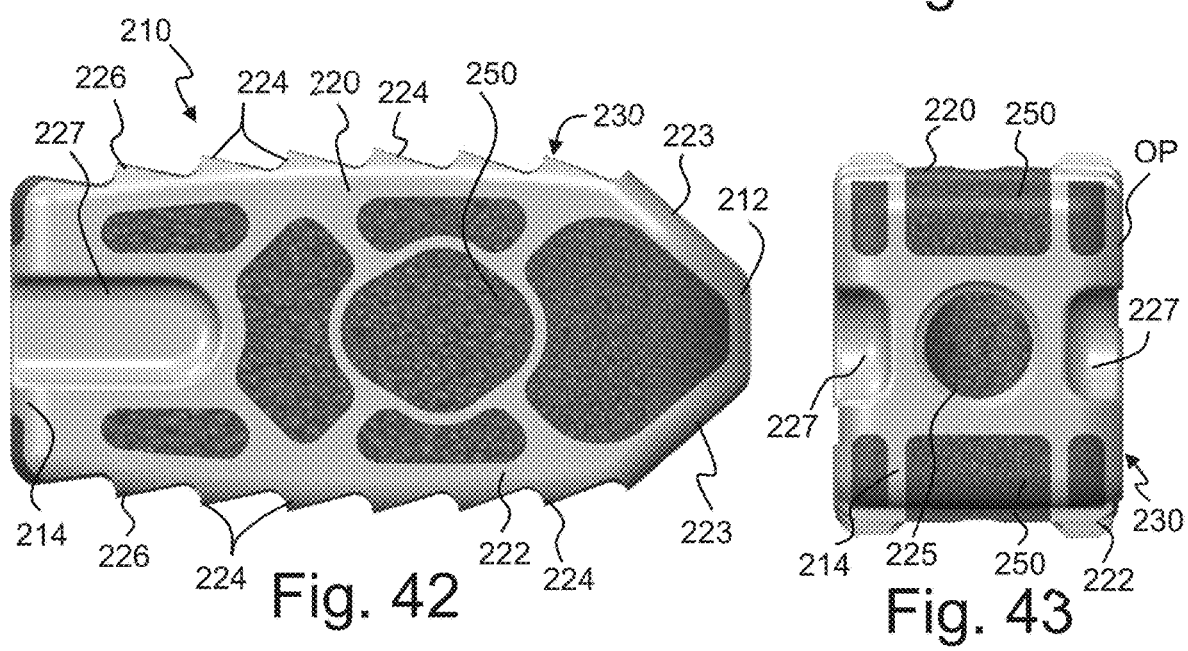
Fig. 42
Fig. 43

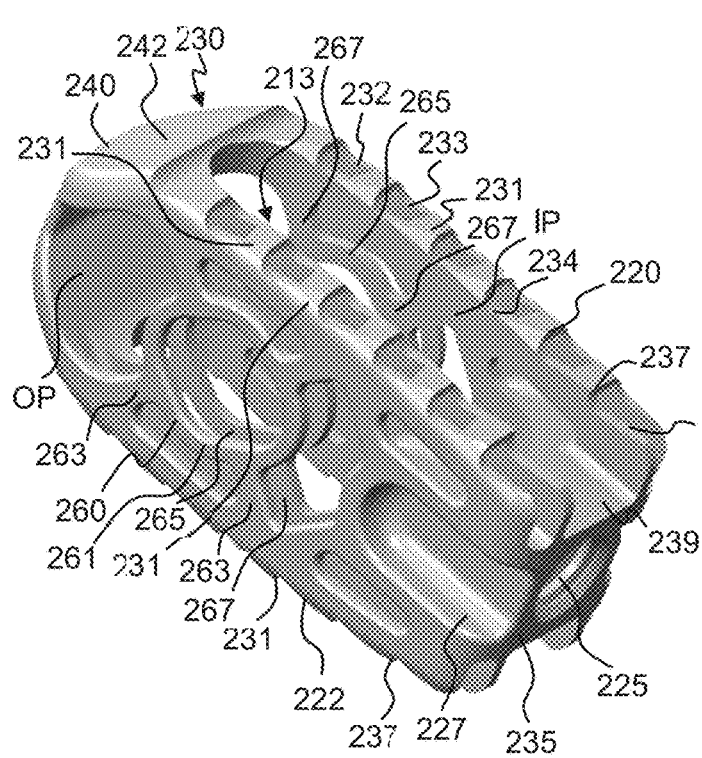
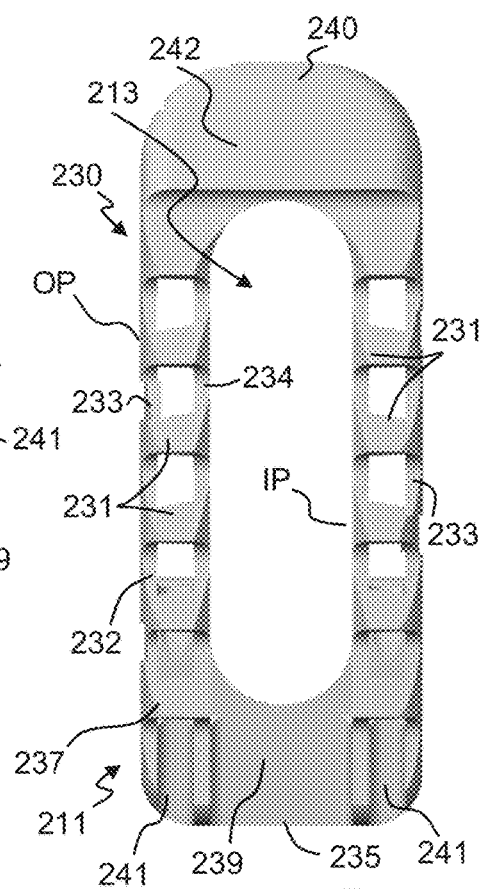
Fig. 44
Fig. 45
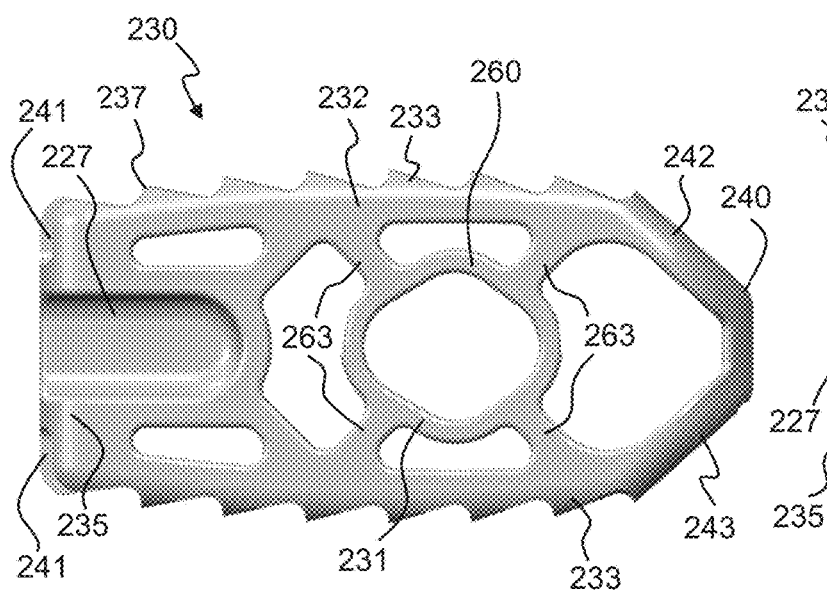
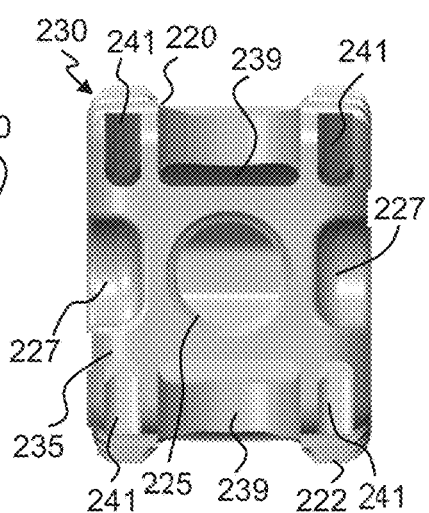
Fig. 46
Fig. 47

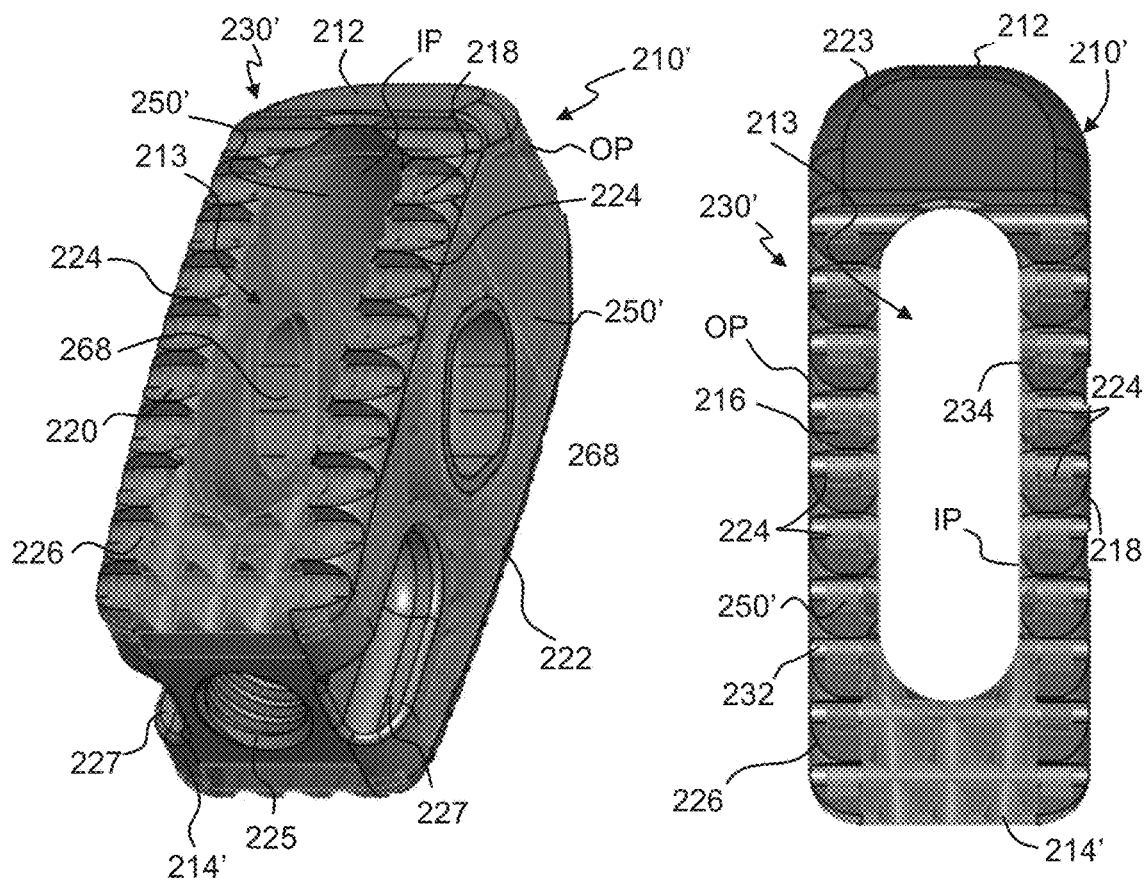
Fig. 48
Fig. 49
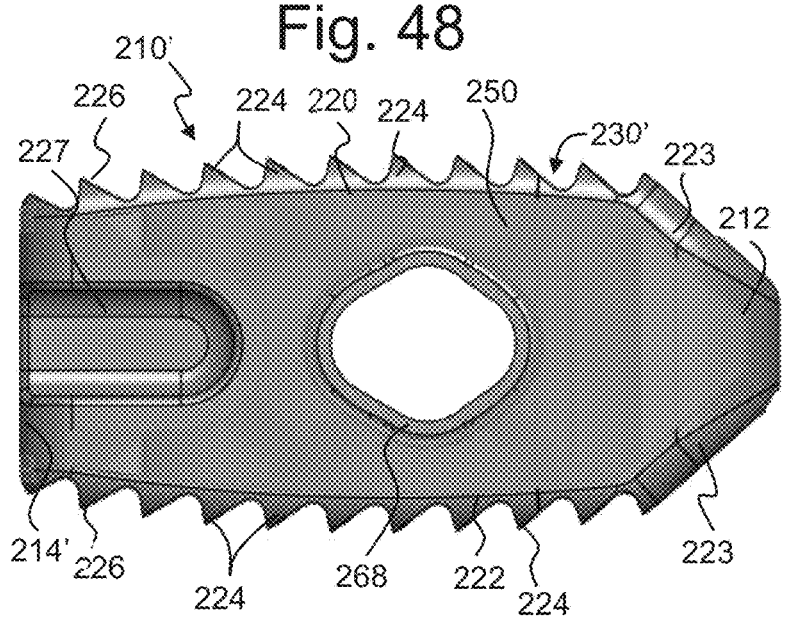
Fig. 50
Fig. 51

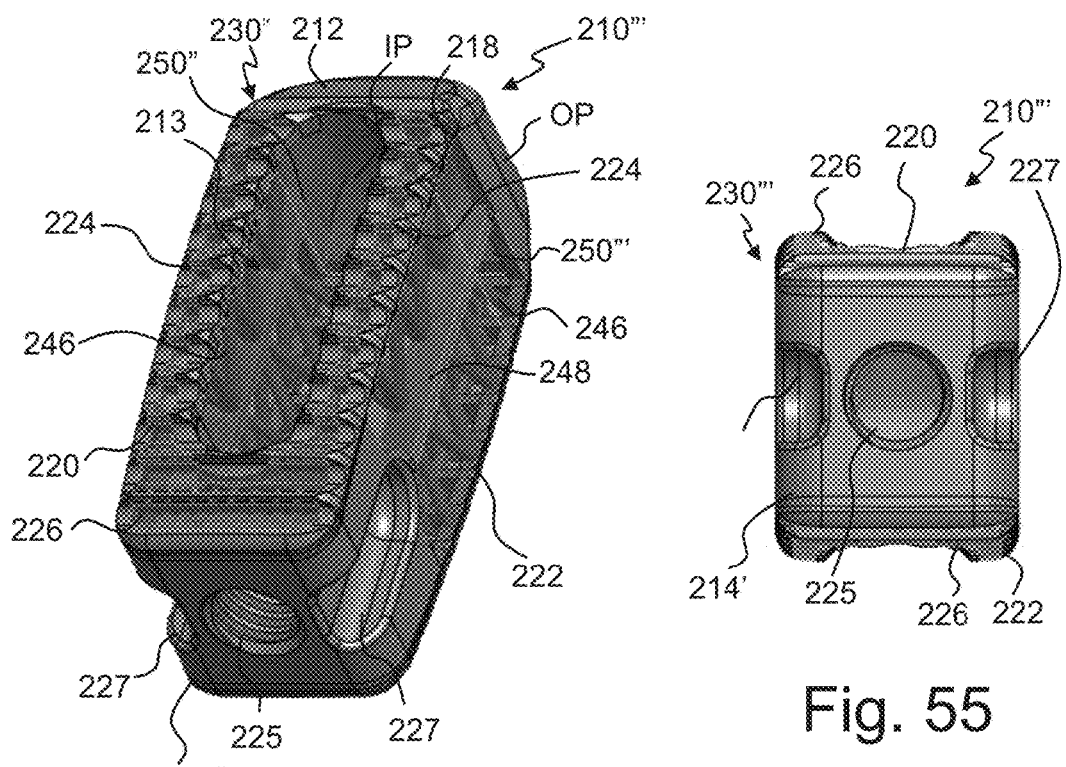
Fig. 54
Fig. 55
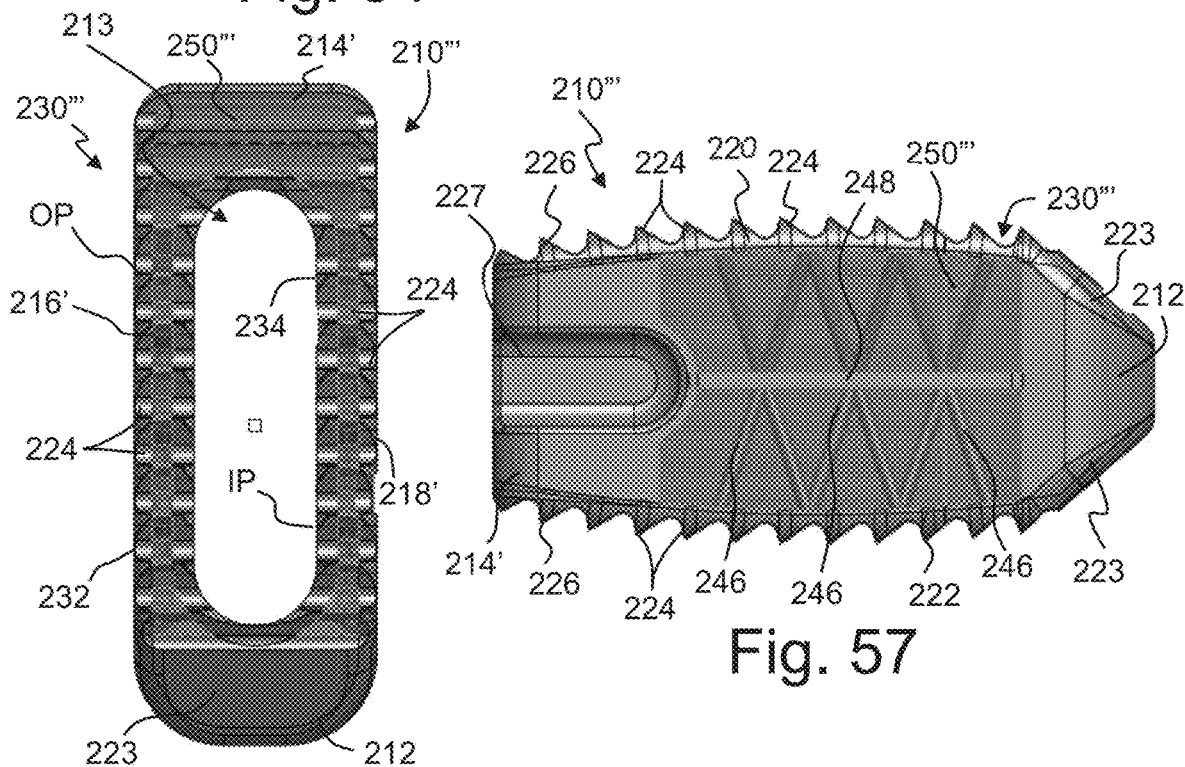
Fig. 56
Fig. 57

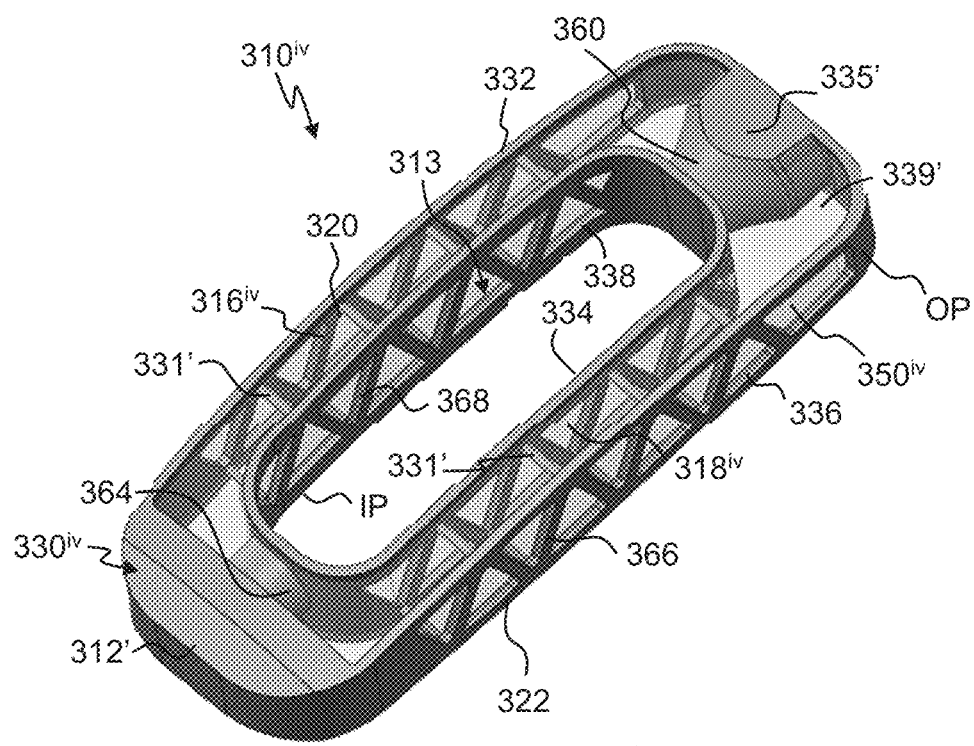
Fig. 73
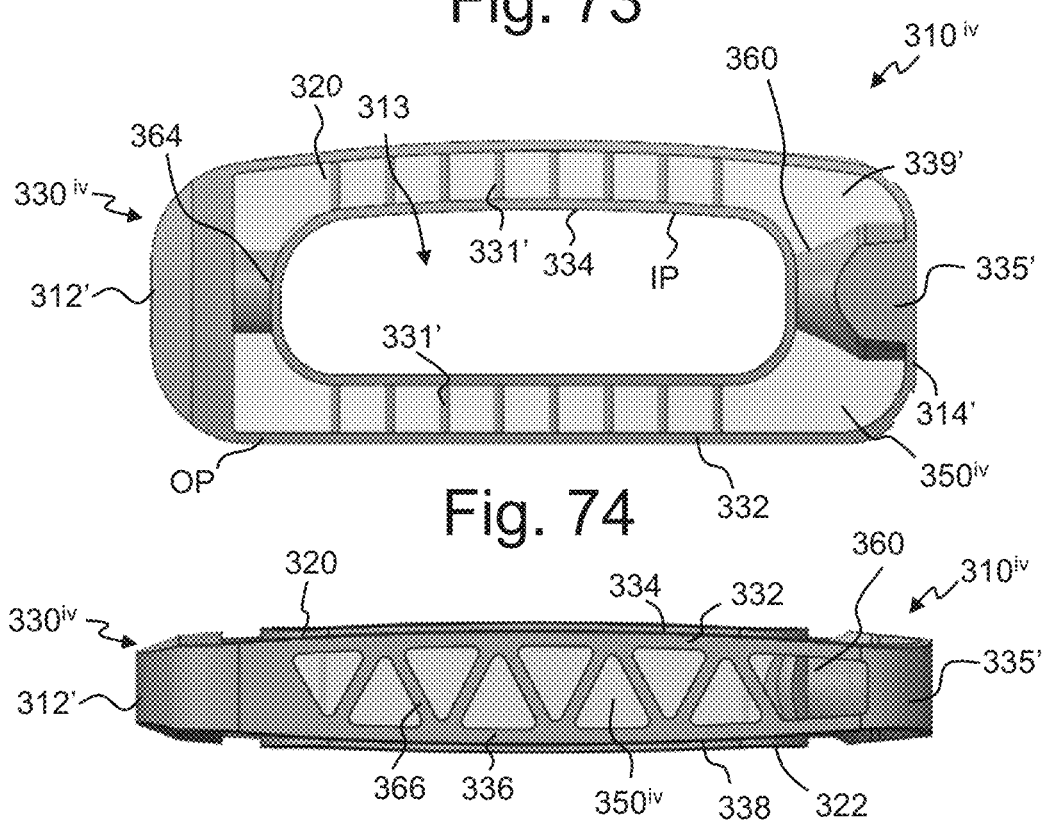
Fig. 74
Fig. 75

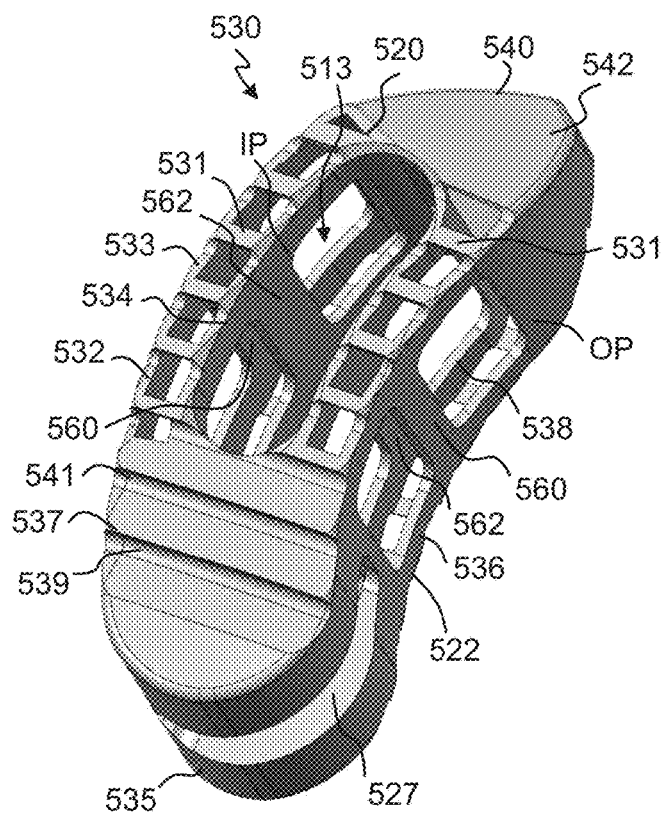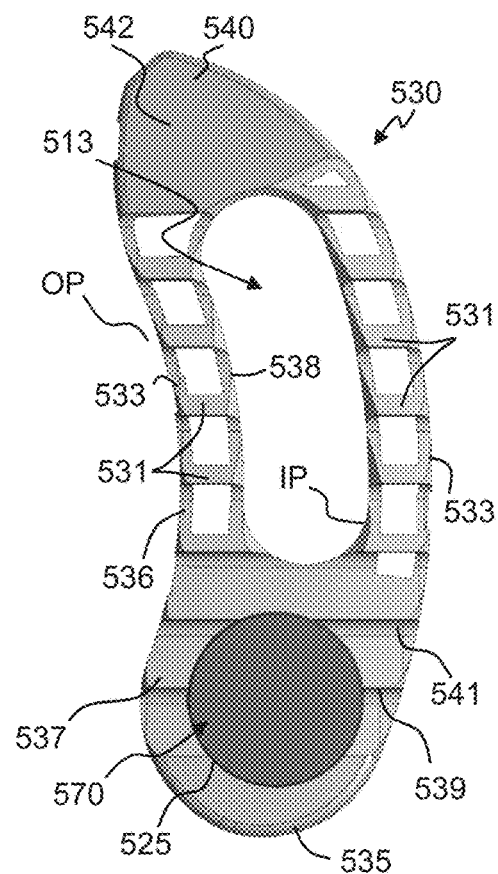
Fig. 93
Fig. 94
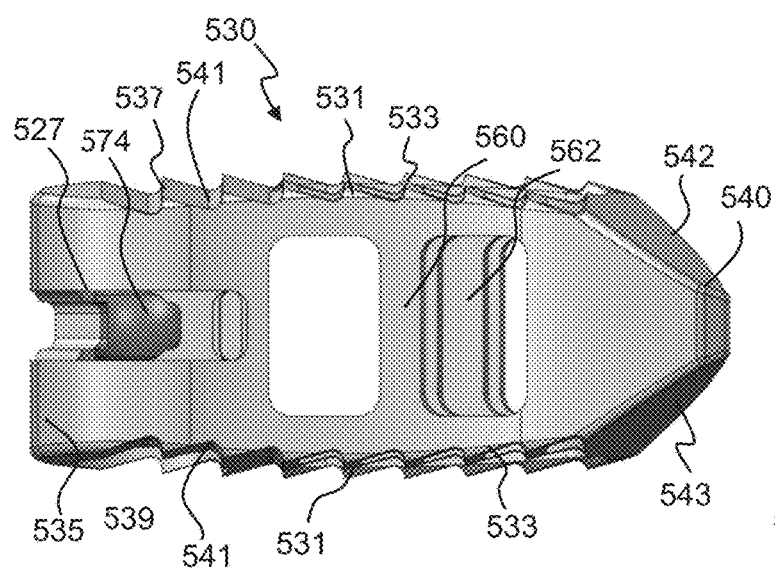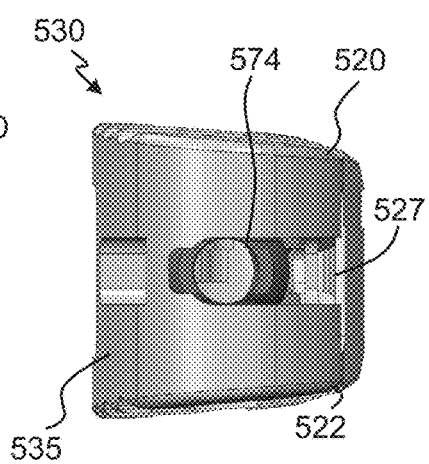
Fig. 95
Fig. 96

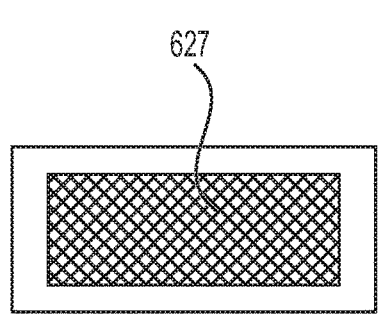
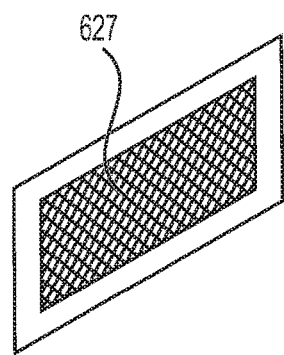
FIG. 105  FIG. 106
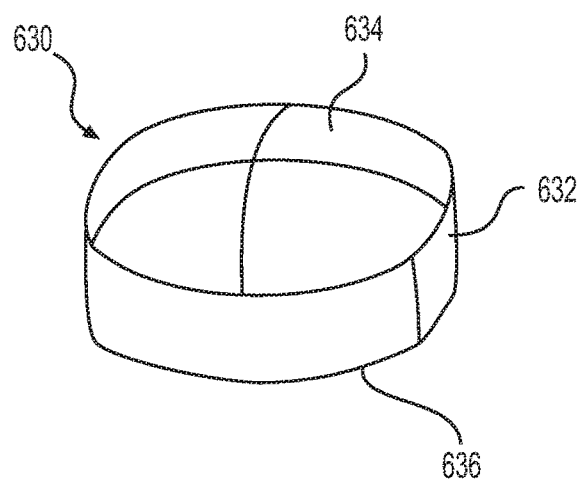
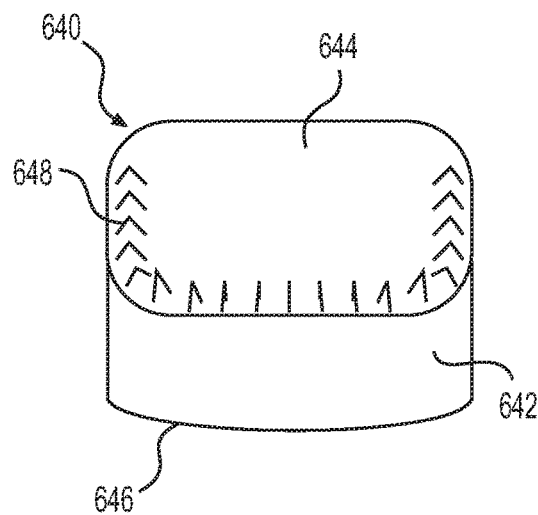
FIG. 107  FIG. 108
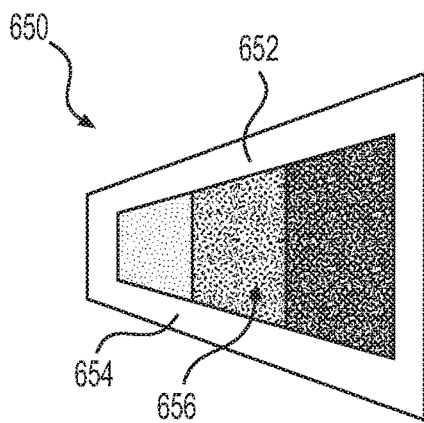
FIG. 109

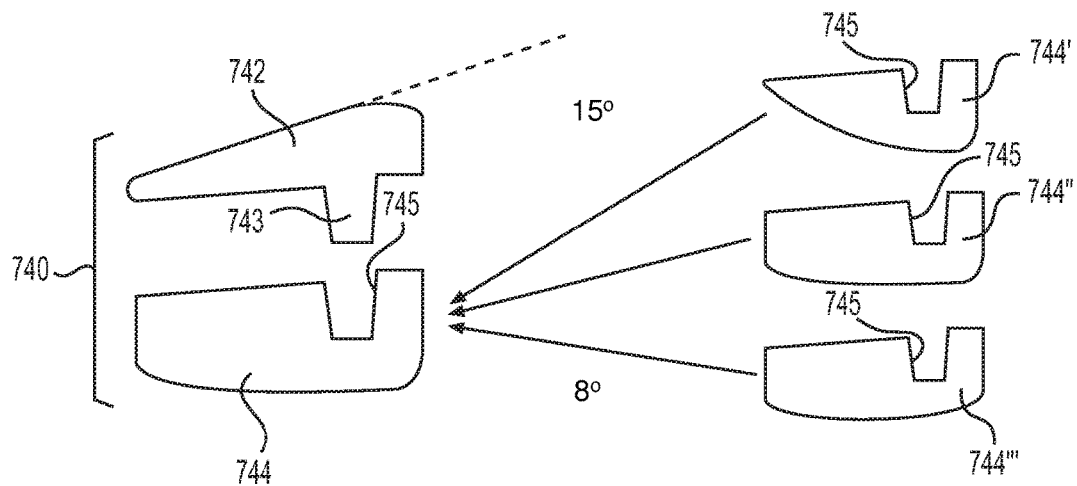
FIG. 129
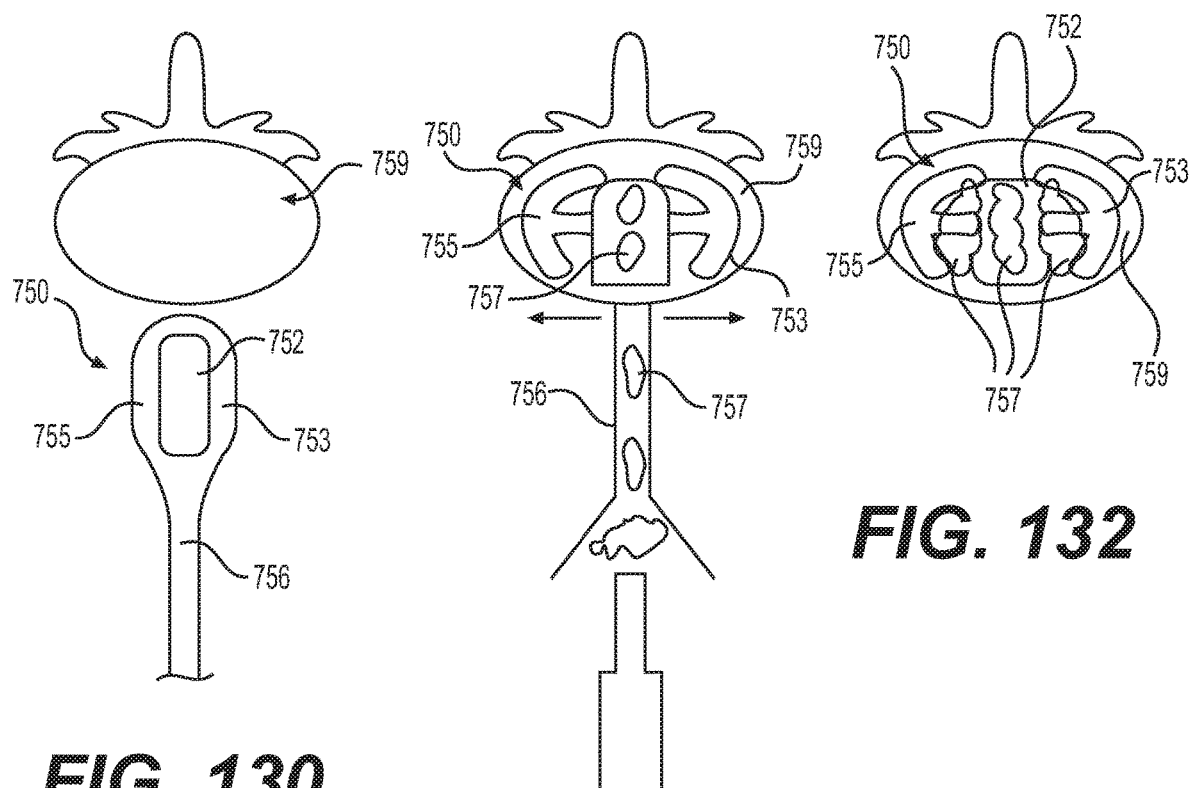
FIG. 130
FIG. 131
FIG. 132

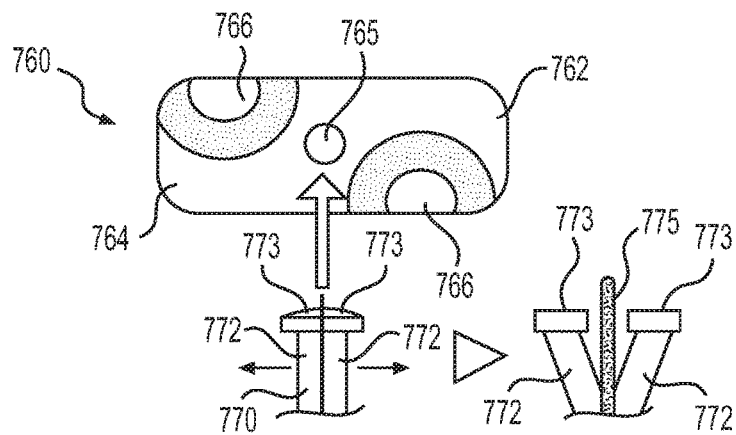
FIG. 133
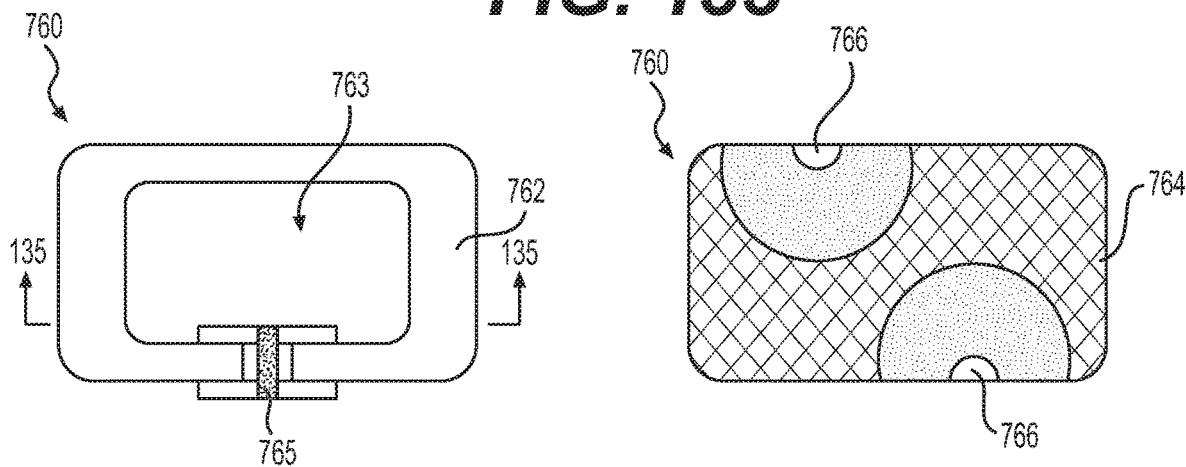
FIG. 134
FIG. 135
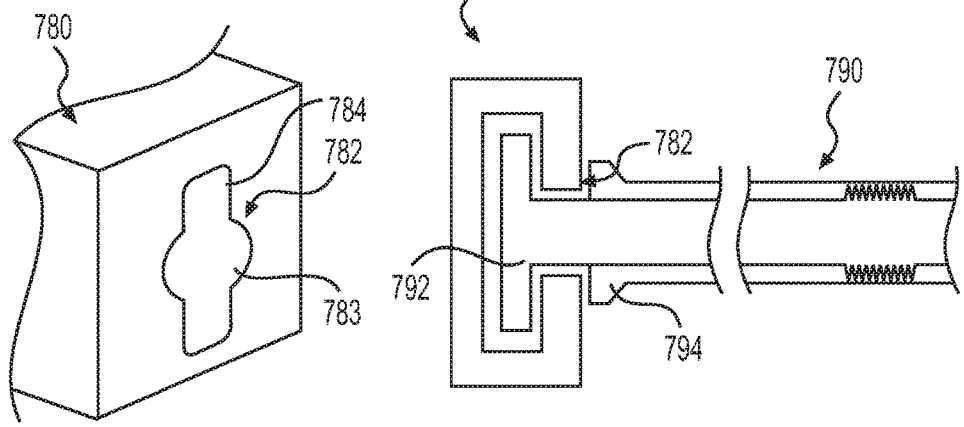
FIG. 136
FIG. 137

INTERVERTEBRAL SPINAL IMPLANT

CROSS REFERENCE TO RELATED APPLICATION

This application is a continuation-in-part of U.S. patent application Ser. No. 15/973,818, filed May 8, 2018, which is incorporated by reference herein in its entirety for all purposes.

This patent application is also related to U.S. patent application Ser. No. 15/973,609 filed May 8, 2018; U.S. patent application Ser. No. 15/973,756 filed May 8, 2018; U.S. patent application Ser. No. 15/973,772 filed May 8, 2018; U.S. patent application Ser. No. 15/973,788 filed May 8, 2018; U.S. patent application Ser. No. 15/973,801 filed May 8, 2018; and U.S. patent application Ser. No. 15/973,831 filed May 2018, which are all incorporated by reference herein in their entireties for all purposes.

FIELD

The present disclosure generally relates to fixation devices and systems for positioning and immobilizing at least two adjacent vertebrae and methods related to the same. In particular, the present disclosure relates to interbody fusion devices with an integrated solid support structure and porous ingrowth structure.

BACKGROUND

The spine is the axis of the skeleton on which all of the body parts "hang". In humans, the normal spine has seven cervical, twelve thoracic and five lumbar segments. The lumbar spine situs upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The central of adjacent vertebrae are supported by intervertebral discs. The spinal disc and/or vertebral bodies may be displaced or damaged due to trauma, disease, degenerative defects, or wear over an extended period of time. One result of this displacement or damage to a spinal disc or vertebral body may be chronic back pain. In many cases, to alleviate back pain from degenerated of herniated discs, the disc is removed along with all or part of at least one neighboring vertebrae and is replaced by an implant that promotes fusion of the remaining bony anatomy.

However, the success or failure of spinal fusion may depend upon several factors. For instance, the spacer or implant or cage used to fill the space left by the removed disc and bony anatomy must be sufficiently strong to support the spine under a wide range of loading conditions. The spacer should also be configured so that it likely to remain in place once it has been positioned in the spine by the surgeon. Additionally, the material used for the spacer should be biocompatible material and should have a configuration that promotes bony ingrowth.

SUMMARY

To meet this and other needs, intervertebral implants for use with the anterior, antero-lateral, lateral, and/or posterior portions of at least one motion segment unit of the spine, systems, and methods are provided. Traditionally, interbody spacers or implants intended to help facilitate intervertebral fusion may serve as a means to restore intervertebral height and/or lordosis. The implant may feature a central lumen to house bone graft material. It is through this central lumen where most of the fusion may occur. The implants of the disclosure incorporate a volumetric, interconnected porosity throughout the entire spacer. This enables bone to grow into and/or through the spacer, making it part of the fusion mass. The incorporation of a volumetric, interconnected porosity within the implant may encourage faster, stronger intervertebral fusion.

According to one embodiment, an intervertebral implant for implantation in an intervertebral space between vertebrae is disclosed. The implant includes a body extending from an upper surface to a lower surface. The body has a front end, a rear end and a pair of spaced apart first and second side walls extending between the front and rear walls such that an interior chamber is defined within the front and rear ends and the first and second walls. The body defines an outer perimeter and an inner perimeter extending about the internal chamber. At least one of the side walls is defined by an integral porous structure which extends from the outer perimeter to the inner perimeter. The at least one of the side walls is free of vertical solid support structure between the upper and lower surface.

According to another embodiment, an intervertebral implant for implantation in an intervertebral space between vertebrae is provided. The implant includes a body having a front end, a rear end and opposed side walls extending between the ends. The body has an outer perimeter and an inner perimeter about an internal chamber. The includes an upper surface and a lower surface with the upper surface defined by a solid upper outer rim and a spaced apart solid upper inner rim and the lower surface defined by a solid lower outer rim and a spaced apart solid lower inner rim. A solid front wall extends at the front end between at least the solid upper outer rim and the solid lower outer rim. A solid rear wall extends at the rear end between at least the solid upper outer rim and the solid lower outer rim. Each of the side walls is free of any solid struts extending between the upper and lower surfaces. A porous structure is integrally formed with the solid upper rims, the solid lower rims, and the solid front and rear walls and extends from the body outer perimeter to the body inner perimeter.

According to another embodiment, a method of forming an intervertebral implant for implantation in an intervertebral space between vertebrae is provided. The method includes forming an upper surface defined by a solid upper outer rim and a spaced apart solid upper inner rim; forming a lower surface defined by a solid lower outer rim and a spaced apart solid lower inner rim; forming a solid front wall extending at a front end between at least the solid upper outer rim and the solid lower outer rim; forming a solid rear wall extending at a rear end between at least the solid upper outer rim and the solid lower outer rim; forming side walls extending between the front and rear ends with each of the side walls free of any solid struts extending between the upper and lower surfaces; and forming a porous structure integral with the solid upper rims, the solid lower rims and the solid front and rear walls, the porous structure extending from an outer perimeter of the implant to an inner perimeter extending about an internal chamber of the implant.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein:

FIGS. 1-4 are perspective, side, top and rear views, respectively, of an intervertebral implant according to one embodiment of the disclosure with the porous portions shown textured;

FIGS. 8-10 are perspective, top and side views, respectively, of an intervertebral implant according to another embodiment of the disclosure with the porous portions shown translucently;

FIGS. 11-13 are perspective, top and side views, respectively, of an intervertebral implant according to another embodiment of the disclosure with the porous portions shown translucently;

FIGS. 20-22 and 24 are perspective, top, side and rear views, respectively, of an intervertebral implant according to another embodiment of the disclosure with the porous portions shown textured.

FIGS. 25-27 are perspective, top and side views, respectively, of the intervertebral implant of FIGS. 20-24 with the porous portions removed to show the support structure;

FIGS. 28-31 are perspective, top, side and rear views, respectively, of an intervertebral implant according to another embodiment of the disclosure with the porous portions shown textured;

FIGS. 40-43 are perspective, top, side and rear views, respectively, of an intervertebral implant according to another embodiment of the disclosure with the porous portions shown textured;

FIGS. 44-47 are perspective, top, side and rear views, respectively, of the intervertebral implant of FIGS. 40-43 with the porous portions removed to show the support structure;

FIGS. 48-51 are perspective, top, side and rear views, respectively, of an intervertebral implant according to another embodiment of the disclosure with the porous portions shown translucently;

FIGS. 54-57 are perspective, rear, top and side views, respectively, of an intervertebral implant according to another embodiment of the disclosure with the porous portions shown translucently;

FIGS. 73-75 are perspective, top and side views, respectively, of an intervertebral implant according to another embodiment of the disclosure with the porous portions shown translucently;

FIGS. 93-96 are perspective, bottom, side and rear views, respectively, of the intervertebral implant of FIGS. 89-92 with the porous portions removed to show the support structure;

103 is a cross-sectional view along the line 103-103 in FIG. 102

FIGS. 105 and 106 are front and perspective views, respectively, illustrating a grid porous configuration;

FIG. 107 is a perspective view of an intervertebral implant according to another embodiment of the disclosure;

FIG. 108 is a perspective view of an intervertebral implant according to another embodiment of the disclosure;

FIG. 109 is a side view of an intervertebral implant according to another embodiment of the disclosure;

FIG. 129 is an exploded side view of an intervertebral implant according to another embodiment of the disclosure;

FIGS. 130-132 are top views showing sequentially implantation of an expandable intervertebral implant according to another embodiment of the disclosure;

FIGS. 133 and 134 are front and top views, respectively, of an intervertebral implant according to another embodiment of the disclosure and FIG. 135 is a cross-sectional view along the line 135-135 in FIG. 134;

FIG. 136 is a perspective view illustrating an example tool hole and FIG. 137 is a cross-sectional view illustrating a toll engaged in such a hole;

DETAILED DESCRIPTION

Figure 5:
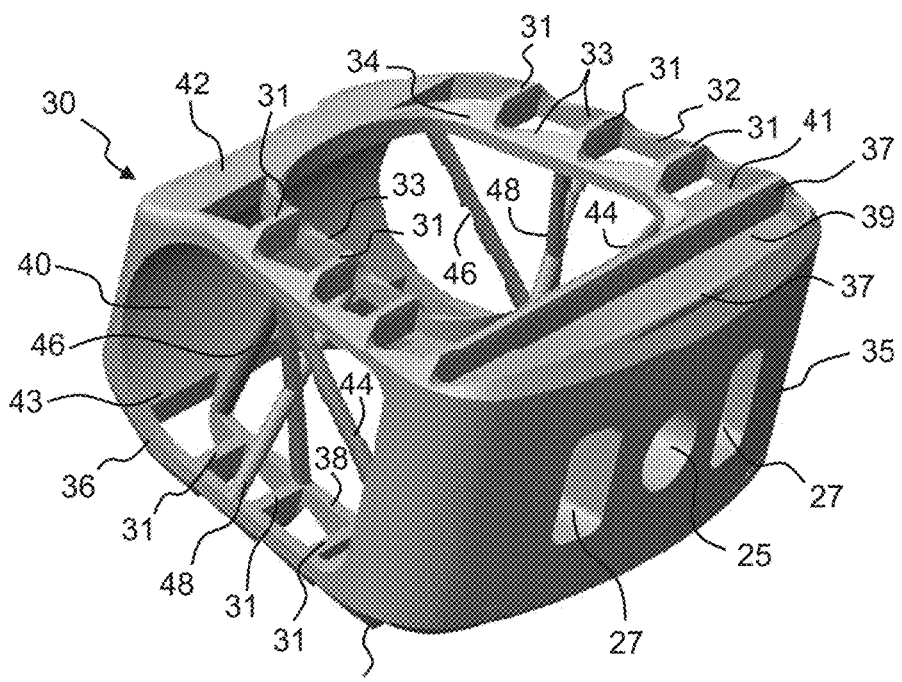
FIGS. 5-7 are perspective, top and side views, respectively, of the intervertebral implant of FIGS. 1-4 with the porous portions removed to show the support structure.

Embodiments of the disclosure are generally directed to intervertebral implants, systems, and method of use thereof. The implant may be suitable for use with the anterior, antero-lateral, lateral, and/or posterior portions of at least one motion segment unit of the spine. Traditionally, interbody spacers or implants intended to help facilitate intervertebral fusion may serve as a means to restore intervertebral height and/or lordosis. The implants may feature a central lumen to house bone graft material, for example. It is through this central lumen where most of the fusion may occur. The implants of the disclosure may incorporate a volumetric, interconnected porosity throughout the entire spacer or a portion thereof. This enables bone to growth into and/or through the spacer or a portion thereof, making it part of the fusion mass. The incorporation of a volumetric, interconnected porosity may encourage faster, stronger intervertebral fusion, thereby providing for better patient outcomes.

Various forms of additive manufacturing, or 3D printing, have been developed which allow structures to be formed layer by layer. One illustrative 3D printing technology is Direct Metal Laser Sintering (DMLS) wherein parts are built using a laser to selectively sinter (heat and fuse) a powdered metal material into layers. The process begins once a 3D CAD file is mathematically sliced into multiple 2D cross sections and uploaded into the system. After the first layer is produced, the build platform is lowered, another powder layer is spread across the plate, and the laser sinters the second layer. This process is repeated until the part is complete. Layer-by-layer manufacturing allows for the direct fabrication of complex parts that would be cost-prohibitive, and often impossible, to produce through traditional manufacturing processes. The powder layer thickness used during the fabrication of the spacers may be as thin at 30 μm. The resolution of the laser may be as fine as 70 μm. Although it is envisioned that any suitable thickness or laser resolution may be used or selected.

The disclosure is not limited to DMLS, but various 3D printing methods may be utilized. For example, VAT Photopolymerization utilizes a vat of liquid photopolymer resin which is cured through selective exposure to light (via a laser or projector) which then initiates polymerization and converts the exposed areas to a solid part. As another example, Powder Bed Fusion, of which DMLS is a subcategory, utilizes powdered materials which are selectively consolidated by melting it together using a heat source such as a laser or electron beam. The powder surrounding the consolidated part acts as support material for overhanging features. As yet another example, in Binder Jetting Liquid bonding agents are selectively applied onto thin layers of powdered material to build up parts layer by layer. The binders include organic and inorganic materials. Metal or ceramic powdered parts are typically fired in a furnace after they are printed. Material Jetting is another example of a 3D printing process which may be utilized wherein droplets of material are deposited layer by layer to make parts. Common varieties include jetting a photocurable resin and curing it with UV light, as well as jetting thermally molten materials that then solidify in ambient temperatures. As another example, in Sheet Lamination sheets of material are stacked and laminated together to form an object. The lamination method can be adhesives or chemical (paper/plastics), ultrasonic welding, or brazing (metals). Unneeded regions are cut out layer by layer and removed after the object is built. Another example of a 3D printing process that may be utilized is Material Extrusion wherein material is extruded through a nozzle or orifice in tracks or beads, which are then combined into multi-layer models. Common varieties include heated thermoplastic extrusion and syringe dispensing. Yet another example is Directed Energy Deposition wherein powder or wire is fed into a melt pool which has been generated on the surface of the part where it adheres to the underlying part or layers by using an energy source such as a laser or electron beam.

The implants of the disclosure may be manufactured from any of these or other additive manufacturing processes currently known or later developed. The implants may also be manufactured utilizing a combination of additive manufacturing processes and other manufacturing processes, for example, laser etching. Additionally, the implants may be further processed during and/or after manufacture utilizing various techniques, for example, abrasion, machining, polishing, or chemical treatment. The implants may be manufactured from various materials, such as biocompatible materials, including metals, polymers, ceramics or combinations thereof. Exemplary materials include Titanium (and Titanium alloys), Cobalt-Chrome, PEEK, and/or Stainless Steel, for example.

As will be discussed in more detail hereinafter, the implants of the disclosure generally comprise a solid support structure and a porous structure formed integral therewith. The solid support structure may include solid front and rear walls interconnected by upper and lower implant surfaces. The upper and lower surfaces may include spaced apart rims with cross struts interconnecting the rims. In many embodiments, the solid support structure of the upper and lower surfaces includes a plurality of openings in which the integral porous structure is formed such that the porous structure extends along at least a portion of the upper and lower implant surfaces. The side walls extending between the front and rear walls generally have a minimal solid structure, for example, a plurality of struts extending between the upper and lower rims, but otherwise have open area therebetween in which the integral porous structure is formed. The configuration of the solid structure is selected to provide the implant sufficient structural integrity and mechanical stability while maximizing the area of porous structure which facilitates better integration/incorporation with the adjacent bone. In several embodiments of the disclosure, the solid structure generally encases the corners of the porous structure or otherwise houses the porous structure therein to maintain the structural integrity of the porous structure.

Referring now to FIGS. 1-7, one embodiment of a cervical intervertebral implant 10 will be described. As illustrated, the implant 10 has a body 11 with a generally trapezoidal shape. The body 11 is defined by a tapered front end 12, a rectangular rear end 14 and side walls 16 and 18 extending therebetween. The implant 10 has an outer perimeter OP extending about the body 11. A hollow interior chamber 13 is defined within an inner perimeter IP of the body 11. The hollow interior chamber 13 is configured to receive bone growth promoting materials, for example. The implant 10 has an upper surface 20 and a lower surface 22, with both surfaces having a tapering portion 23 at the front end 12. The upper and lower surfaces 20, 22 may be substantially parallel or otherwise configured to provide the proper intervertebral spacing. The upper and lower surfaces 20, 22 define a plurality of serrations 24 along the side walls 16, 18 and a plurality of serrations 26 along the rear end 14. The serrations 24, 26 are defined by both the solid support structure 30 and the porous structure 50. As will be described in detail hereinafter, the solid support structure 30 includes spaced apart rims 32, 34 and 36, 38 with cross struts 31 and 37. The solid support structure 30 defines open spaces or recesses adjacent the cross struts 31, 37 and the porous structure 50 is formed within such open spaces such that the solid structure 30 and the porous structure 50 together form the serrations 24, 26. As illustrated in FIGS. 1-4, the porous structure 50 extends to and forms a portion of the implant upper and lower surfaces 20-22. The rear end 14 of the implant 10 includes a hole 25 and a pair of blind slots 27 for receiving an instrument that is used for inserting the implant 10. As seen in FIGS. 1-4, the implant 10 is defined by a solid support structure 30 with an interfiled, integral porous structure 50.

The solid support structure 30 will be described in more detail with reference to FIGS. 5-7. An outer rim 32 extends about the outer perimeter OP of the upper surface 20 and an inner rim 34 extends about the inner perimeter IP of the upper surface 20, i.e. about the interior chamber 13. Similarly, an outer rim 36 extends about the outer perimeter OP of the lower surface 22 and an inner rim 38 extends about the inner perimeter IP of the lower surface 22. A plurality of cross struts 31 extend between the outer rims 32, 36 and the respective inner rims 34, 38 along the side wall areas. As seen in the figures, the cross struts 31 along with contoured portions 33 of the rims 32, 34, 36, 38 define the contour of the serrations 24. In addition to interconnecting the rims within a given upper or lower surface, struts 44, 46 and 48 extend within each side wall area to interconnect the upper rims 32, 34 with the lower rims 36, 38. In the illustrated embodiment, a first strut 44 extends from the lower inner rim 38 to the upper outer rim 32 near the rear portion of the support structure 30, a second strut 46 extends from the lower inner rim 38 to the upper outer rim 32 near the front portion of the support structure 30 and an X-shaped strut 48 extends between both lower rims 36, 38 and both upper rims 32, 34 at a central location of the support structure 30. As can be seen in FIGS. 6 and 7, each of the first struts 44 extends from the lower inner rim 38 proximate the rear wall 35 at an angle to approximately the midpoint of the upper outer rim 32, substantially tangent to the curvature of the inner rims 34, 38. Similarly, each of the second struts 46 extends from the lower inner rim 38 proximate the front wall 40 at an angle to approximately the midpoint of the upper outer rim 32, substantially tangent to the curvature of the inner rims 34, 38. Each of the X-shaped struts 48 extends substantially parallel to the upper and lower rims and positioned at the point where the first and second struts 44, 46 meet with the upper outer rim 36. The struts may have other configurations and more or fewer struts may be utilized.

The solid rear wall 35 additionally interconnects the outer rims 32, 36 and the respective inner rims 34, 38 along the rear end area as well as further connecting the upper and lower structures together. The solid rear wall 35 defines the hole 25 and slots 27. Recessed areas 39 and 41 on the upper and lower sides of the rear wall 35 define receiving areas for porous structure, as seen in FIGS. 1-4. Cross members 37 in this area along with contours of the outer rims 32, 36 define the serrations 26. The solid front wall 40 has a concave configuration and also interconnects the outer rims 32, 36 and the respective inner rims 34, 38 along the front end area. The front wall 40 includes an upper sloped portion 42 extending between the upper outer rim 32 and inner rim 34 and a lower sloped portion 43 extending between the lower outer rim 36 and inner rim 38. While the rims and walls are described as specific elements for clarity, it is understood that the elements are formed as a unitary structure and may be formed as a smooth structure without any distinction between the elements.

Figure 6:
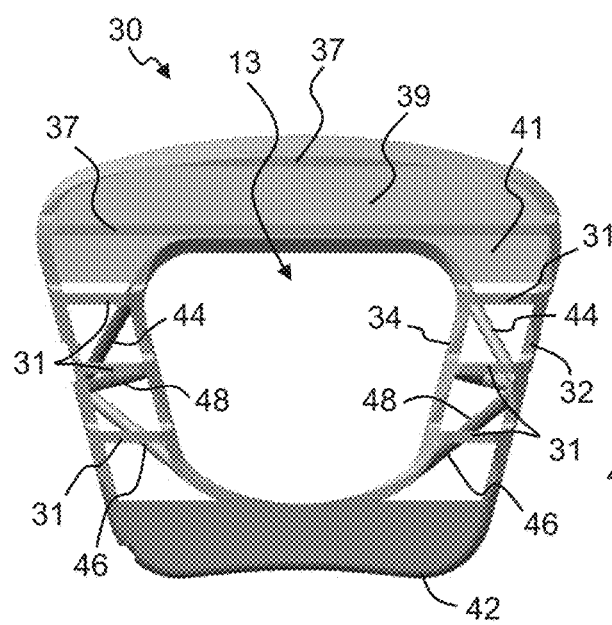
Figure 7:
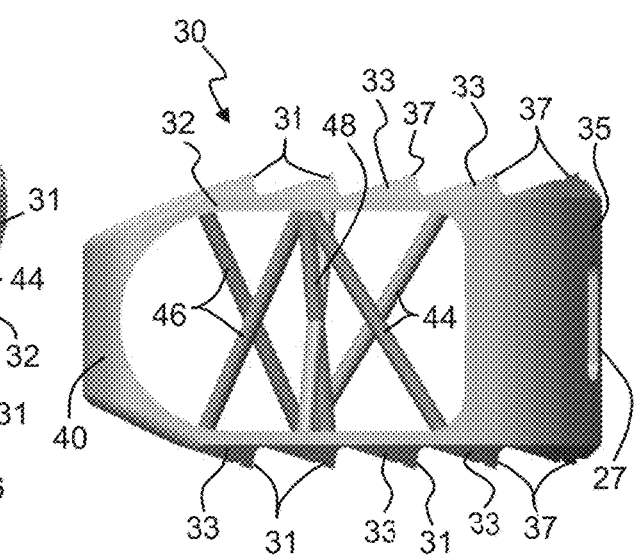

In the illustrations of the support structure 30 shown in FIGS. 5-7 with the porosity omitted for illustration, it is seen that there is significant open space between the upper rims 32, 34 and the lower rims 36, 38 with only the struts 44, 46, 48 therebetween. The struts 44, 46, 48 occupy only a minimal space between the upper and lower rims 32, 34, 36, 38, for example, less than 50% of the wall space, thereby leaving substantial open space for the porous structure 50. Additionally, there is open space between the inside surface of the front wall 40 and the inner rims 34, 38. Furthermore, there is open space on an inside surface and the recesses 39, 41 of the rear wall 35. As illustrated in FIGS. 1-4, in the implant 10, these open spaces are filled with the porous structure 50 such that the porous structure 50 encapsulates the struts 44, 46, 48 and extends from the upper surface 20 to the lower surface 22 and from the outer perimeter OP to the inner perimeter IP. In the illustrated embodiment, the porous structure 50 substantially defines the inner perimeter IP and defines a substantial portion of the side walls 16, 18 along the outer perimeter OP.

Figure 87:
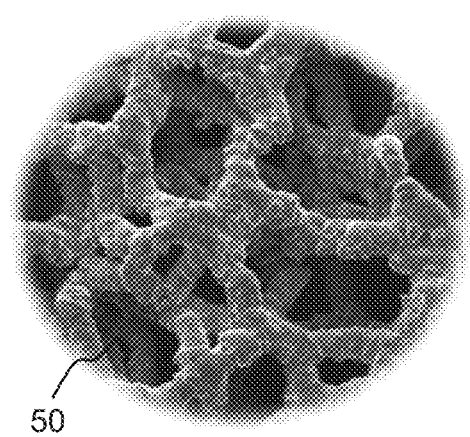
FIGS. 87 and 88 are illustrative photos of various porous structures in accordance with embodiments of the disclosure.
Figure 88:
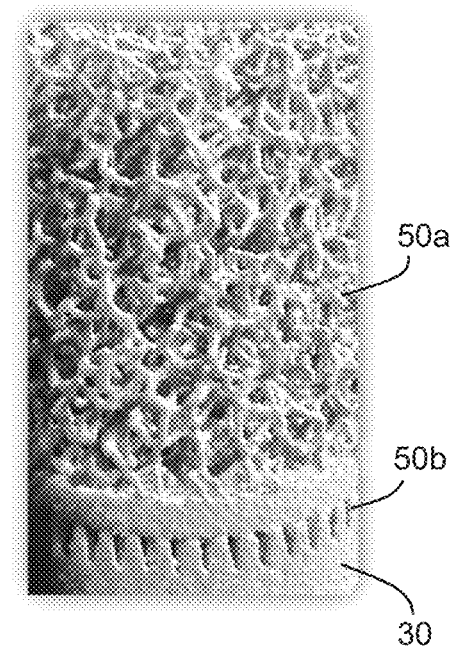
Figures 89, 90:
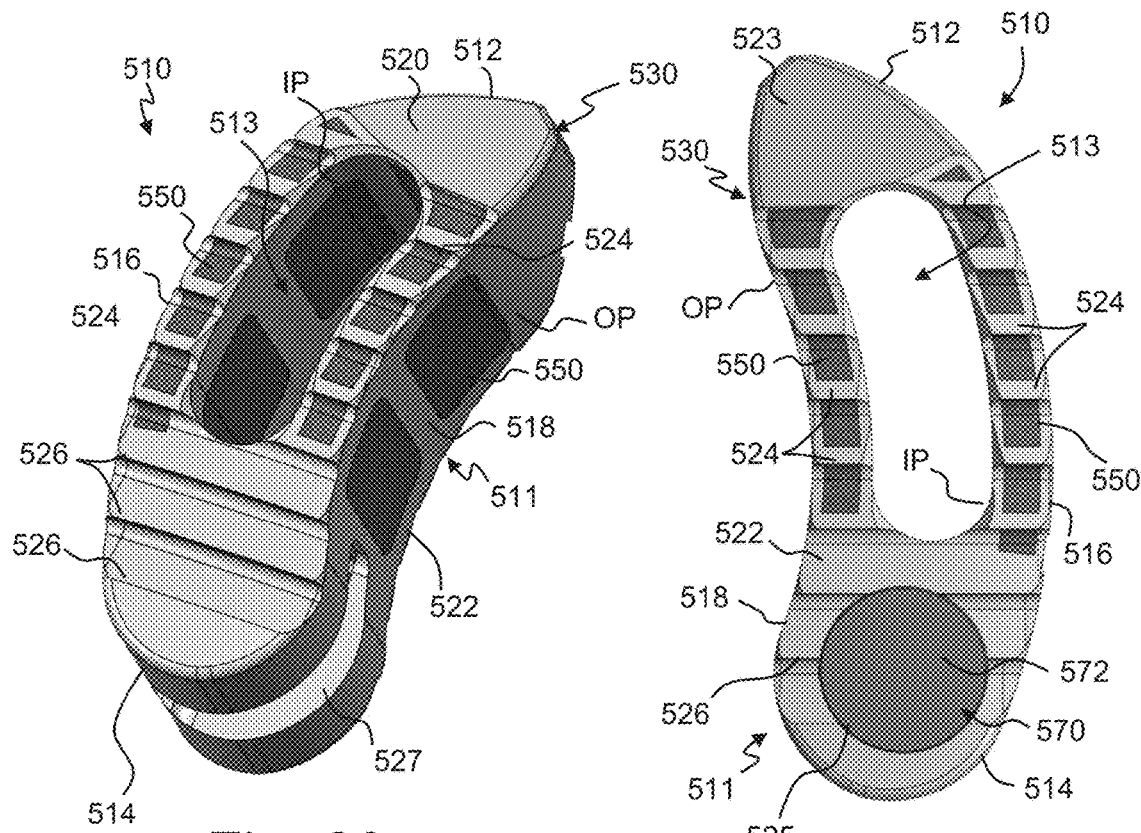
FIGS. 89-92 are perspective, bottom, side and rear views, respectively, of an intervertebral implant according to another embodiment of the disclosure with the porous portions shown textured.
Figures 91, 92:
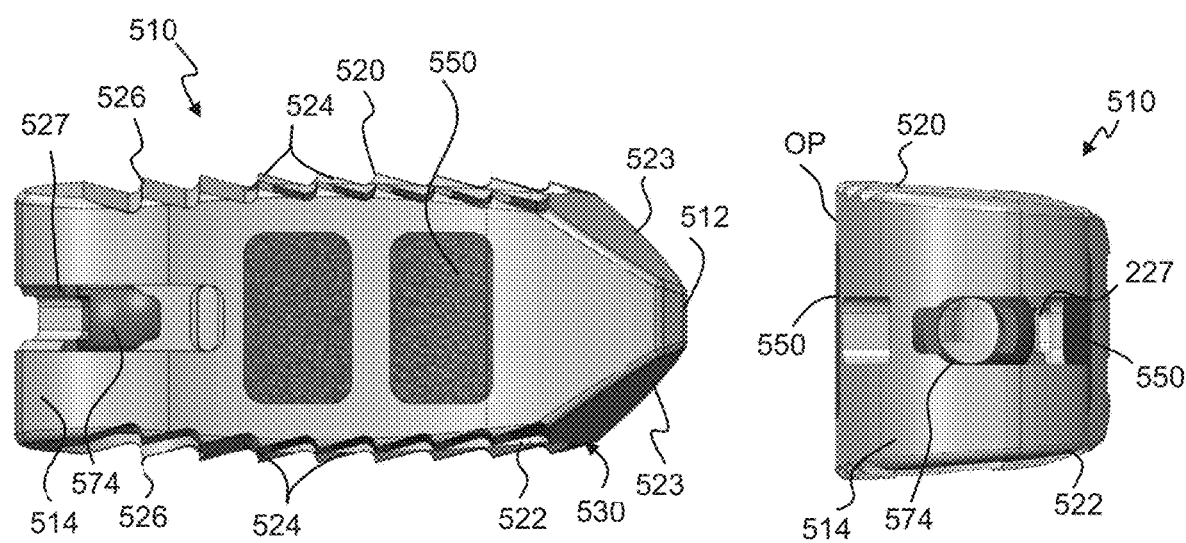

The configuration of the support structure 30 and the porous structure 50 are selected, for example, to provide the implant with an adequate construct strength while maximizing the potential for bony in-growth and allowing for clear radiographic imaging. Referring to FIGS. 87 and 88, the porous structure 50 may have a randomized pattern of open pores 50a or a repeating pattern of open pores 50b. The porous structure 50 may have a suitable porosity (open volume). For example, the porous structure 50 may be greater than 50% open, greater than 60% open, greater than 70% open, or approximately 70% open, or approximately 75% open. The porous structure 50 may feature interconnected pores or open pores. The porous structure 50 may have pores, for example, ranging from approximately 100 μm-2 mm, approximately 100 μm-1 mm, approximately 200-900 μm, or approximately 300-800 μm in diameter. The pore size may have an average pore size of about 300-800 μm, about 400-700 μm, or about 500-600 μm. The pore size distribution may be unimodal or bi-modal. Although spherical or partially-spherical pores or nodes are exemplified in forming the porous structure, it is envisioned that other suitable pore shapes and configurations may be used, for example, repeating or random patterns of cylinders, cubes, cones, pyramids, polyhedrons, or the like.

It is contemplated that different areas of the support structure 30 may have varying stiffness or strength, for example, variable A-P stiffness to achieve optimized load on an anterior graft or to achieve a desired level of flexibility within the implant 10. Furthermore, the porous structure 50 may have different porosities or densities in different areas of the implant 10. For example, the porous structure 50 may have a higher porosity or density along the inner perimeter compared to that at the outer perimeter, for example, with the inner area having a cancellous porosity and the outer area having a cortical porosity. The porous structure 50 may have various configurations, for example, a grid or honeycomb pattern which may promote bony in-growth. Additionally, the porous structure 50 may be configured such that when it is turned past a critical angle it may appear opaque, thereby helping with assessment of the implant orientation or positioning. The surface texture of both the support structure and the porous structure may be controlled to provide both macro and micro texturizing. The features and characteristics described with respect to this embodiment may be incorporated in any of the embodiments described herein. Additionally, features described in any of the embodiments herein may be incorporated into any of the other embodiments.

Referring now to FIGS. 8-10, a cervical intervertebral implant 10' in accordance with another embodiment of the disclosure will be described. The implant 10' is similar to the previous embodiment except for a slight modification in the structure of the support structure 30' and a corresponding modification in the porous structure 50'. Compared to the previous embodiment, the rear wall 35' has a narrower width with a portion of the rear end 14' having an open support structure into which the porous structure 50' extends. With the narrower width, the recesses portions 39', 41' open directly into the open space of the side walls 16', 18' and rear end 14'. To maintain sufficient implant strength, a pair of X-shaped struts 48', 48" are positioned in each of the side wall areas 16', 18' proximate the rear end 14' of the implant 10'. While the front end 12 of the implant 10' remains substantially the same as in the previous embodiment, an additional X-shaped strut 48''' is p positioned in each of the side wall areas 16', 18' proximate the rear end 14' of the implant 10'. Again, in the implant 10', the open spaces are filled with the porous structure 50' such that the porous structure 50' encapsulates the struts 44, 46, 48, 48', 48", 48''' and extends from the upper surface 20 to the lower surface 22 and from the outer perimeter OP to the inner perimeter IP. In the illustrated embodiment, the porous structure 50' substantially defines the inner perimeter IP and defines a substantial portion of the side walls 16', 18' and a portion of the rear end 14' along the outer perimeter OP.

Referring now to FIGS. 11-13, a cervical intervertebral implant 10" in accordance with another embodiment of the disclosure will be described. The implant 10" is similar to the previous embodiment except for slight modification in the structure of the support structure 30" and a corresponding modification in the porous structure 50". In the present embodiment, the struts within the side walls are replaced with external X-shaped struts 60, 62. Outer X-shaped struts 60 extend along each of the side walls 16", 18" along the outer perimeter OP. The outer X-shaped struts 60 extend between the upper and lower outer rims 32 and 36. Inner X-shaped struts 62 extend along each of the side walls 16", 18" along the inner perimeter IP. The inner X-shaped struts 62 extend between the upper and lower inner rims 34 and 38. A generally hollow wall space is defined between the outer and inner X-shaped struts 60, 62 on the sides and the cross struts 31, 37 on the top and bottom. These hollow wall spaces extend from the front wall 40 to the rear wall 35' and are filled with the integral porous structure 50". Again, in the implant 10", the open spaces are filled with the porous structure 50" such that it extends from the upper surface 20 to the lower surface 22 and from the outer perimeter OP to the inner perimeter IP. In the present embodiment, the struts 60, 62 are not encapsulated in the porous structure 50", but instead the struts 60 are coplanar with the porous structure 50" along the outer perimeter OP and the struts 62 are coplanar with the porous structure 50" along the inner perimeter IP. Again, the porous structure 50" substantially defines the inner perimeter IP and defines a substantial portion of the side walls 16", 18" and a portion of the rear end 14' along the outer perimeter OP.

Figure 14:
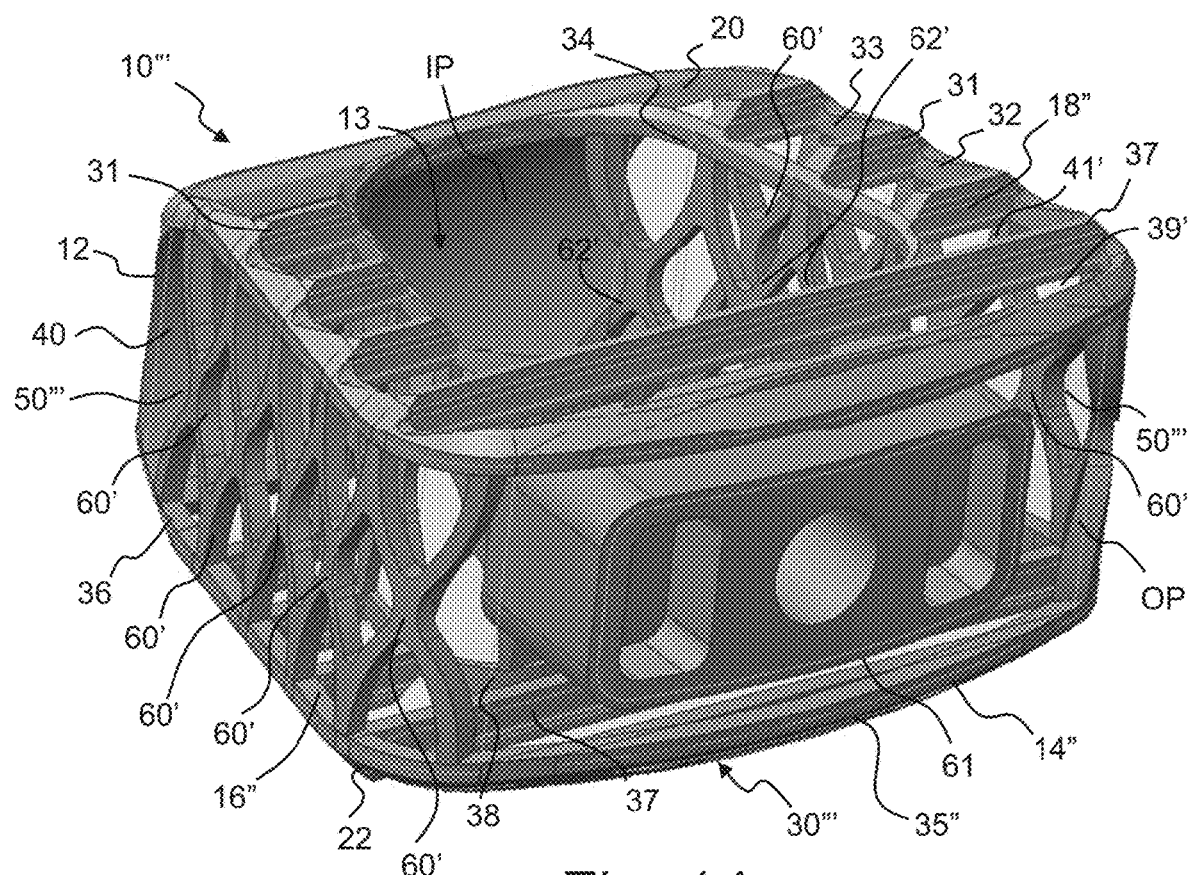
FIGS. 14-16 are perspective, top and side views, respectively, of an intervertebral implant according to another embodiment of the disclosure with the porous portions shown translucently.
Figure 15:
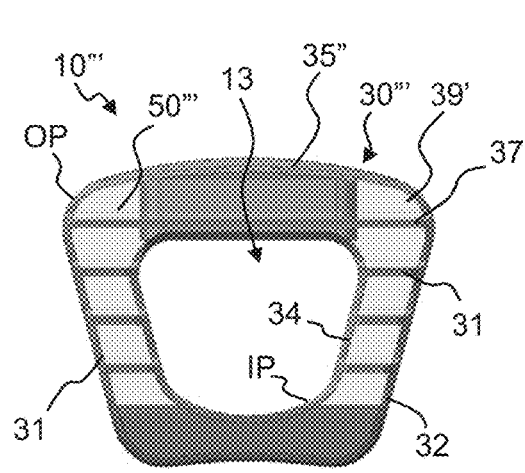
Figure 16:
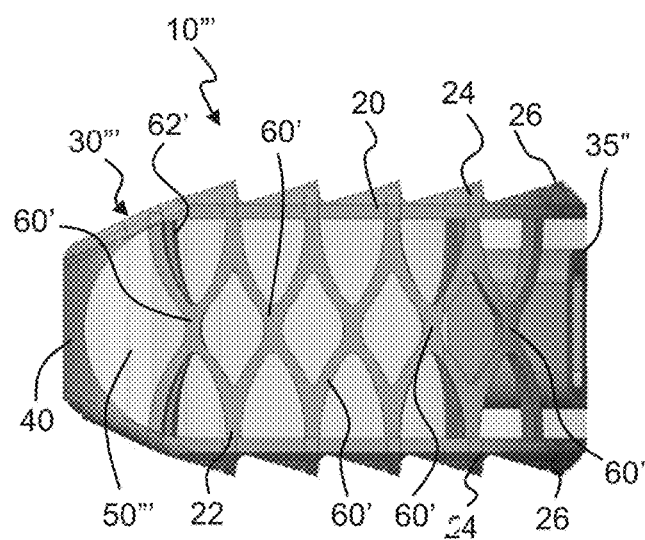

Referring now to FIGS. 14-16, a cervical intervertebral implant 10''' in accordance with another embodiment of the disclosure will be described. The implant 10''' is similar to the previous embodiment except for slight modification in the structure of the support structure 30''' and a corresponding modification in the porous structure 50'''. In the present embodiment, the external X-shaped struts 60', 62' have a narrower configuration and have curved portions compared to those of the previous embodiment. Again, outer X-shaped struts 60' extend along each of the side walls 16", 18" along the outer perimeter OP as they extend between the upper and lower outer rims 32 and 36. Inner X-shaped struts 62' extend along each of the side walls 16", 18" along the inner perimeter IP as they extend between the upper and lower inner rims 34 and 38. In the present embodiment, in the rear area 14" of the implant 10''', the rear wall 35" is not connected to the upper or lower rim 32, 36 and instead open spaces 61 extend therebetween. As in the previous embodiment, a generally hollow wall space is defined between the outer and inner X-shaped struts 60', 62' on the sides and the cross struts 31, 37 on the top and bottom. These hollow wall spaces extend from the front wall 40 to the rear wall 35" and are filled with the integral porous structure 50'''. As in the previous embodiments, all of the open spaces of the implant 10''' are filled with the porous structure 50''' such that it extends from the upper surface 20 to the lower surface 22 and from the outer perimeter OP to the inner perimeter IP. As in the previous embodiment, the struts 60', 62' are not encapsulated in the porous structure 50''', but instead the struts 60' are coplanar with the porous structure 50''' along the outer perimeter OP and the struts 62' are coplanar with the porous structure 50''' along the inner perimeter IP. Again, the porous structure 50''' substantially defines the inner perimeter IP and defines a substantial portion of the side walls 16", 18" and a portion of the rear end 14" along the outer perimeter OP.

Figure 17:
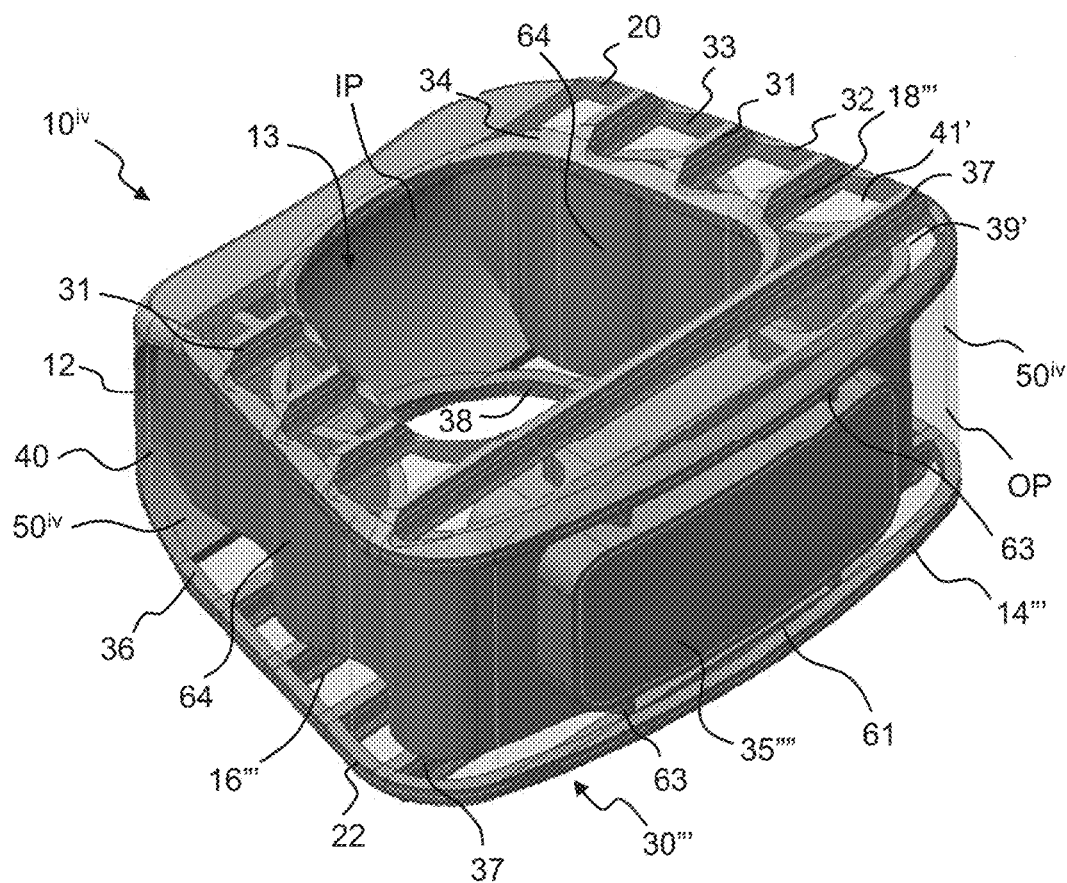
FIGS. 17-19 are perspective, top and side views, respectively, of an intervertebral implant according to another embodiment of the disclosure with the porous portions shown translucently.
Figures 18, 19:
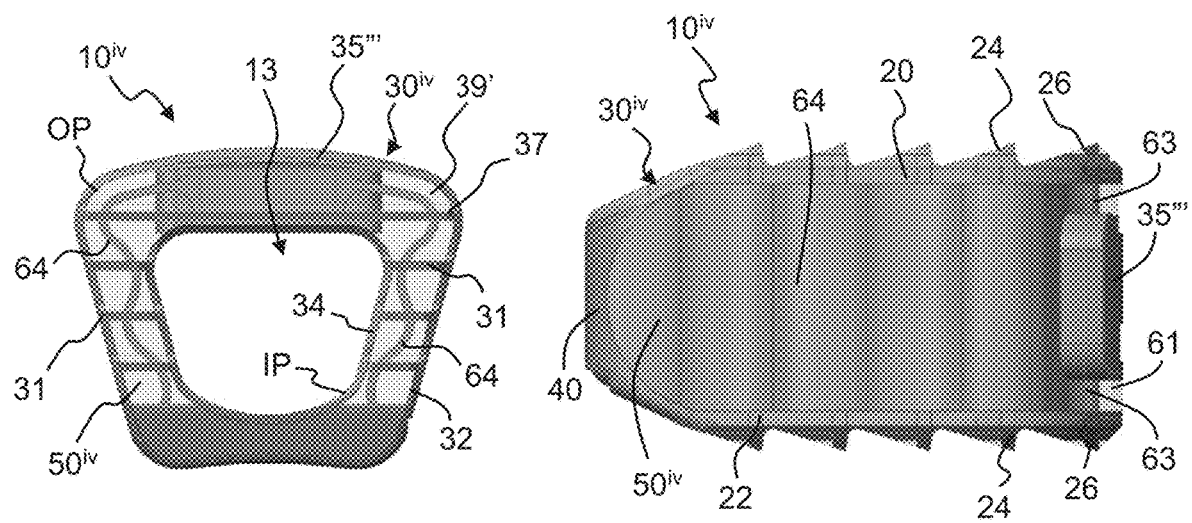
Figure 20:
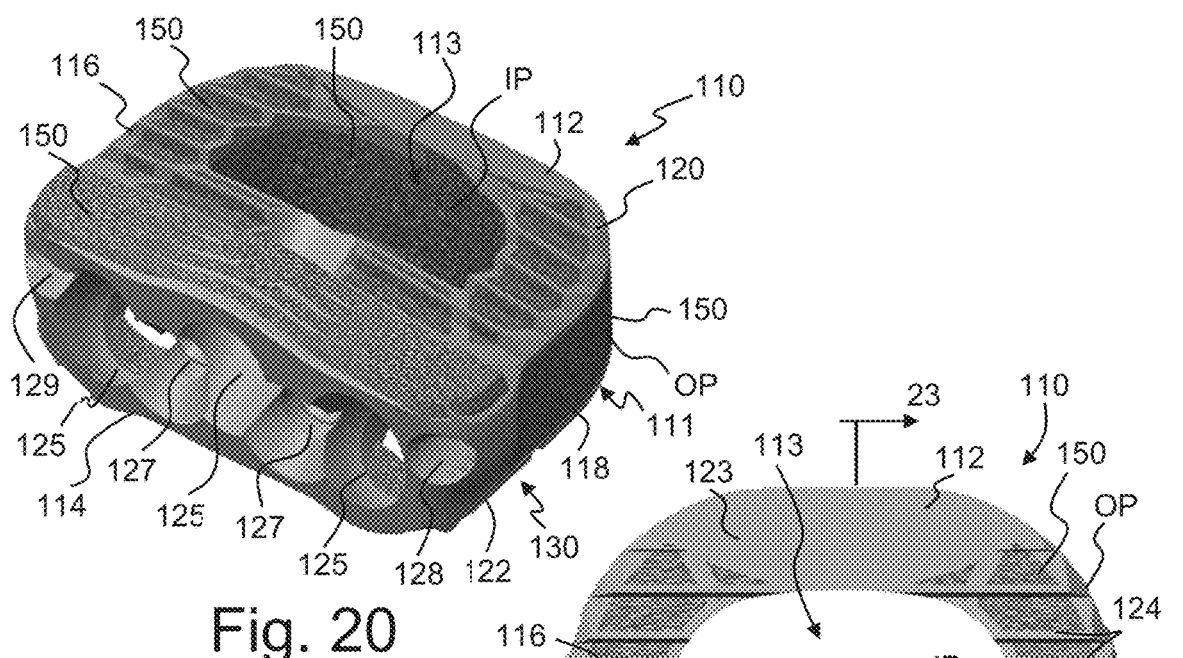
Figure 21:
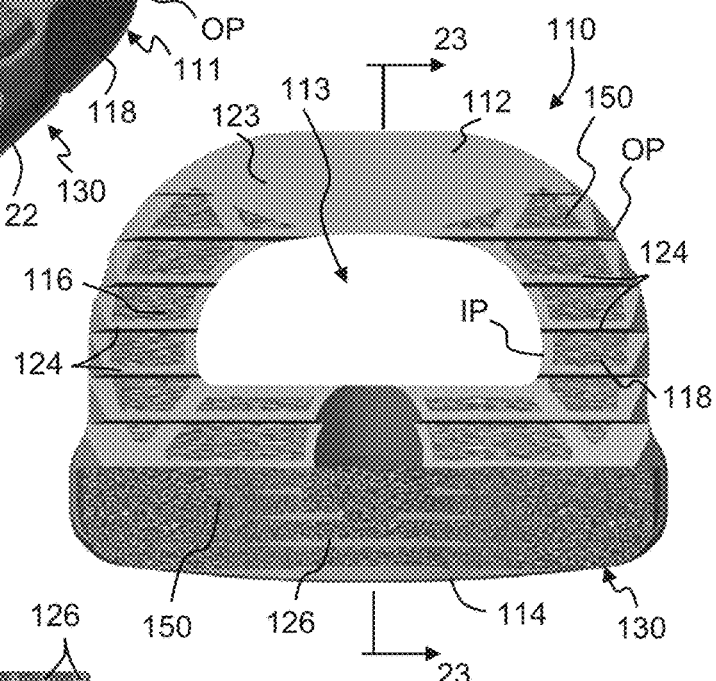
Figure 22:
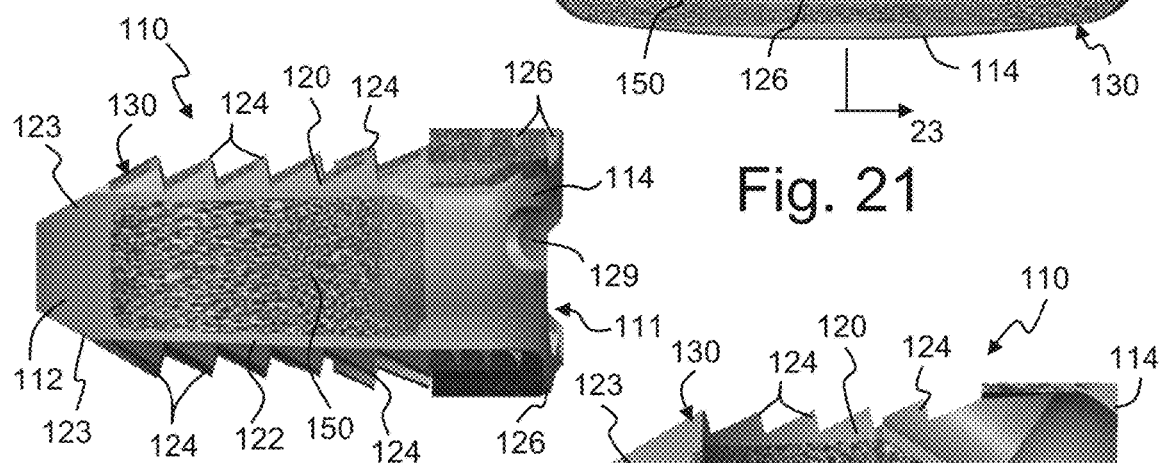
Figure 23:
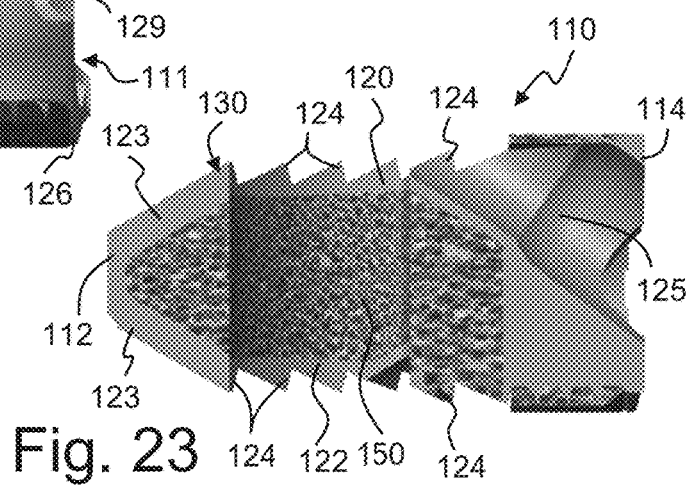
FIG. 23 is a cross-sectional view along the lines 23-23 in FIG. 21.
Figure 32:
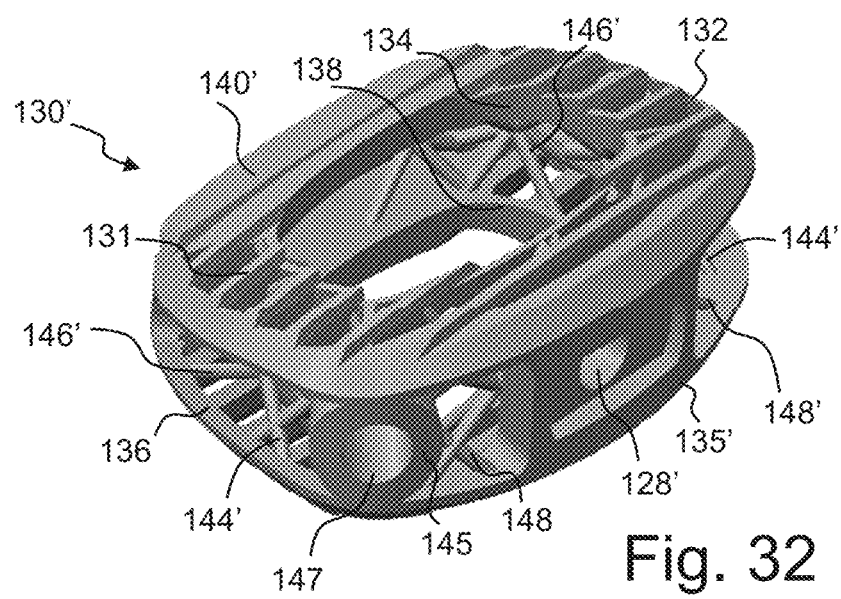
FIGS. 32-34 are perspective, top and side views, respectively, of the intervertebral implant of FIGS. 28-31 with the porous portions removed to show the support structure.
Figure 33:
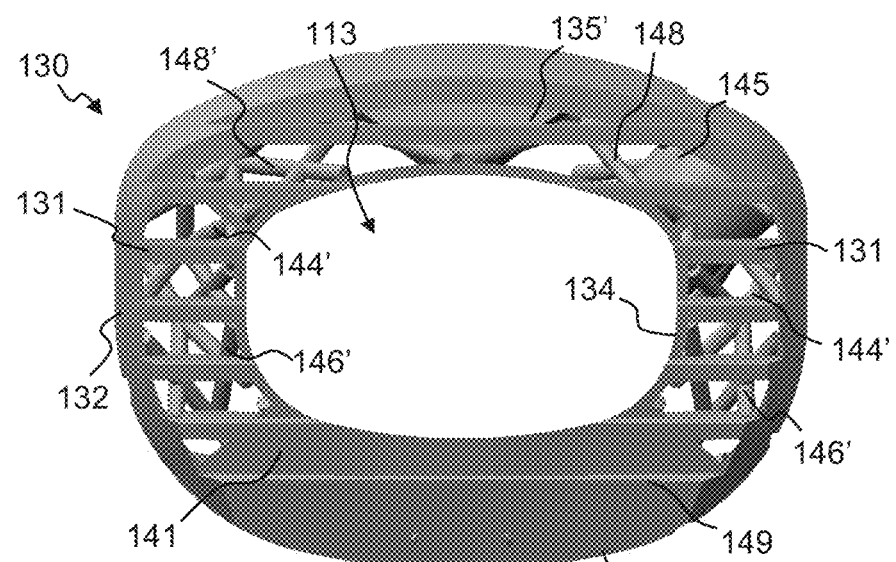
Figure 34:
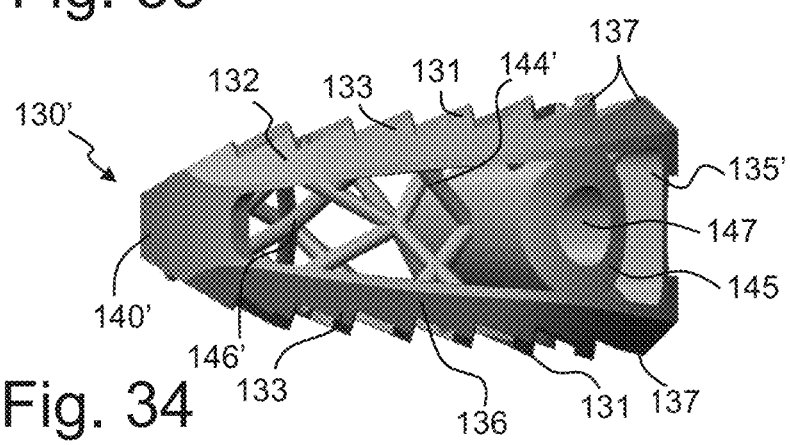

Referring now to FIGS. 17-19, a cervical intervertebral implant $10^{iv}$ in accordance with another embodiment of the disclosure will be described. The implant $10^{iv}$ is similar to the previous embodiment except for slight modification in the structure of the support structure $30^{iv}$ and a corresponding modification in the porous structure $50^{iv}$. In the present embodiment, the struts are replaced with an internal corrugated wall 64 within each of the side walls 16''', 18'''. Each corrugated wall 64 extends between the upper support structure and the lower support structure. In the illustrated embodiment, each corrugated wall 64 extends from the front wall 12, interconnects with the cross struts 31, 37 and interconnects with the rear wall 35'''. In the present embodiment, in the rear area 14" of the implant 10''', open spaces 61 extend between the rear wall 35''' and the upper or lower rims 32, 36 as in the previous embodiment, however, additional supports 63 extend between the upper rims 32, 34 and the rear wall 35''' and between the lower rims 36, 38 and the rear wall 35'''. As in the previous embodiments, all of the open spaces of the implant $10^{iv}$ are filled with the porous structure $50^{iv}$ such that it extends from the upper surface 20 to the lower surface 22. The porous structure $50^{iv}$ of the present embodiment encapsulates each corrugated wall 64 and while the porous structure $50^{iv}$ is not continuous from the outer perimeter OP to the inner perimeter IP, the porous structure $50^{iv}$ still substantially defines the inner perimeter IP and defines a substantial portion of the side walls 16", 18" and a portion of the rear end 14" along the outer perimeter OP.

Figure 148:
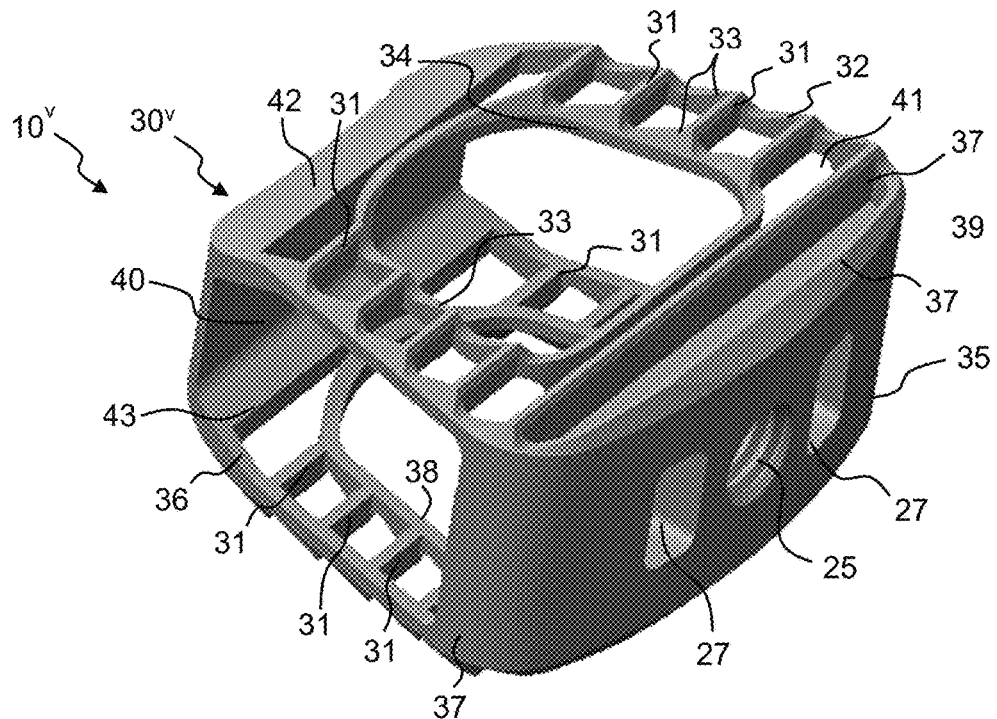
FIGS. 148-150 are perspective, top and side views, respectively, of an intervertebral implant according to another embodiment of the disclosure with the porous portions removed to show the support structure.
Figure 149:
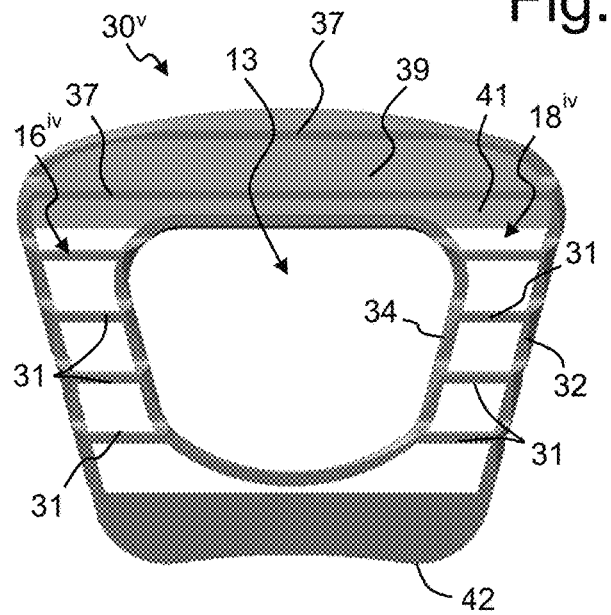
Figure 150:
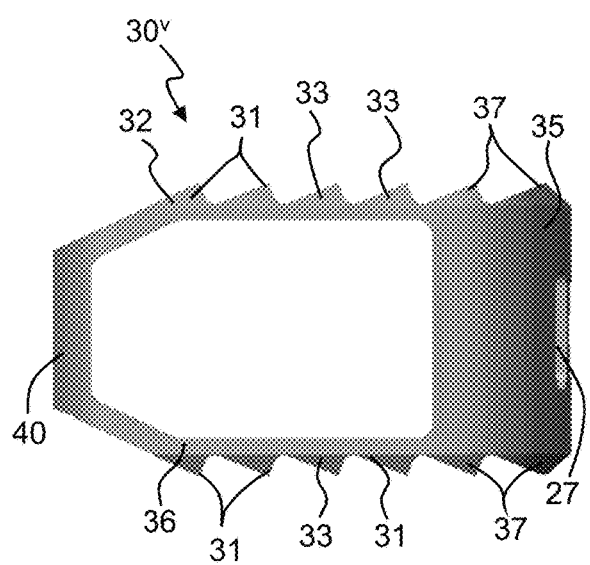
Figure 151:
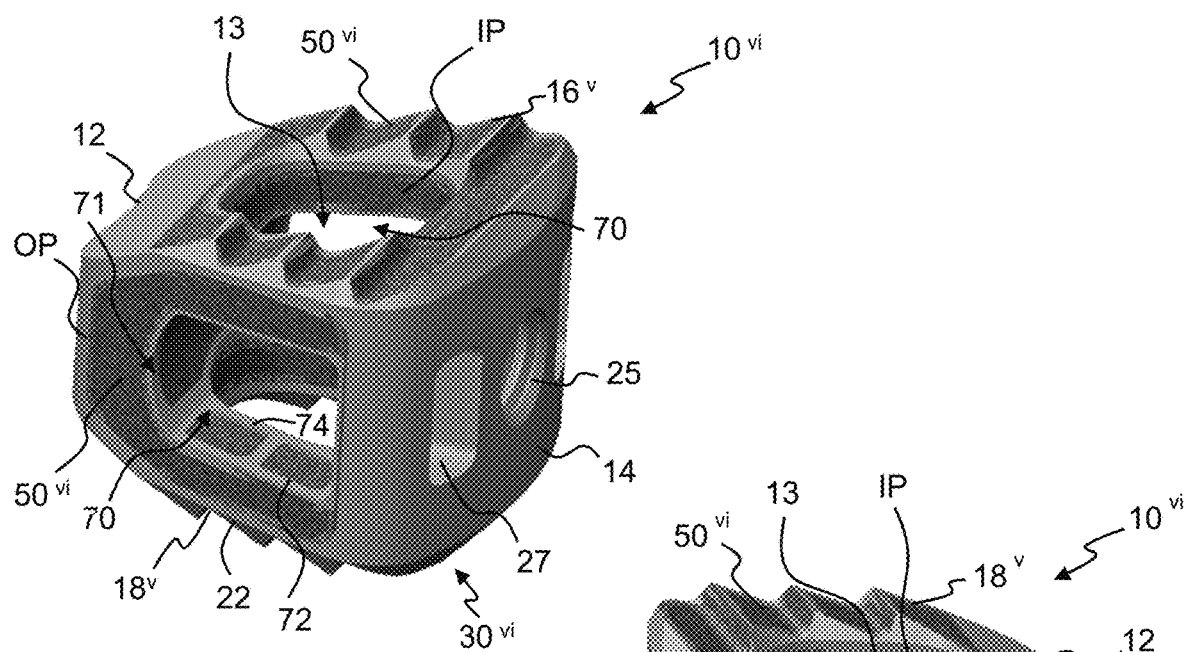
FIGS. 151-153 are left perspective, right perspective and side views, respectively, of an intervertebral implant according to another embodiment of the disclosure with the porous portions shown textured.
Figure 152:
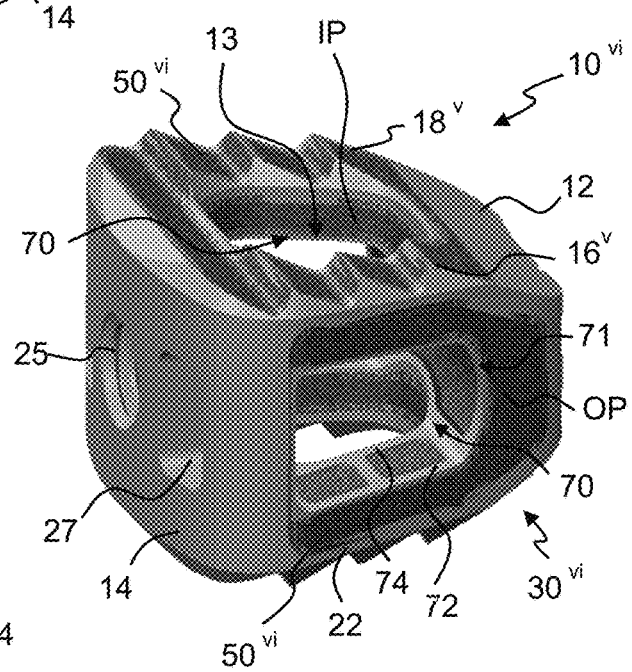
Figure 153:
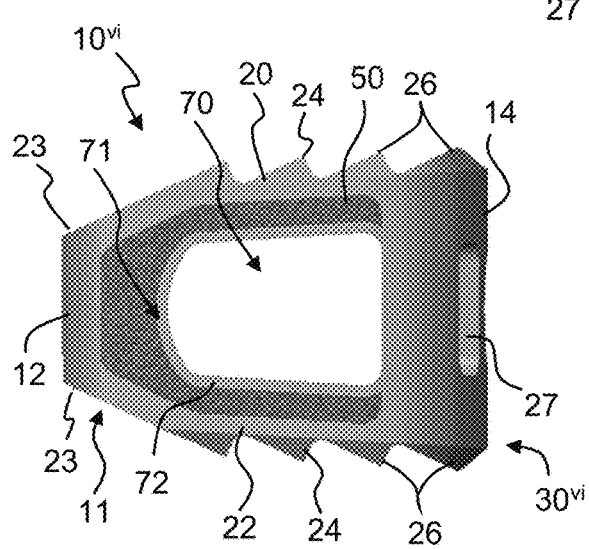
Figure 154:
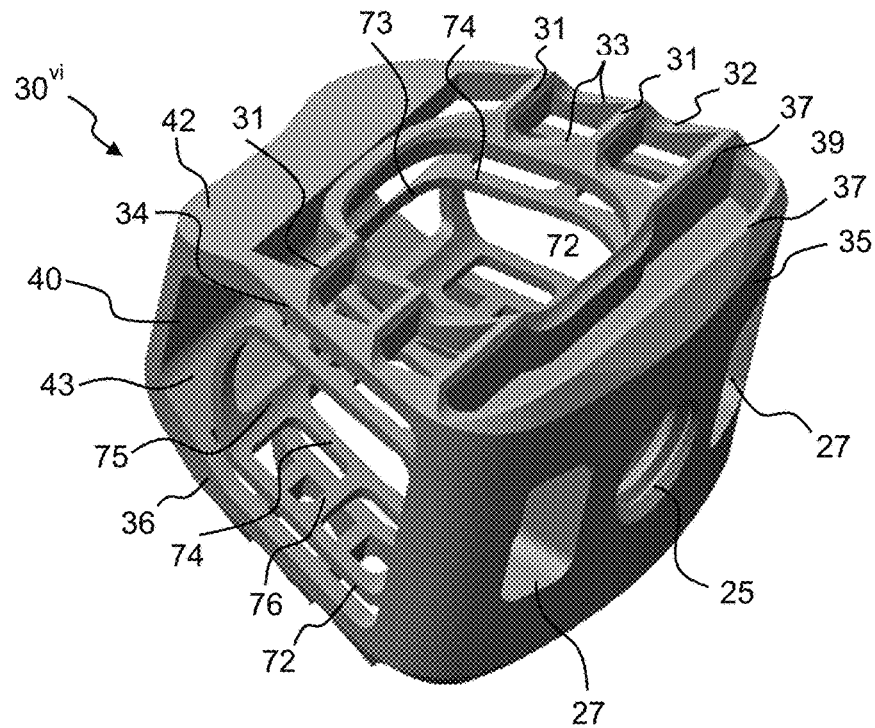
FIGS. 154-156 are perspective, top and side views, respectively, of the intervertebral implant of FIGS. 151-153 with the porous portions removed to show the support structure.
Figure 155:
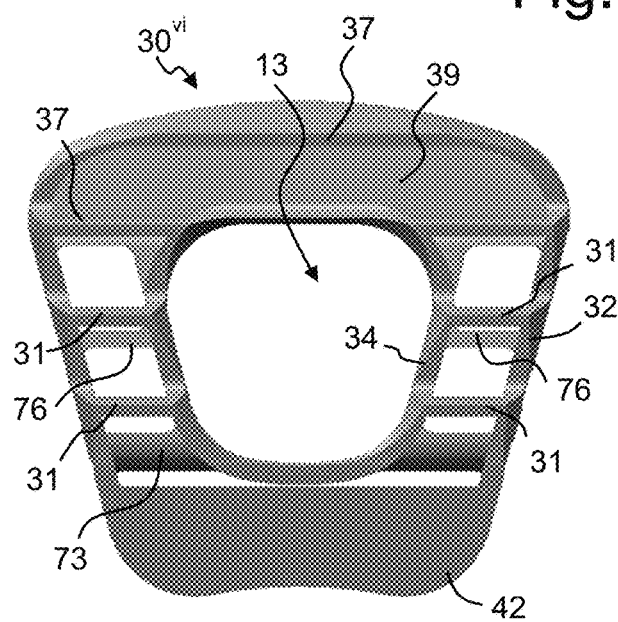
Figure 156:
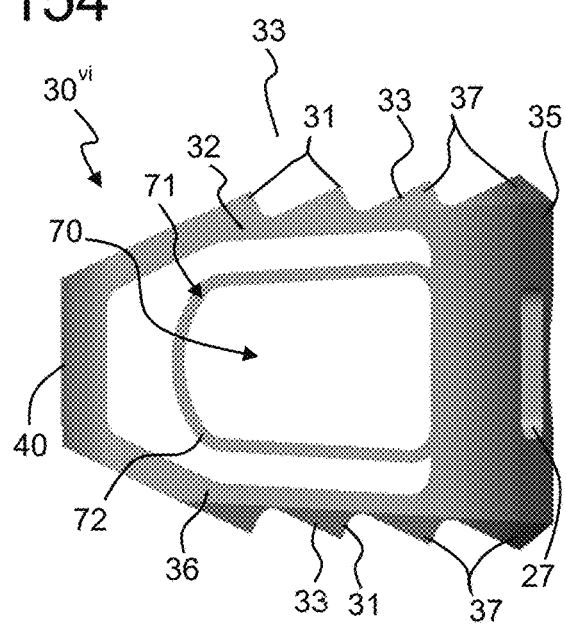
Figure 157:
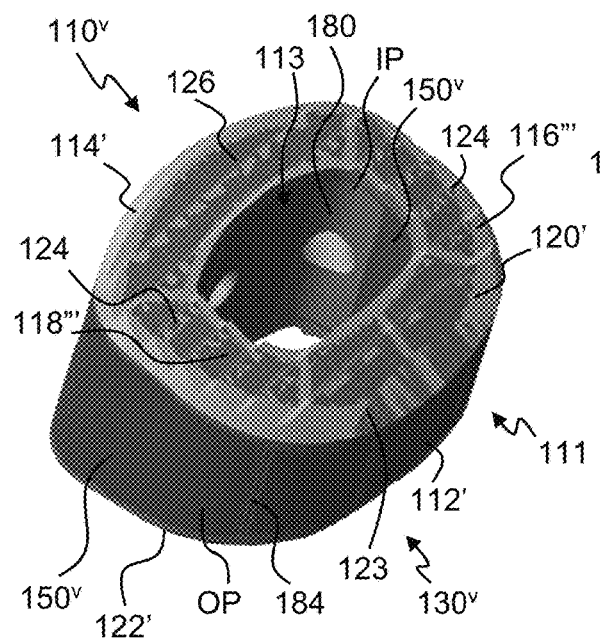
FIGS. 157-160 are perspective, top, side and rear views, respectively, of an intervertebral implant according to another embodiment of the disclosure with the porous portions shown textured.
Figure 158:
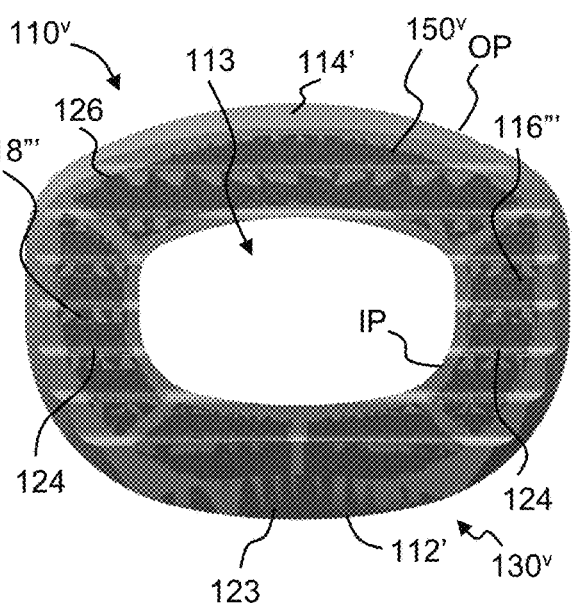
Figure 159:
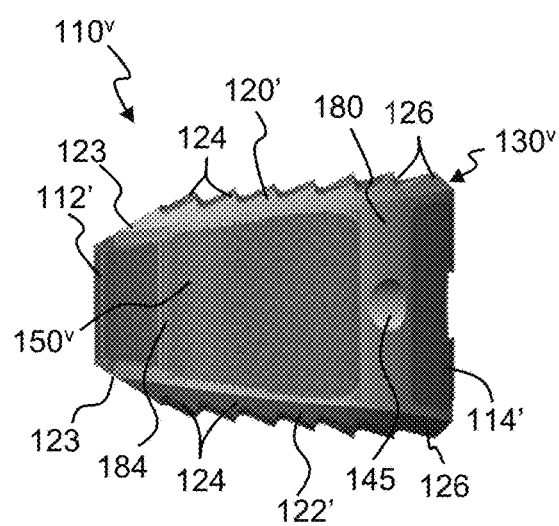

Referring now to FIGS. 148-150, a cervical intervertebral implant $10^v$ in accordance with another embodiment of the disclosure will be described. The implant $10^v$ is similar to the embodiment illustrated in FIGS. 1-7 except for slight modification in the structure of the support structure $30^v$ and a corresponding modification in the porous structure. In the present embodiment, the support structure $30^v$ is free of any struts within the side walls $16^{iv}$, $18^{iv}$. Instead, the upper outer rim 32 is interconnected to the lower outer rim 36 via the front and rear walls 40, 35 and the inner rims 34, 38 are connected to the respective outer rims 32, 36 via the cross struts 31. As in the previous embodiments, all of the open spaces of the implant $10^v$ are filled with the porous structure such that it extends from the upper surface 20 to the lower surface 22. The implant $10^v$ of the present embodiment looks substantially the same as the implant 10 of FIGS. 1-4 and the porous structure substantially defines the inner perimeter IP and defines a substantial portion of the side walls $16^{iv}$, $18^{iv}$ and a portion of the rear end 14 along the outer perimeter OP.

Referring now to FIGS. 151-156, a cervical intervertebral implant $10^{vi}$ in accordance with another embodiment of the disclosure will be described. The implant $10^{vi}$ is similar to the embodiment illustrated in FIGS. 148-150 except for slight modification in the structure of the support structure $3^{vi}$ and a corresponding modification in the porous structure. In the present embodiment, a lateral window 70 is defined through each of the side walls $16^v$, $18^v$. The lateral windows 70 may, for example, aid in assessing bony fusion in post-operative X-ray images. In the present embodiment, each lateral window 70 includes a respective solid window frame 71, however, it is understood that the lateral windows may be defined in the side walls $16^v$, $18^v$ by the porous structure $50^{vi}$ only without any solid frame or the like.

Each of the illustrative solid frames 71 includes an outer frame ring 72 and an inner frame ring 74. An intermediate cross strut 76 extends between each outer frame ring 72 and the respective inner frame ring 74. Additionally, an upper front strut 73 extends across the front of the support structure $30^{vi}$, interconnecting both the outer rings 72 and inner rings 74 of both solid frames 71. Similarly, a lower front strut 75 extends across the front of the support structure $30^{vi}$, interconnecting both the outer rings 72 and inner rings 74 of both solid frames 71. The rear ends of at least the outer rings 72 each connect with the rear wall 35 to cantileverly support each of the solid frames 71.

As in the previous embodiments, all of the open spaces of the implant $10^{vi}$ are filled with the porous structure $50^{vi}$ such that it extends from the upper surface 20 to the lower surface 22. The porous structure $50^{vi}$ substantially defines the inner perimeter IP and defines a substantial portion of the side walls $16^{iv}$, $18^{iv}$, with the lateral windows 70 extending therethrough.

Referring now to FIGS. 20-27, one embodiment of an anterior lumbar interbody fusion (ALIF) implant 110 will be described. As illustrated, the implant 110 has a body 111 with a generally D-shaped configuration. The body 111 is defined by a tapered front end 112, a rectangular rear end 114 and side walls 116 and 118 extending therebetween. The implant 110 has an outer perimeter OP extending about the body 111. A hollow interior chamber 113 is defined within an inner perimeter IP of the body 111. The hollow interior chamber 113 is configured to receive bone growth promoting materials. The implant 110 has an upper surface 120 and a substantially parallel lower surface 122, with both surfaces having a tapering portion 123 at the front end 112. The upper and lower surfaces 120, 122 define a plurality of serrations 124 along the side walls 116, 118 and a plurality of serrations 126 along the rear end 114. The rear end 114 of the implant 110 includes a plurality of screw holes 125 through which screws (not shown) extend to anchor the implant onto the vertebral body. Secondary holes 127 are provided to receive respective blocking set screws (not shown). A threaded hole 128 and a blind slot 129 are provided for receiving an instrument that is used for inserting the implant 110. As seen in FIGS. 20-24, the implant 110 is defined by a solid support structure 130 with an interfiled, integral porous structure 150.

The solid support structure 130 will be described in more detail with reference to FIGS. 25-25. An outer rim 132 extends about the outer perimeter OP of the upper surface 120 and an inner rim 134 extends about the inner perimeter IP of the upper surface 120, i.e. about the interior chamber 113. Similarly, an outer rim 136 extends about the outer perimeter OP of the lower surface 122 and an inner rim 138 extends about the inner perimeter IP of the lower surface 122. A plurality of cross struts 131 extend between the outer rims 132, 136 and the respective inner rims 134, 138 along the side wall areas. As seen in the figures, the cross struts 131 along with contoured portions 133 of the rims 132, 134, 136, 138 define the contour of the serrations 124. In addition to interconnecting the rims within a given upper or lower surface, struts 144, 146 extend within each side wall area to interconnect the upper rims 132, 134 with the lower rims 136, 138. In the illustrated embodiment, a first multi-leg strut 144 extends from the lower inner rim 138 to the upper outer rim 132 near the rear portion of the support structure 130 and a second multi-leg strut 146 extends from the lower inner rim 138 to the upper outer rim 132 near the front portion of the support structure 130.

A solid rear wall 135 additionally interconnects the outer rims 132, 136 and the respective inner rims 134, 138 along the rear end area as well as further connecting the upper and lower structures together. The solid rear wall 135 defines the holes 125, 127, 128 and the slot 129. Recessed areas 139 on the upper and lower sides of the rear wall 135 define receiving areas for porous structure, as seen in FIGS. 20-24. Cross members 131 in this area along with contours of the outer rims 132, 136 define the serrations 126. A solid front wall 140 with a concave configuration also interconnects the outer rims 132, 136 and the respective inner rims 134, 138 along the front end area. The front wall 140 includes an upper sloped portion 142 extending between the upper outer rim 132 and inner rim 134 and a lower sloped portion 143 extending between the lower outer rim 136 and inner rim 138. While the rims and walls are described as specific elements for clarity, it is understood that the elements are formed as a unitary structure and may be formed as a smooth structure without any distinction between the elements.

In the illustrations of the support structure 130 in FIGS. 25-27, it is seen that there is significant open space between the upper rims 132, 134 and the lower rims 136, 138 with only the struts 144, 146 therebetween. Additionally, there is open space between the inside surface of the front wall 140 and the inner rims 134, 138. Furthermore, there is open space on an inside surface and the recesses 139, 141 of the rear wall 135. As illustrated in FIGS. 20-24, in the implant 110, these open spaces are filled with the porous structure 150 such that the porous structure 150 encapsulates the struts 144, 146 and extends from the upper surface 120 to the lower surface 122 and from the outer perimeter OP to the inner perimeter IP. In the illustrated embodiment, the porous structure 150 substantially defines the inner perimeter IP and defines a substantial portion of the side walls 116, 118 along the outer perimeter OP.

Referring now to FIGS. 28-34, an ALIF implant 110' in accordance with another embodiment of the disclosure will be described. The implant 110' is similar to the previous embodiment except for slight modification in the structure of the support structure 130' and a corresponding modification in the porous structure 150'. Compared to the previous embodiment, the upper and lower surfaces 120', 122' of the present implant 110' are angled relative to one another. Additionally, the rear wall 135' has a narrower width with a portion of the rear end 114' having an open support structure into which the porous structure 150' extends. With the narrower width, the recess portions 139' open directly into the open space of the side walls 116', 118' and rear end 114'. The rear wall 135' defines a single opening 128' for receipt of an insertion tool. A cylinder 145 is positioned between the upper rims 132, 136 and the lower rims 134, 138 along the rear end 114'. The cylinder 145 defines a through bore 147 configured to also receive an insertion tool. To maintain sufficient implant strength in the rear end 114', a first X-shaped strut 148 extends between the cylinder 145 and the end wall 135' and a second X-shaped strut 148' is positioned on the opposite side of the rear wall 135. The front end 112 of the implant 110' includes a recessed area 141 which defines a forward serration 149. Again, in the implant 110', the open spaces are filled with the porous structure 150' such that the porous structure 150' encapsulates the struts 144, 146, 114, 148' and extends from the upper surface 120' to the lower surface 122' and from the outer perimeter OP to the inner perimeter IP. In the illustrated embodiment, the porous structure 150' substantially defines the inner perimeter IP and defines a substantial portion of the side walls 116', 118' and a portion of the rear end 114' along the outer perimeter OP.

Figure 35:
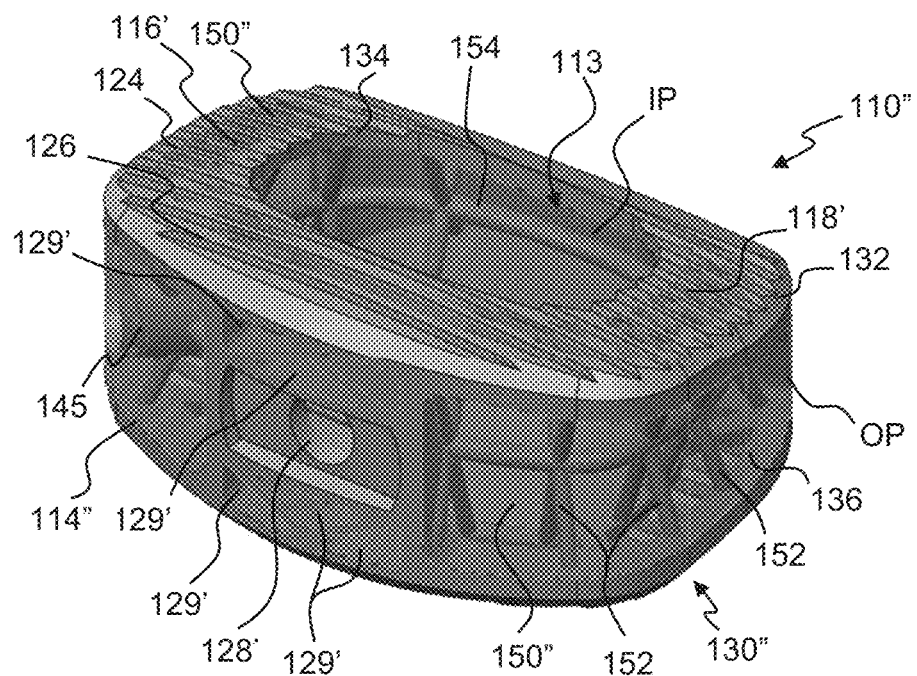
FIGS. 35 and 36 are perspective and side views, respectively, of an intervertebral implant according to another embodiment of the disclosure with the porous portions shown translucently.
Figure 36:
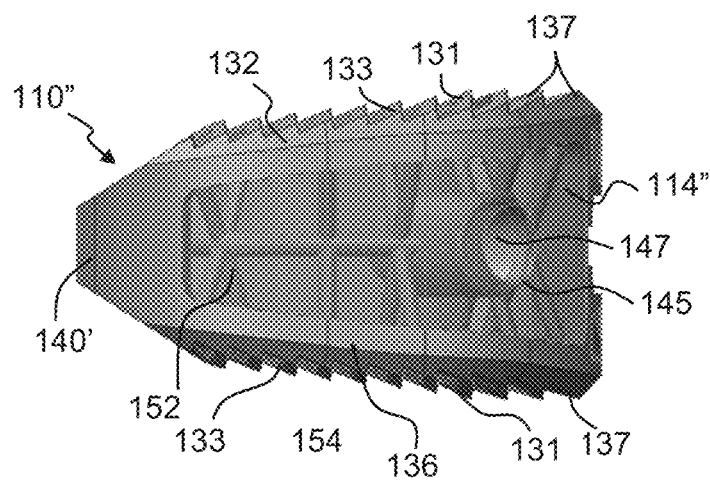

Referring now to FIGS. 35 and 36, an ALIF implant 110" in accordance with another embodiment of the disclosure will be described. The implant 110" is similar to the previous embodiment except for slight modification in the structure of the support structure 130" and a corresponding modification in the porous structure 150". Compared to the previous embodiment, the rear wall 135" of the rear end 114" includes a plurality of slots 129' positioned about the hole 128'. Additionally, the struts of the previous embodiment are replaced with a plurality of X-shaped struts 152 which are interconnected to one another by a circumferential intermediate rim 154. Each of the struts 152 also interconnects with the upper rims 132, 136 and the lower rims 134, 137. Again, in the implant 110", the open spaces are filled with the porous structure 150" such that the porous structure 150" encapsulates the struts 152 and the intermediate rim 154 and extends from the upper surface 120' to the lower surface 122' and from the outer perimeter OP to the inner perimeter IP. In the illustrated embodiment, the porous structure 150" substantially defines the inner perimeter IP and defines a substantial portion of the side walls 116', 118' and a portion of the rear end 114" along the outer perimeter OP.

Figure 37:
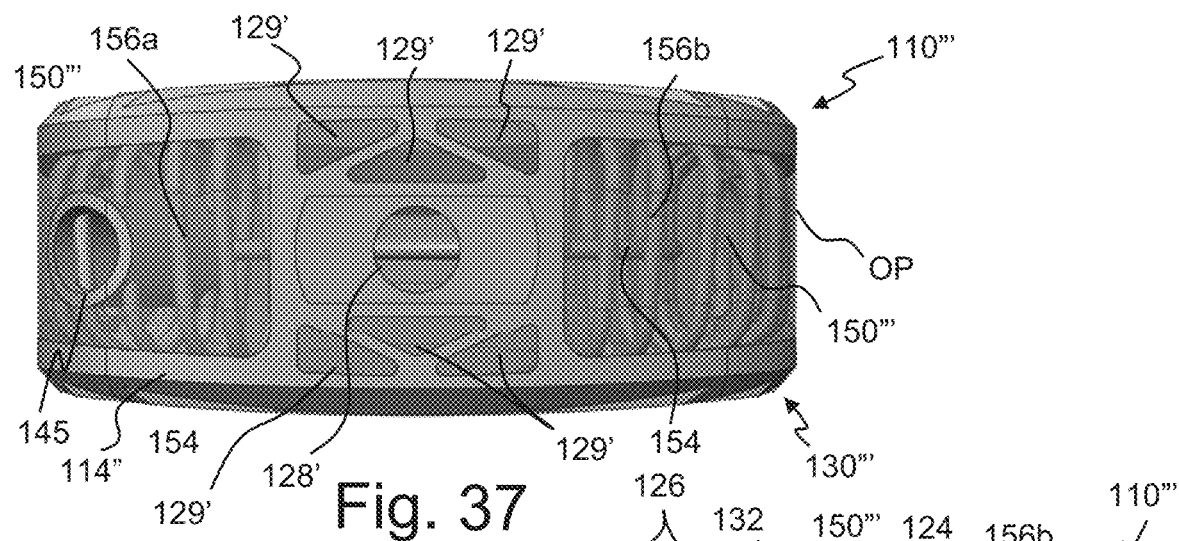
FIGS. 37 and 38 are rear and side views, respectively, of an intervertebral implant according to another embodiment of the disclosure with the porous portions shown translucently.
Figure 38:
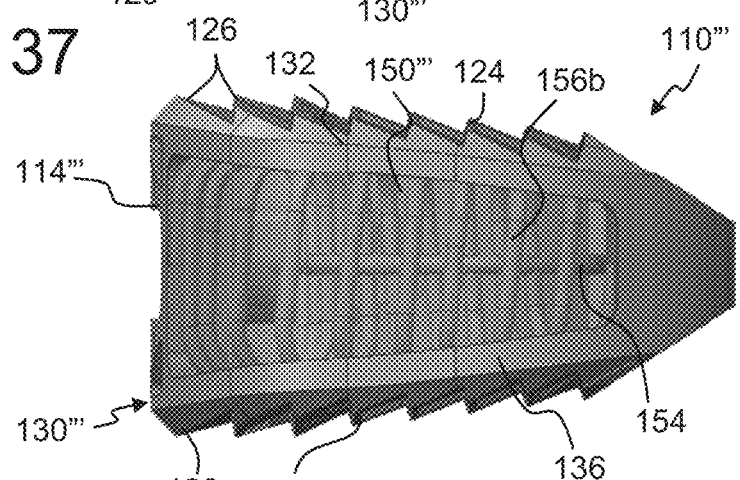

Referring now to FIGS. 37 and 38, an ALIF implant 110''' in accordance with another embodiment of the disclosure will be described. The implant 110''' is similar to the previous embodiment except for slight modification in the structure of the support structure 130" and a corresponding modification in the porous structure 150". Compared to the previous embodiment, the X-shaped struts are replaced by coil struts 156a and 156b. Coil strut 156a of side wall area 118' extends from the rear wall 135" to the front wall 140" and extends about the circumferential intermediate rim 154. Similarly, coil strut 156b of side wall area 116' extends from the rear wall 135" to the front wall 140" and extends about the circumferential intermediate rim 154, however, the cylinder 145 extends through and interconnects with the coil strut 154b. Each of the struts 156a, 156b also interconnects with the upper rims 132, 136 and the lower rims 134, 137. Again, in the implant 110''', the open spaces are filled with the porous structure 150''' such that the porous structure 150''' encapsulates the intermediate rim 154 and struts 156a, 156b and extends from the upper surface 120' to the lower surface 122' and from the outer perimeter OP to the inner perimeter IP. In the illustrated embodiment, the porous structure 150''' substantially defines the inner perimeter IP and defines a substantial portion of the side walls 116', 118' and a portion of the rear end 114" along the outer perimeter OP.

Figure 39:
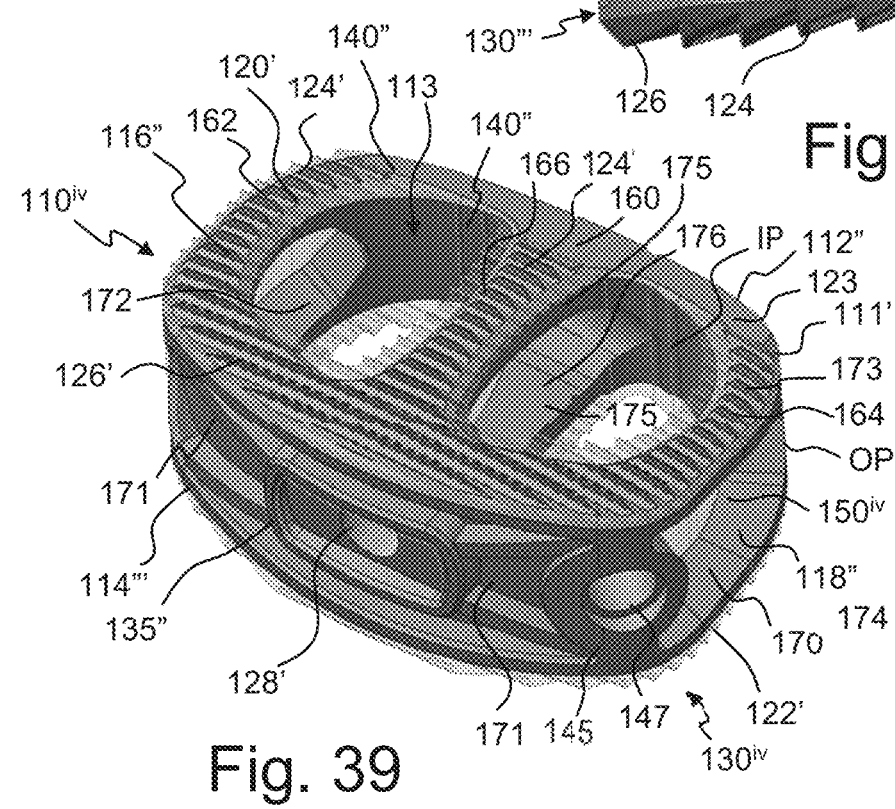
FIG. 39 is a perspective view of an intervertebral implant according to another embodiment of the disclosure with the porous portions shown translucently.

Referring now to FIG. 39, an ALIF implant 110$^{iv}$ in accordance with another embodiment of the disclosure will be described. The implant 110$^{iv}$ has a body 111' with a generally oval configuration. The body 111' is defined by a tapered front end 112", a rectangular rear end 114''' and side walls 116" and 118" extending therebetween. The implant 110$^{iv}$ has an outer perimeter OP extending about the body 111'. A hollow interior chamber 113 is defined within an inner perimeter IP of the body 111'. The hollow interior chamber 113 is configured to receive bone growth promoting materials. The implant 110$^{iv}$ has an upper surface 120' and a substantially parallel lower surface 122', with both surfaces having a tapering portion 123 at the front end 112. In the present embodiment, each of the surfaces 120', 122' includes a central surface portion 175. The upper and lower surfaces 120', 122' define a plurality of serrations 124' along the side walls 116, 118 and the central portions 175 and a plurality of serrations 126' along the rear end 114'''. The rear end 114''' of the implant 110 includes a plurality of holes 128", 145 configured for receiving an instrument that is used for inserting the implant 110. As in the previous embodiments, the implant 110$^{iv}$ is defined by a solid support structure 130$^{iv}$ with an interfiled, integral porous structure 150$^{iv}$.

The solid support structure 130$^{iv}$ includes an upper plate 160 extending from the front end 112" to the rear end 114''' and defining side wall portions 162, 164 and central portion 166. A plurality of recesses 173 in the upper and lower plates 160, 170 are filled with the porous structure 150$^{iv}$ to define the serrations 124', 126'. Similarly, a lower plate 170 extends from the front end 112" to the rear end 114''' and defines side wall portions 172, 174 and central portion 176. The upper and lower plates 160, 170 are interconnected by a front wall 140" and a rear wall 135". It is noted that in the present embodiment, the side walls 116', 118' are generally open without any support structure and completely filled with the porous structure 150$^{iv}$. The rear wall 135" defines the holes 128", 145. The rear wall 135" includes a plurality of recesses 171 configured to receive the porous structure 150$^{iv}$. As in the previous embodiments, the porous structure 150$^{iv}$ generally extends from the upper surface 120' to the lower surface 122' and from the outer perimeter OP to the inner perimeter IP. In the illustrated embodiment, the porous structure 150$^{iv}$ substantially defines the inner perimeter IP and defines a substantial portion of the side walls 116', 118' along the outer perimeter OP.

Figure 160:
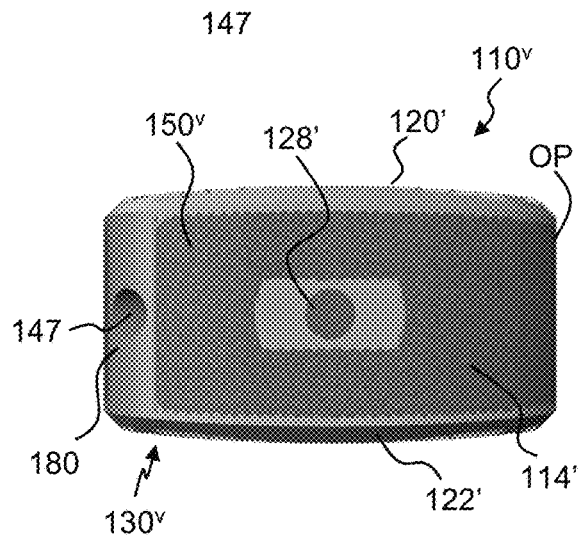
Figure 161:
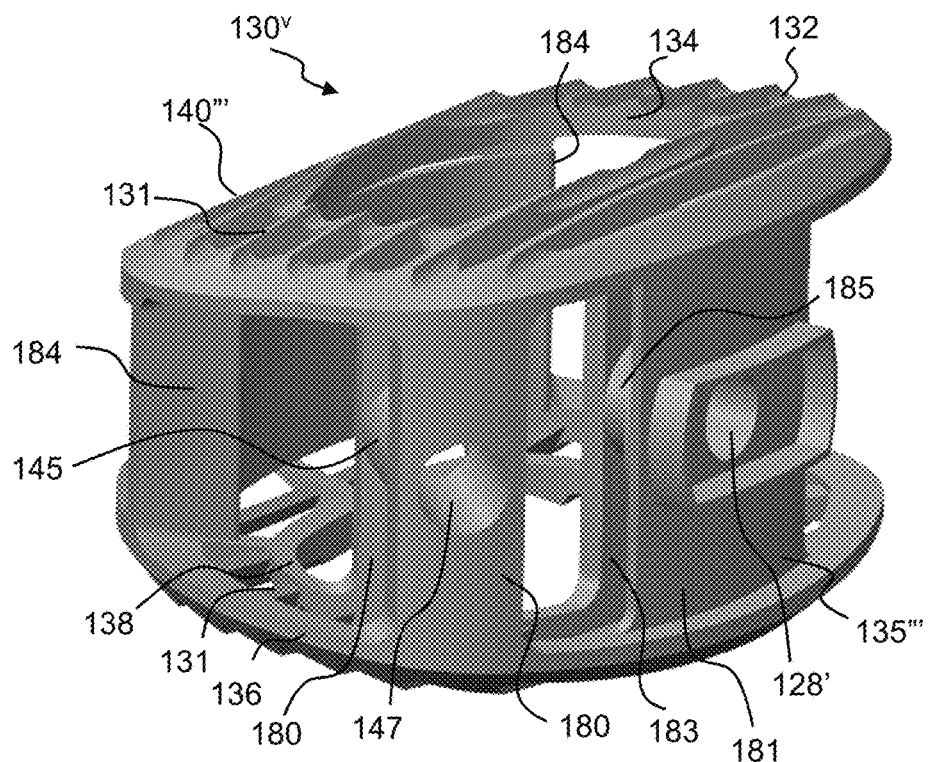
FIGS. 161-163 are perspective, top and side views, respectively, of the intervertebral implant of FIGS. 157-160 with the porous portions removed to show the support structure.
Figure 162:
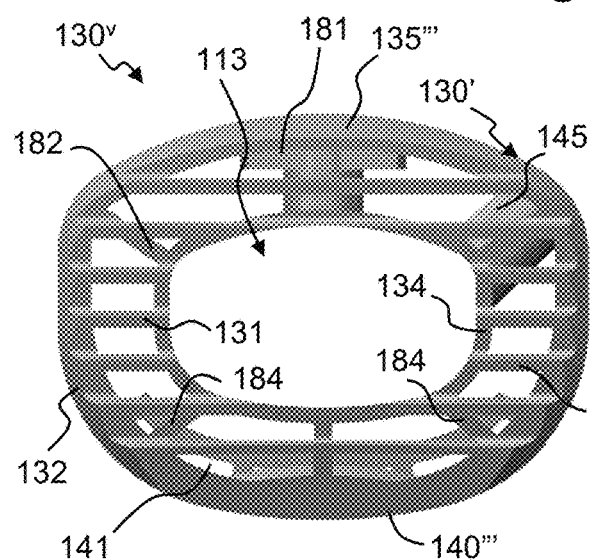
Figure 163:
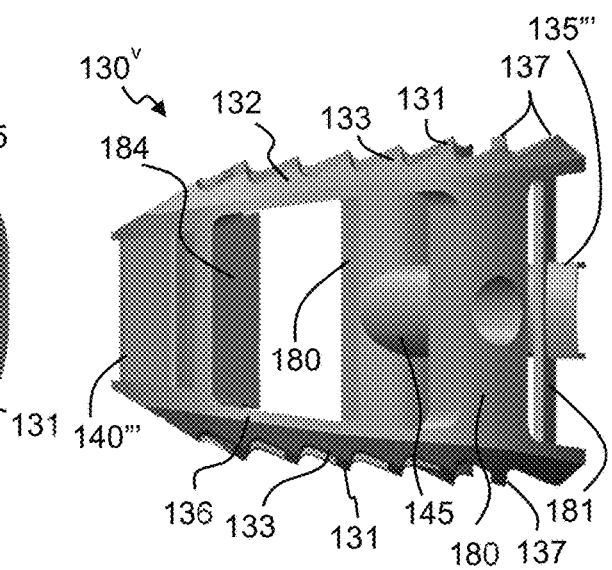
Figure 164:
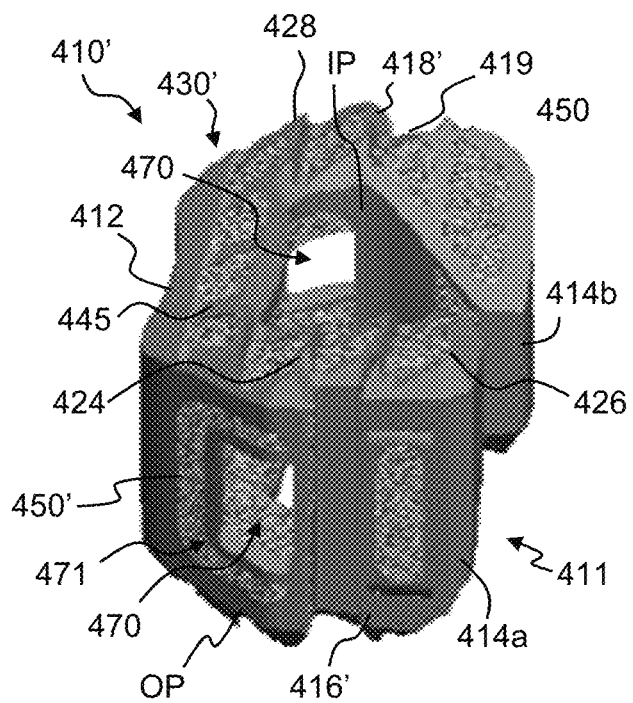
FIGS. 164-166 are perspective top and side views, respectively, of another embodiment of a spacer portion of the implants of FIGS. 76-79 with the porous portions shown textured.
Figures 165, 166:
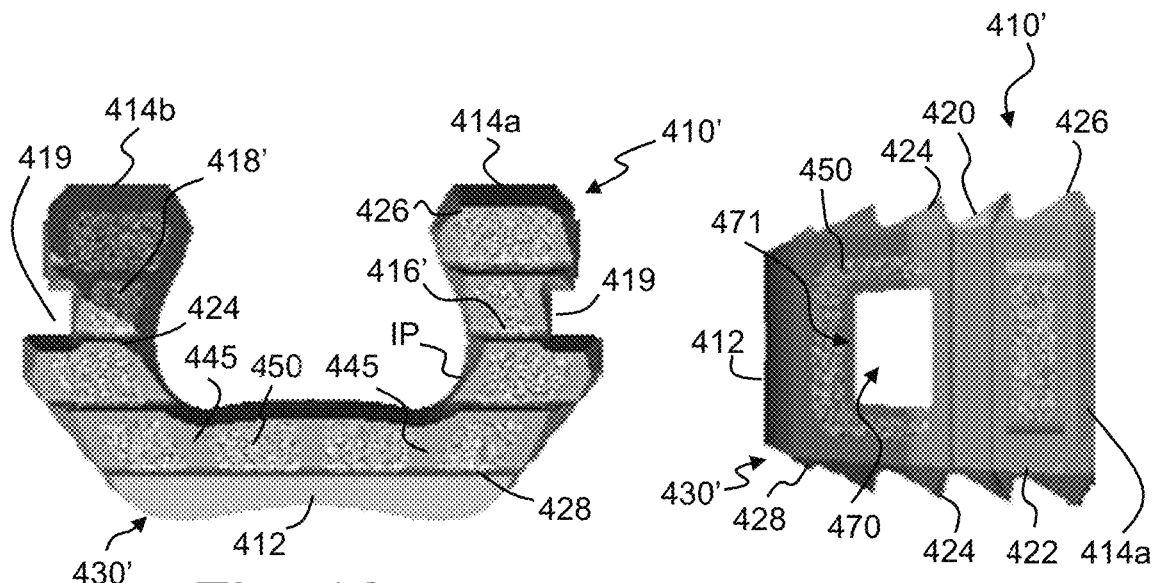
Figure 167:
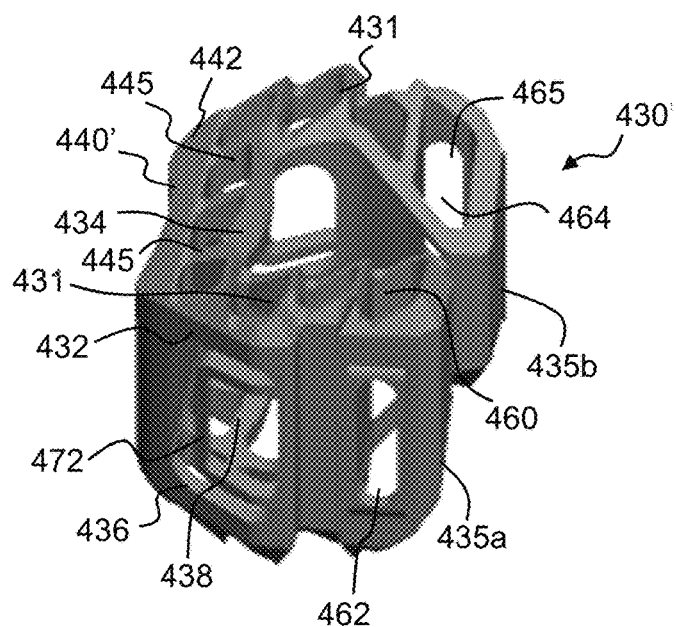
FIGS. 167-169 are perspective, top and side views, respectively, of the spacer portion of FIGS. 164-166 with the porous portions removed to show the support structure.
Figure 168:
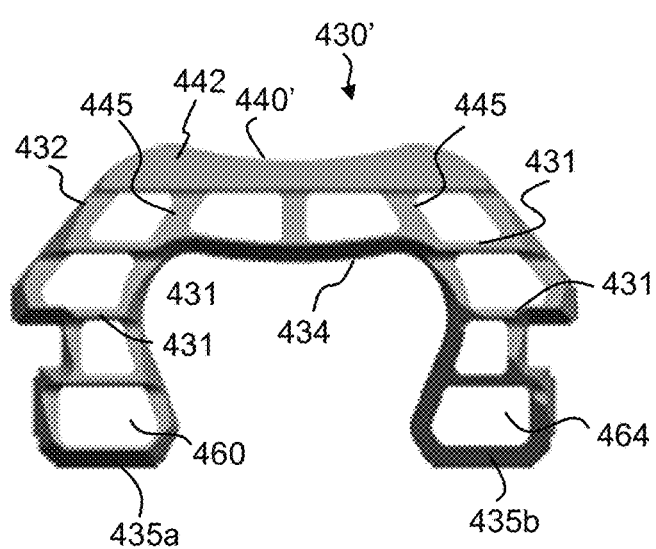
Figure 169:
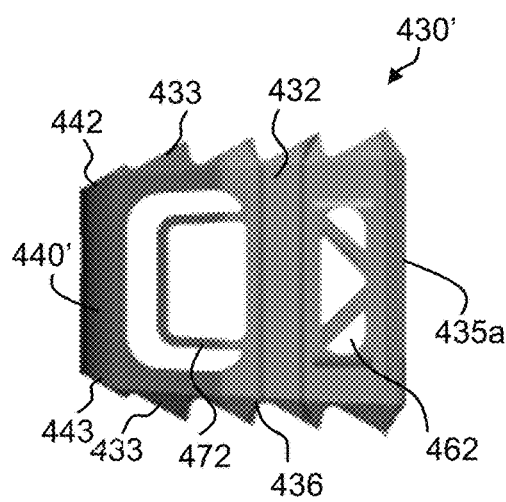

Referring now to FIGS. 157-163, an ALIF implant 110$^v$ in accordance with another embodiment of the disclosure will be described. The implant 110$^v$ is similar to the embodiment illustrated in FIGS. 28-34 except for slight modification in the structure of the support structure 130$^v$ and a corresponding modification in the porous structure 150$^v$. The support structure 130$^v$ of the present embodiment has a taller configuration such that a pair of walls 180 extend between the upper rims 132, 136 and the lower rims 134, 138 along the rear end 114' to support the cylinder 145. Additionally, the rear wall 135''' includes a pair of walls 181, 183 which support the insertion tool opening 128'. The rearward wall 181 is radially inward such that porous structure 150$^v$ extends along a substantial portion of the rear end 114' of the implant 110$^v$ as shown in FIG. 160. To provide additional support in the rear wall 135''', an additional angled wall 182 extends between the upper rims 132, 136 and the lower rims 134, 138 on the side of the rear end 114' opposite the cylinder 145. With this configuration, the rear wall 135''' provides necessary support but leaves significant open space for the porous structure as shown in FIG. 161.

In the present embodiment, the side walls 116''', 118''' are free of support structure between the upper rims 132, 136 and the lower rims 134, 138 from the rear wall 135''' to the front wall 140'''. For additional support, an angled wall 184 extends between the upper rims 132, 136 and the lower rims 134, 138 at each lateral end of the front wall 140'''. As such, side wall 116''' is free of vertical support structure between the walls 180 and the angled wall 184 and side wall 118''' is free of vertical support structure between the rear angled wall 182 and the front angled wall 184.

Again, in the implant 110$^v$, the open spaces are filled with the porous structure 150$^v$ such that the porous structure 150$^v$ extends from the upper surface 120' to the lower surface 122' and from the outer perimeter OP to the inner perimeter IP. In the illustrated embodiment, the porous structure 150$^v$ substantially defines the inner perimeter IP and defines a substantial portion of the side walls 116''', 118''' and the rear end 114' along the outer perimeter OP.

Referring now to FIGS. 40-47, one embodiment of a transforaminal lumbar interbody fusion (TLIF) implant 210 will be described. As illustrated, the implant 210 has a body 211 with a generally rectangular shape. The body 211 is defined by a tapered front end 212, a rectangular rear end 214 and side walls 216 and 218 extending therebetween. The implant 210 has an outer perimeter OP extending about the body 211. A hollow interior chamber 213 is defined within an inner perimeter IP of the body 211. The hollow interior chamber 213 is configured to receive bone growth promoting materials. The implant 210 has an upper surface 220 and a substantially parallel lower surface 222, with both surfaces having a tapering portion 223 at the front end 212. The upper and lower surfaces 220, 222 define a plurality of serrations 224 along the side walls 216, 218 and a plurality of serrations 226 along the rear end 214. The rear end 214 of the implant 210 includes a hole 225 and a pair of slots 227 for receiving an instrument that is used for inserting the implant 210. The implant 210 is defined by a solid support structure 230 with an interfiled, integral porous structure 250.

The solid support structure 230 includes an outer rim 232 extending about the outer perimeter OP of the upper surface 220 and an inner rim 234 extending about the inner perimeter IP of the upper surface 220, i.e. about the interior chamber 213. Similarly, an outer rim 236 extends about the outer perimeter OP of the lower surface 222 and an inner rim 238 extends about the inner perimeter IP of the lower surface 222. A plurality of cross struts 231 extend between the outer rims 232, 236 and the respective inner rims 234, 238 along the side wall areas. As seen in the figures, the cross struts 231 along with contoured portions 233 of the rims 232, 234, 236, 238 define the contour of the serrations 224. In addition to interconnecting the rims within a given upper or lower surface, external radial struts 260, 262 additionally interconnect the rims 232, 234, 236, 238. Outer radial struts 260 extend along each of the side walls 216, 218 along the outer perimeter OP. The outer radial struts 260 have a central portion 261 and legs 263 which extend between the upper and lower outer rims 232 and 236. Inner radial struts 262 extend along each of the side walls 216, 218 along the inner perimeter IP. The inner radial struts 262 have a central portion 265 and legs 267 which extend between the upper and lower inner rims 234 and 238.

A solid rear wall 235 additionally interconnects the outer rims 232, 236 and the respective inner rims 234, 238 along the rear end area as well as further connecting the upper and lower structures together. The solid rear wall 235 defines the hole 225 and slots 227. Recessed areas 239 and 241 on the upper and lower sides of the rear wall 235 define receiving areas for porous structure, as seen in FIGS. 40-43. The contours of the outer rims 232, 236 define the serrations 226. A solid front wall 240 with a concave configuration also interconnects the outer rims 232, 236 and the respective inner rims 234, 238 along the front end area. The front wall 240 includes an upper sloped portion 242 extending between the upper outer rim 232 and inner rim 234 and a lower sloped portion 243 extending between the lower outer rim 236 and inner rim 238. While the rims and walls are described as specific elements for clarity, it is understood that the elements are formed as a unitary structure and may be formed as a smooth structure without any distinction between the elements.

In the illustrations of the support structure 230 in FIGS. 44-47, it is seen that there is significant open space between the upper rims 232, 234 and the lower rims 236, 238, between the inside surface of the front wall 240 and the inner rims 234, 238, and on an inside surface and the recesses 239, 241 of the rear wall 235. As illustrated in FIGS. 40-43, in the implant 210, the open spaces are filled with the porous structure 250 such that it extends from the upper surface 220 to the lower surface 222 and from the outer perimeter OP to the inner perimeter IP. In the present embodiment, the struts 260, 262 are not encapsulated in the porous structure 250, but instead the struts 260 are coplanar with the porous structure 250 along the outer perimeter OP and the struts 262 are coplanar with the porous structure 250 along the inner perimeter IP. Again, the porous structure 250 substantially defines the inner perimeter IP and defines a substantial portion of the side walls 216, 218 along the outer perimeter OP.

Referring now to FIGS. 48-51, a TLIF implant 210' in accordance with another embodiment of the disclosure will be described. The implant 210' is similar to the previous embodiment except for slight modification in the structure of the support structure 230' and a corresponding modification in the porous structure 250'. In the present embodiment, a connecting ring 268 interconnects the central portion 261 with the central portion 265 of the struts 260, 262 in each side wall 216, 218. Additionally, on the upper and lower surfaces 220, 222, additional serrations 229 are provided adjacent the rear end 214'. Again, in the implant 210', the open spaces are filled with the porous structure 250' such that it extends from the upper surface 220 to the lower surface 222 and from the outer perimeter OP to the inner perimeter IP. In the present embodiment the struts 260 are coplanar with the porous structure 250' along the outer perimeter OP and the struts 262 are coplanar with the porous structure 250' along the inner perimeter IP. The connecting rings 268 are encapsulated within the porous structure 250'. Again, the porous structure 250' substantially defines the inner perimeter IP and defines a substantial portion of the side walls 216, 218 along the outer perimeter OP.

Figure 52:
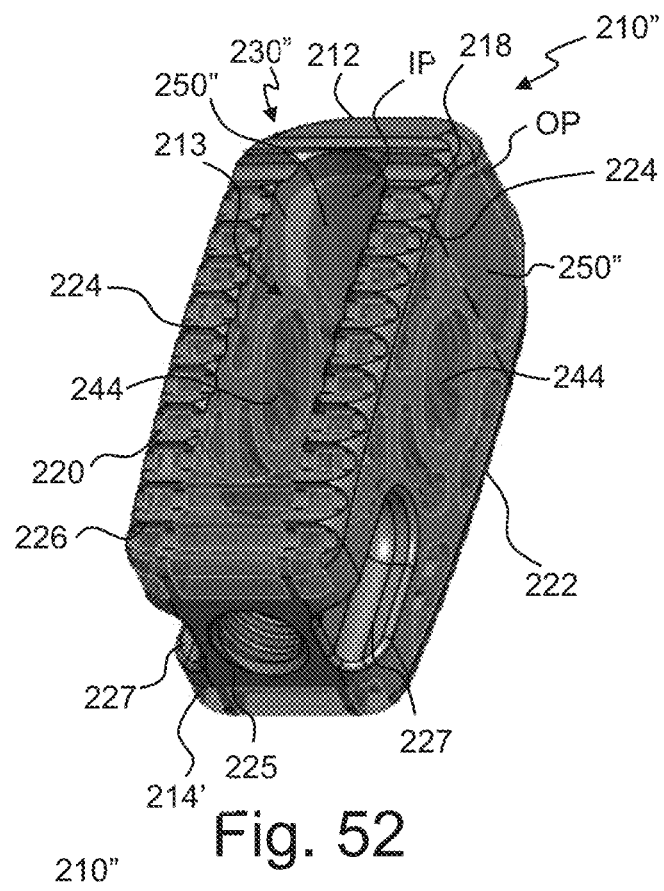
FIGS. 52 and 53 are perspective and side views, respectively, of an intervertebral implant according to another embodiment of the disclosure with the porous portions shown translucently.
Figure 53:
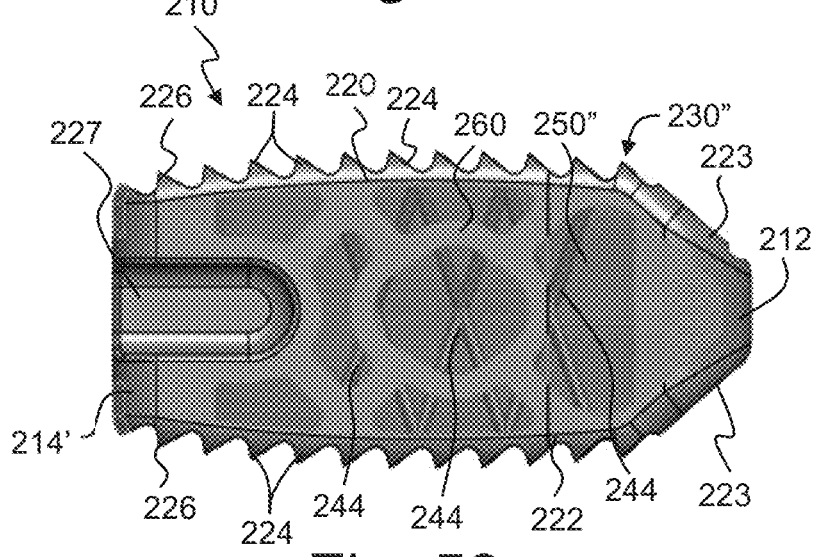
Figure 58:
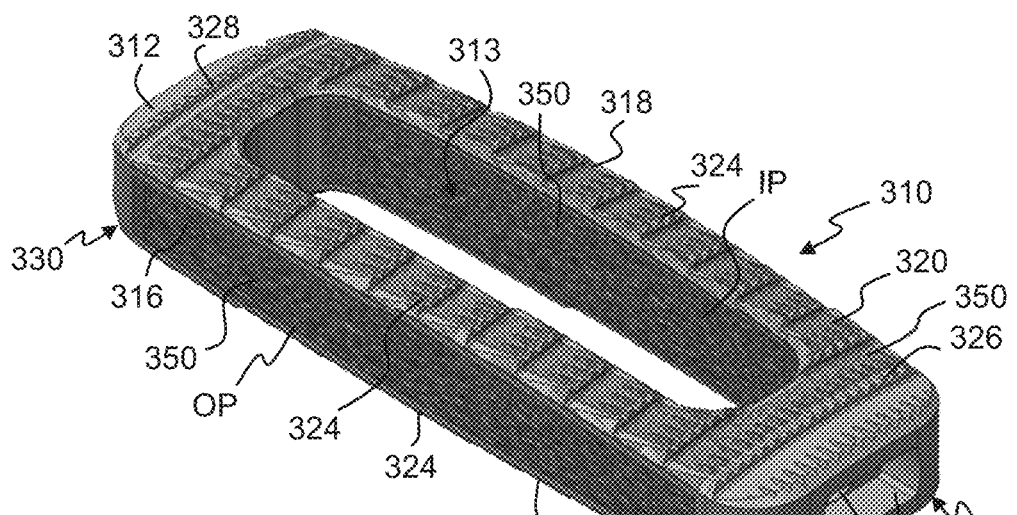
FIGS. 58-61 are perspective, top, side and rear views, respectively, of an intervertebral implant according to another embodiment of the disclosure with the porous portions shown textured.
Figure 59:
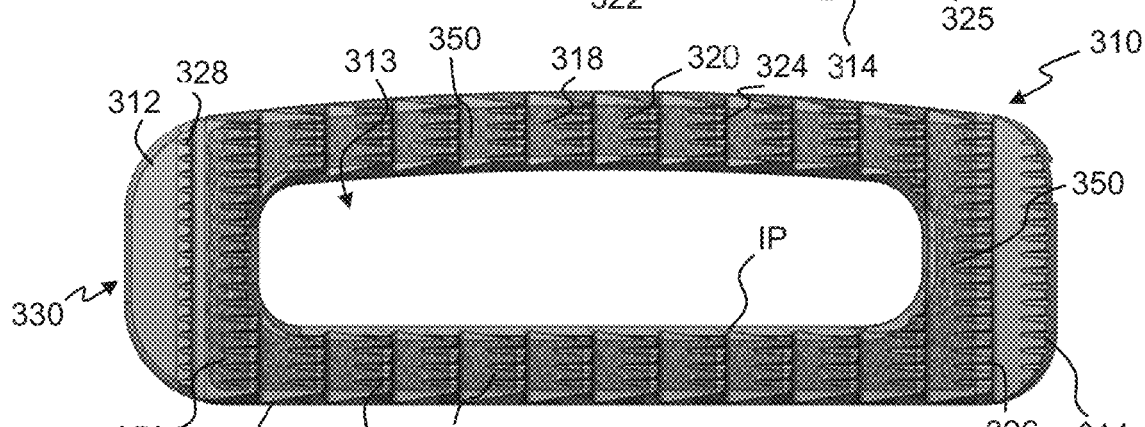
Figure 60:
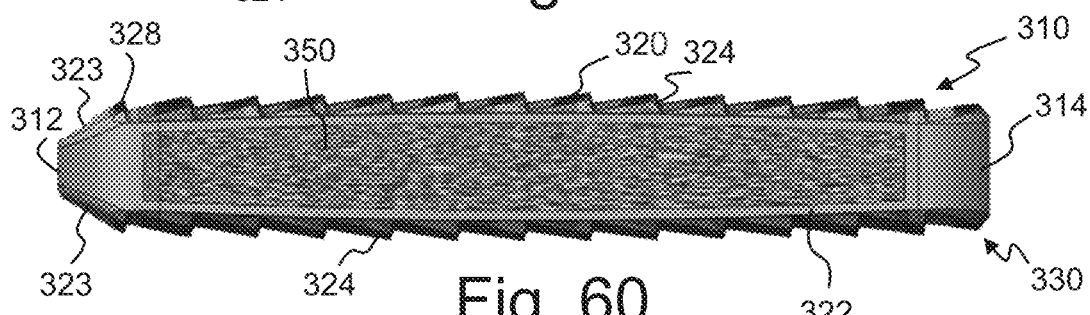
Figure 61:
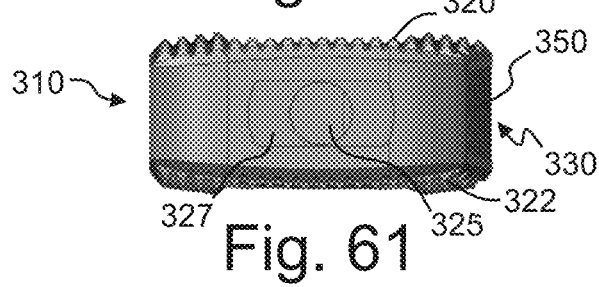

Referring now to FIGS. 52 and 53, a TLIF implant 210" in accordance with another embodiment of the disclosure will be described. The implant 210" is similar to the embodiment illustrated in FIGS. 40-47 except for slight modification in the structure of the support structure 230" and a corresponding modification in the porous structure 250". In the present embodiment, in addition to the struts 260, 262, a plurality of X-shaped struts 244 extend between the upper rims 232, 234 and the lower rims 236, 238 in each side wall 216, 218. Again, in the implant 210", the open spaces are filled with the porous structure 250" such that it extends from the upper surface 220 to the lower surface 222 and from the outer perimeter OP to the inner perimeter IP. In the present embodiment the struts 260 are coplanar with the porous structure 250' along the outer perimeter OP and the struts 262 are coplanar with the porous structure 250' along the inner perimeter IP. The X-shaped struts 244 are encapsulated within the porous structure 250". Again, the porous structure 250" substantially defines the inner perimeter IP and defines a substantial portion of the side walls 216, 218 along the outer perimeter OP.

Referring now to FIGS. 52 and 53, a TLIF implant 210''' in accordance with another embodiment of the disclosure will be described. The implant 210''' is similar to the embodiment illustrated in FIGS. 40-47 except for slight modification in the structure of the support structure 230''' and a corresponding modification in the porous structure 250'''. In the present embodiment, the side walls 216', 218' do not include external struts, but instead include a plurality of X-shaped struts 246 extending between the upper rims 232, 234 and the lower rims 236, 238 in each side wall 216', 218'. Additionally, an intermediate plate 248 interconnects the X-shaped struts 246 within each side wall area. Again, in the implant 210''', the open spaces are filled with the porous structure 250''' such that the porous structure 250''' encapsulates the struts 246 and the intermediate plate 248 and extends from the upper surface 220 to the lower surface 222 and from the outer perimeter OP to the inner perimeter IP. In the illustrated embodiment, the porous structure 250''' substantially defines the inner perimeter IP and defines a substantial portion of the side walls 216', 218' along the outer perimeter OP.

Referring now to FIGS. 58-64, one embodiment of a lateral lumbar interbody fusion (LLIF) implant 310 will be described. As illustrated, the implant 310 has a body 311 with a generally rectangular shape. The body 311 is defined by a tapered front end 312, a rectangular rear end 314 and side walls 316 and 318 extending therebetween. The implant 310 has an outer perimeter OP extending about the body 311. A hollow interior chamber 313 is defined within an inner perimeter IP of the body 311. The hollow interior chamber 313 is configured to receive bone growth promoting materials. The implant 310 has an upper surface 320 and a substantially parallel lower surface 322, with both surfaces having a tapering portion 323 at the front end 312. The upper and lower surfaces 320, 322 define a plurality of serrations 324 along the side walls 316, 318, a serration 328 along the front end 312 and a plurality of serrations 326 along the rear end 314. The illustrated serrations 324, 326, 328 have micro serrations defined thereon. The rear end 314 of the implant 310 includes a hole 325 surrounded by a slot 327 for receiving an instrument that is used for inserting the implant 310. The implant 310 is defined by a solid support structure 330 with an interfiled, integral porous structure 350.

Figure 62:
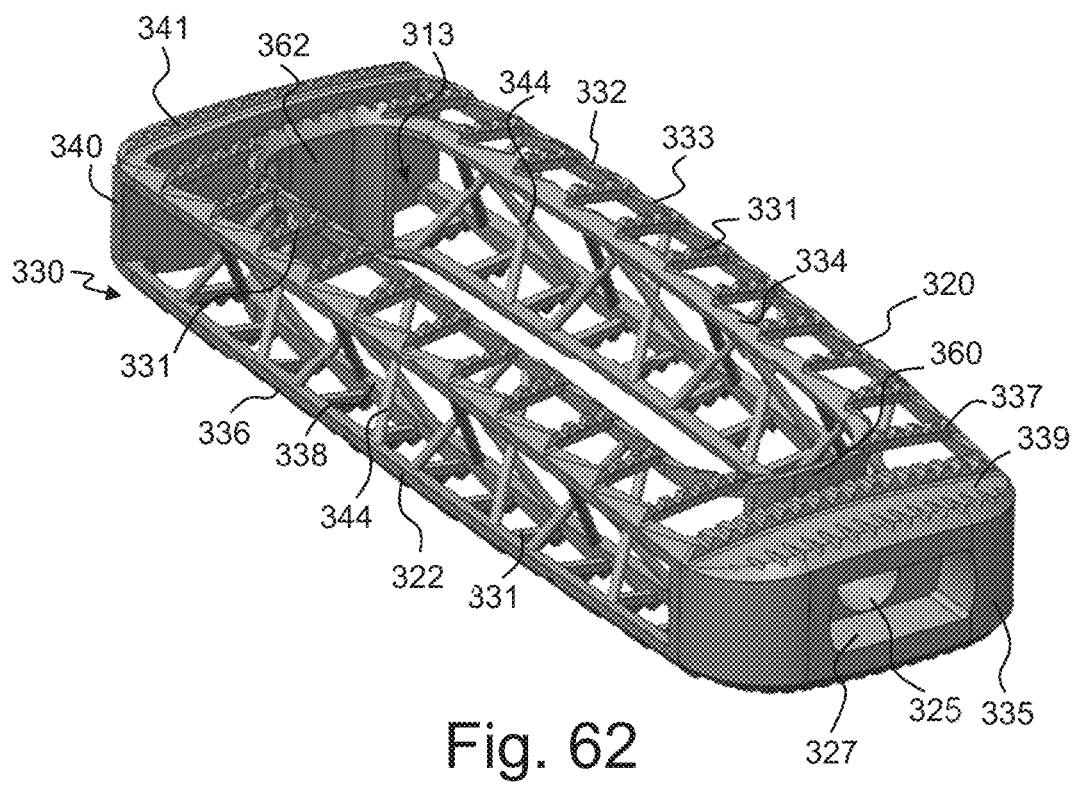
FIGS. 62-64 are perspective, top and side views, respectively, of the intervertebral implant of FIGS. 58-61 with the porous portions removed to show the support structure.
Figure 63:
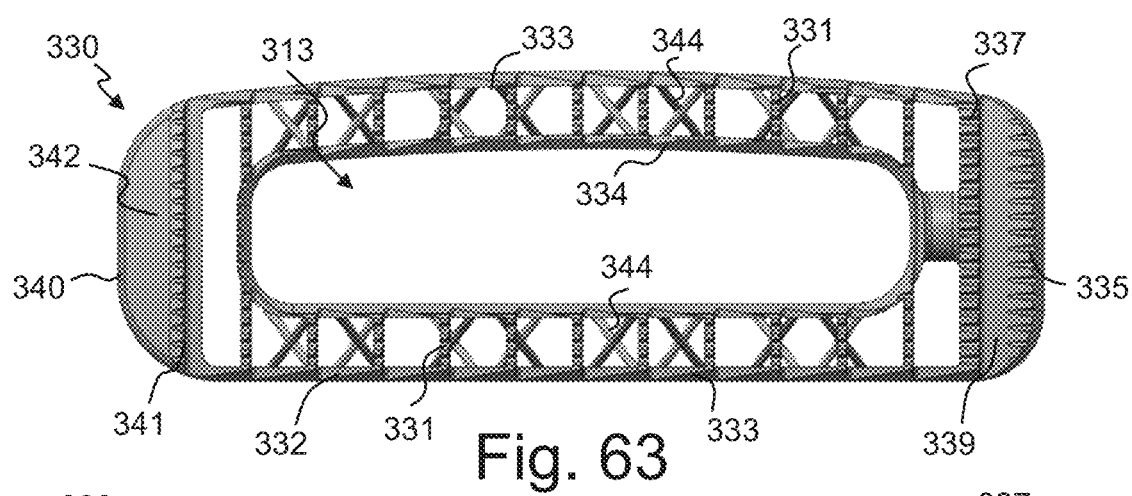
Figure 64:
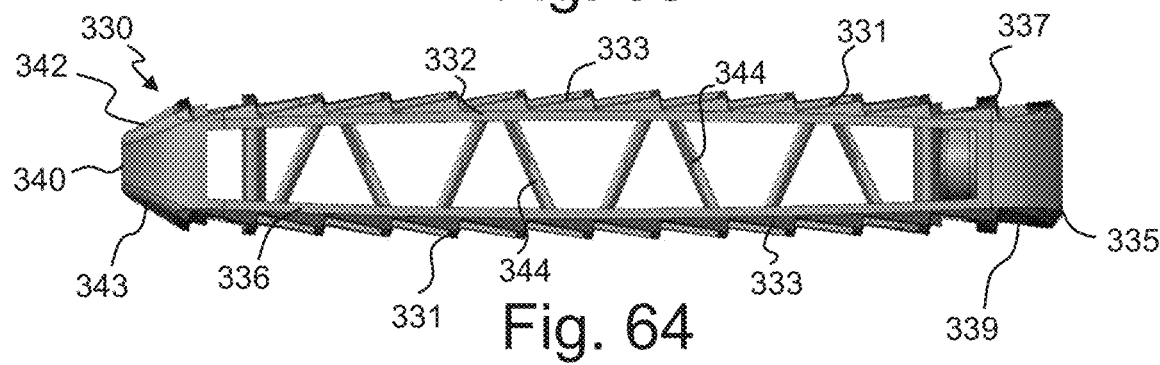

Referring to FIGS. 62-64, the solid support structure 330 includes an outer rim 332 extending about the outer perimeter OP of the upper surface 320 and an inner rim 334 extending about the inner perimeter IP of the upper surface 320, i.e. about the interior chamber 313. Similarly, an outer rim 336 extends about the outer perimeter OP of the lower surface 322 and an inner rim 338 extends about the inner perimeter IP of the lower surface 322. A plurality of cross struts 331 extend between the outer rims 332, 336 and the respective inner rims 334, 338 along the side wall areas. As seen in the figures, the cross struts 331 along with contoured portions 333 of the rims 332, 334, 336, 338 define the contour of the serrations 324. In addition to interconnecting the rims within a given upper or lower surface, a plurality of X-shaped struts 344 extend within each side wall area to interconnect the upper rims 332, 334 with the lower rims 336, 338.

A solid rear wall 335 additionally interconnects the outer rims 332, 336 and the respective inner rims 334, 338 along the rear end area as well as further connecting the upper and lower structures together. The solid rear wall 335 defines the hole 325 and slot 327. A portion of the rear wall 335 defining the hole 325 extends to a secondary rear wall 360 which extends between the upper and lower inner rims 334, 338. A cross strut 339 on the upper and lower sides of the rear wall 335 and a portion of the rear wall 335 define the serrations 326. A solid front wall 340 also interconnects the outer rims 332, 336 and a secondary front wall 362 interconnects the inner rims 334, 338 along the front end area. The front wall 340 includes an upper sloped portion 342 extending between the upper outer rim 332 and inner rim 334 and a lower sloped portion 343 extending between the lower outer rim 336 and inner rim 338. While the rims and walls are described as specific elements for clarity, it is understood that the elements are formed as a unitary structure and may be formed as a smooth structure without any distinction between the elements. A portion of the front wall 341 defines the serration 328.

In the illustrations of the support structure 330 in FIGS. 62-64, it is seen that there is significant open space between the upper rims 332, 334 and the lower rims 336, 338, between the inside surface of the front wall 340 and the secondary wall 362 and on an inside surface of the rear wall 335. As illustrated in FIGS. 58-61, in the implant 310, the open spaces are filled with the porous structure 350 such that it encapsulates the struts 344 and extends from the upper surface 320 to the lower surface 322 and from the outer perimeter OP to the inner perimeter IP. In the illustrated embodiment, the porous structure 350 substantially defines the inner perimeter IP and defines a substantial portion of the side walls 316, 318 along the outer perimeter OP.

Figure 65:
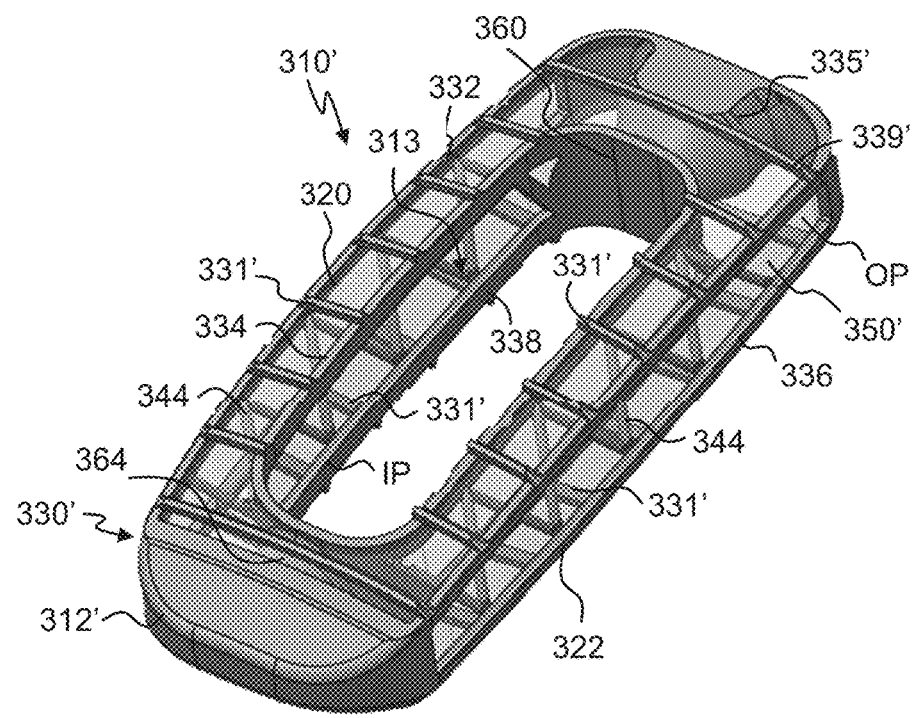
FIGS. 65-67 are perspective, top and side views, respectively, of an intervertebral implant according to another embodiment of the disclosure with the porous portions shown translucently.
Figure 66:
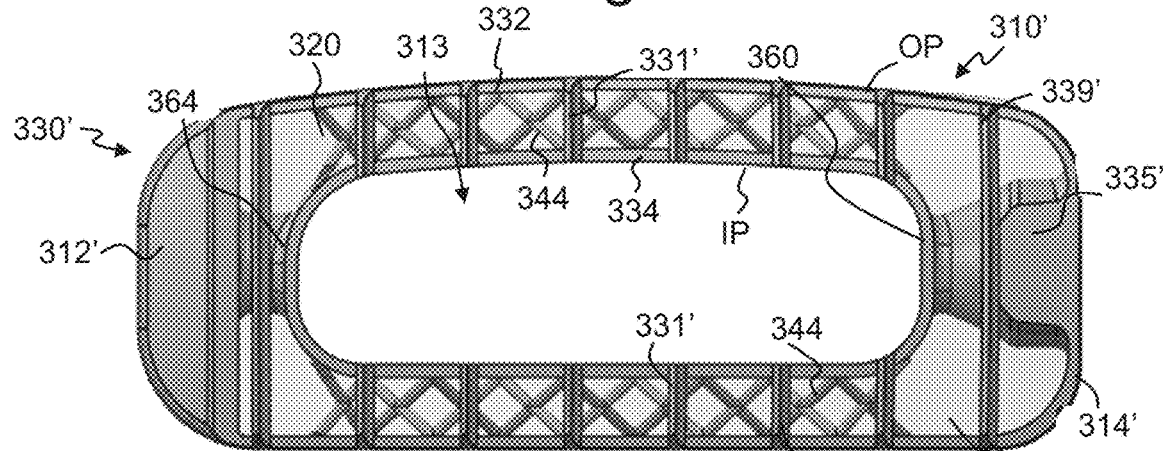
Figure 67:
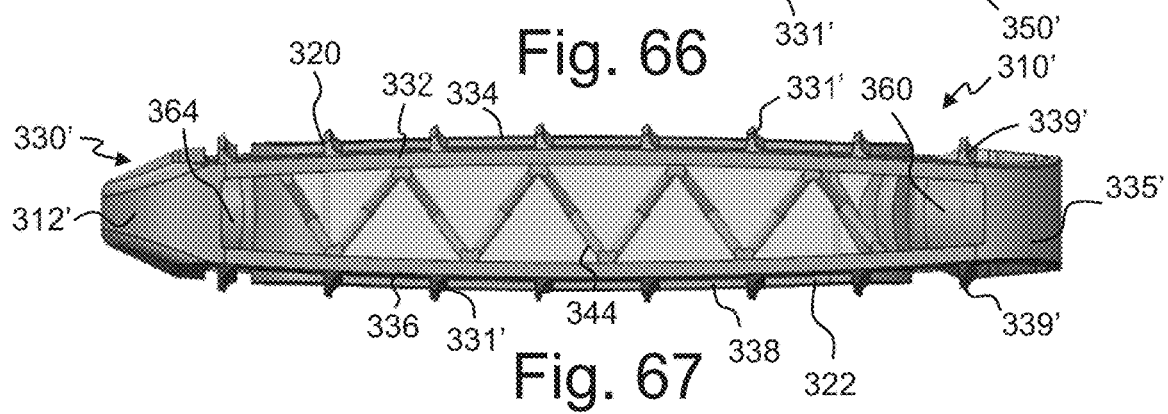

Referring now to FIGS. 65-67, an LLIF implant 310' in accordance with another embodiment of the disclosure will be described. The implant 310' is similar to the previous embodiment except for slight modification in the structure of the support structure 330' and a corresponding modification in the porous structure 350'. Compared to the previous embodiment, the cross struts 331' and 339' do not include mini-serrations. Additionally, the rear wall 335' has a narrower width with a portion of the rear end 314' having an open support structure into which the porous structure 350' extends. The front end 312 of the implant 310' includes a cylindrical portion 364 extending between the front wall 340 and the secondary front wall 362. Again, in the implant 310', the open spaces are filled with the porous structure 350' such that the porous structure 350' encapsulates the struts 344 and extends from the upper surface 320 to the lower surface 322 and from the outer perimeter OP to the inner perimeter IP. In the illustrated embodiment, the porous structure 350' substantially defines the inner perimeter IP and defines a substantial portion of the side walls 316', 318' along the outer perimeter OP.

Figure 68:
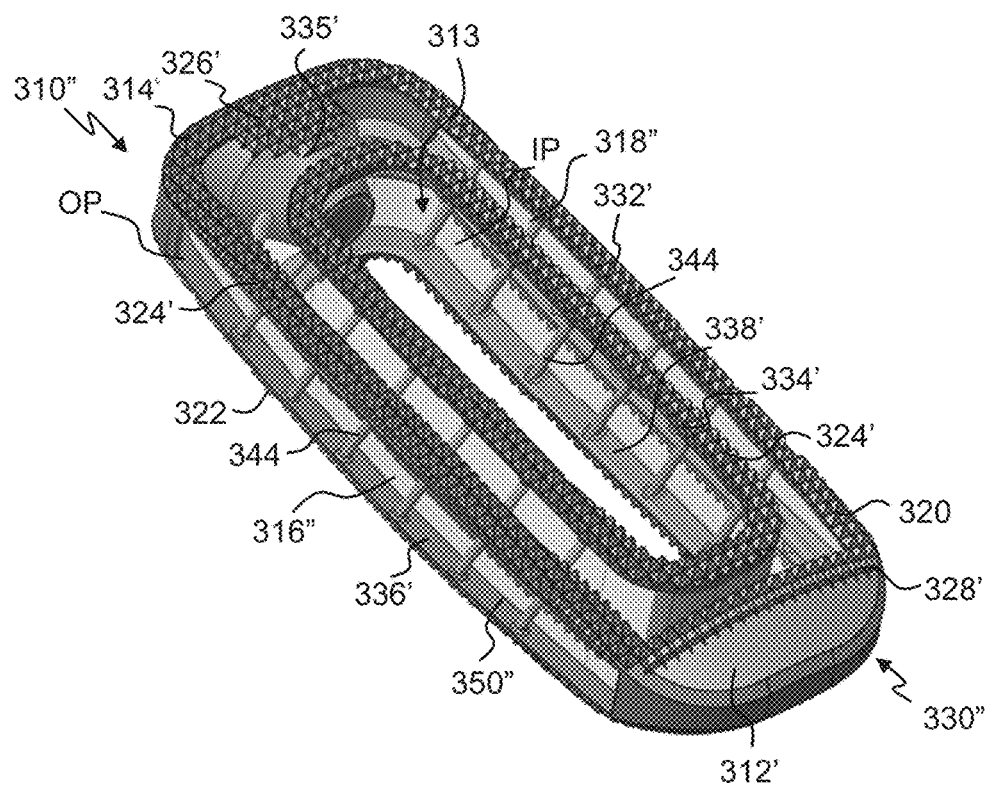
FIGS. 68 and 69 are perspective and side views, respectively, of an intervertebral implant according to another embodiment of the disclosure with the porous portions shown translucently.
Figure 69:
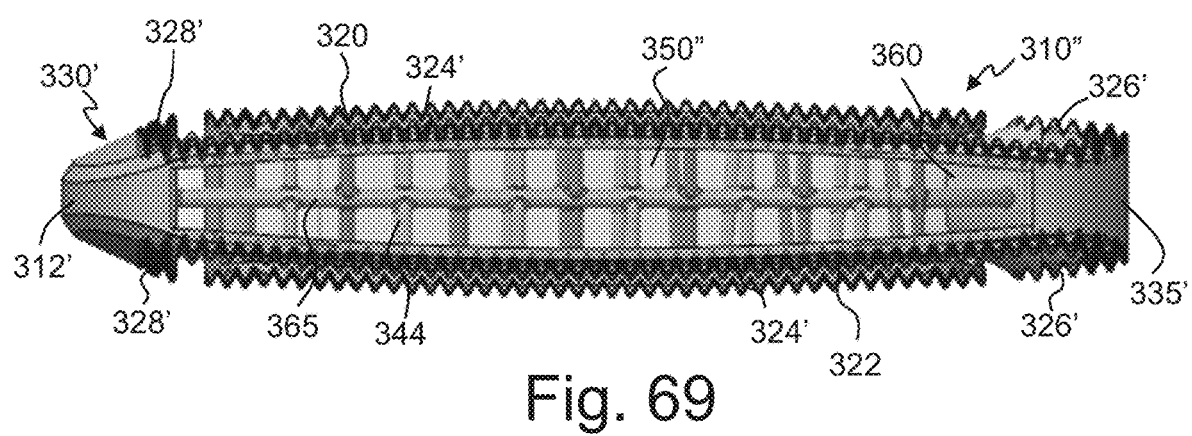

Referring now to FIGS. 68 and 69, an LLIF implant 310" in accordance with another embodiment of the disclosure will be described. The implant 310" is similar to the previous embodiment except for slight modification in the structure of the support structure 330" and a corresponding modification in the porous structure 350". Compared to the previous embodiment, the upper rims 332', 334' and lower rims 336', 338' each have a wider configuration and do not have cross struts extending therebetween. The serrations 324', 326', 328' are formed directly on the rims 332', 334', 336', 338', on the rear wall 335' and the front wall 340'. Additionally, the struts 344 are interconnected to one another by a circumferential intermediate rim 365. Again, in the implant 310", the open spaces are filled with the porous structure 350" such that the porous structure 350" encapsulates the struts 344 and intermediate rim 365 and extends from the upper surface 320 to the lower surface 322 and from the outer perimeter OP to the inner perimeter IP. In the illustrated embodiment, the porous structure 350" substantially defines the inner perimeter IP and defines a substantial portion of the side walls 316", 318" along the outer perimeter OP.

Figure 70:
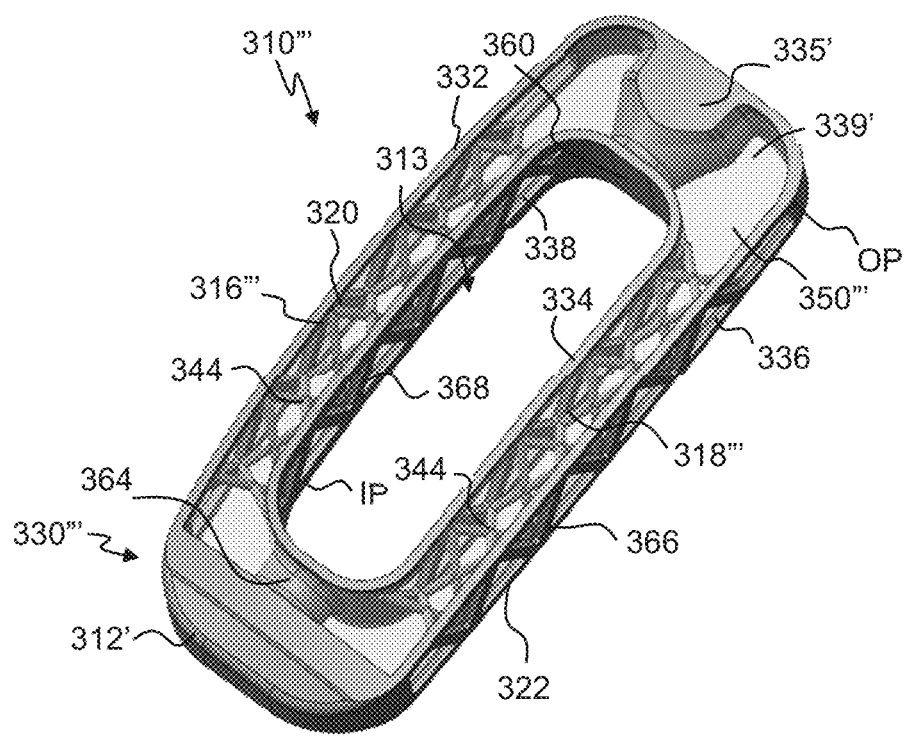
FIGS. 70-72 are perspective, top and side views, respectively, of an intervertebral implant according to another embodiment of the disclosure with the porous portions shown translucently.
Figure 71:
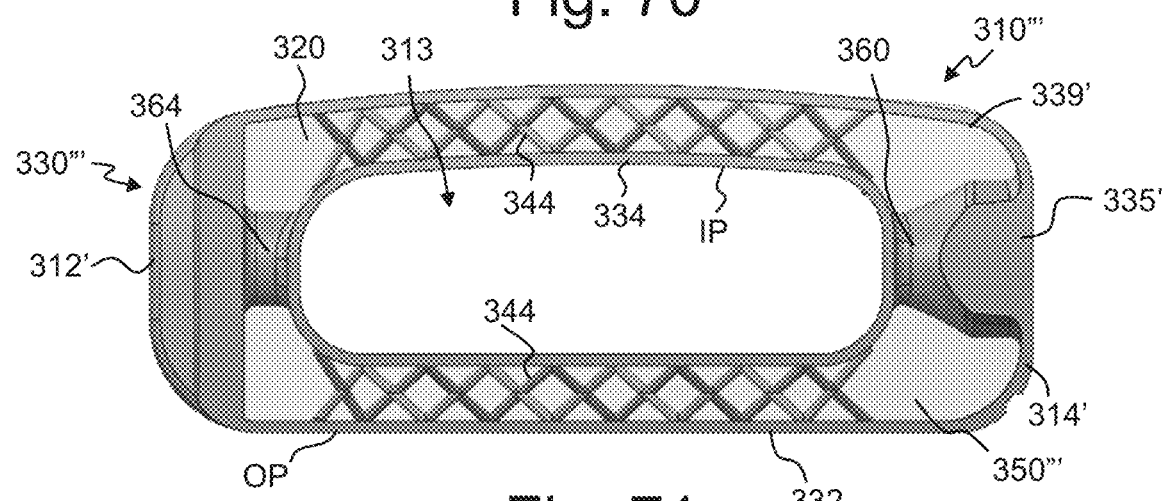
Figure 72:
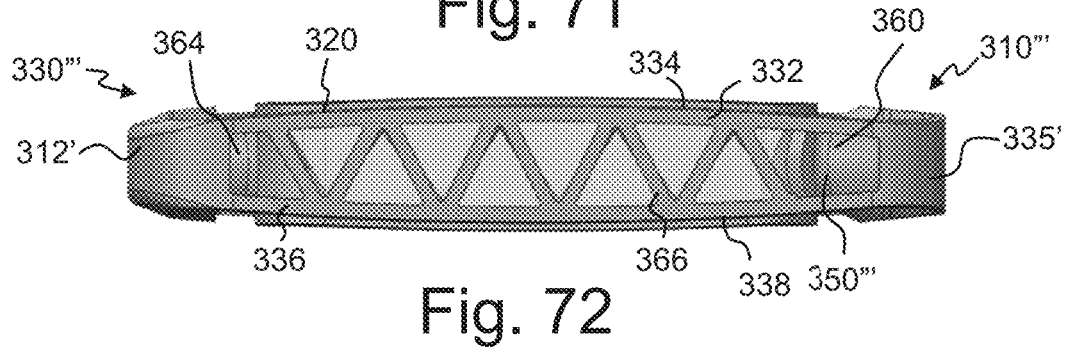
Figures 76, 77:
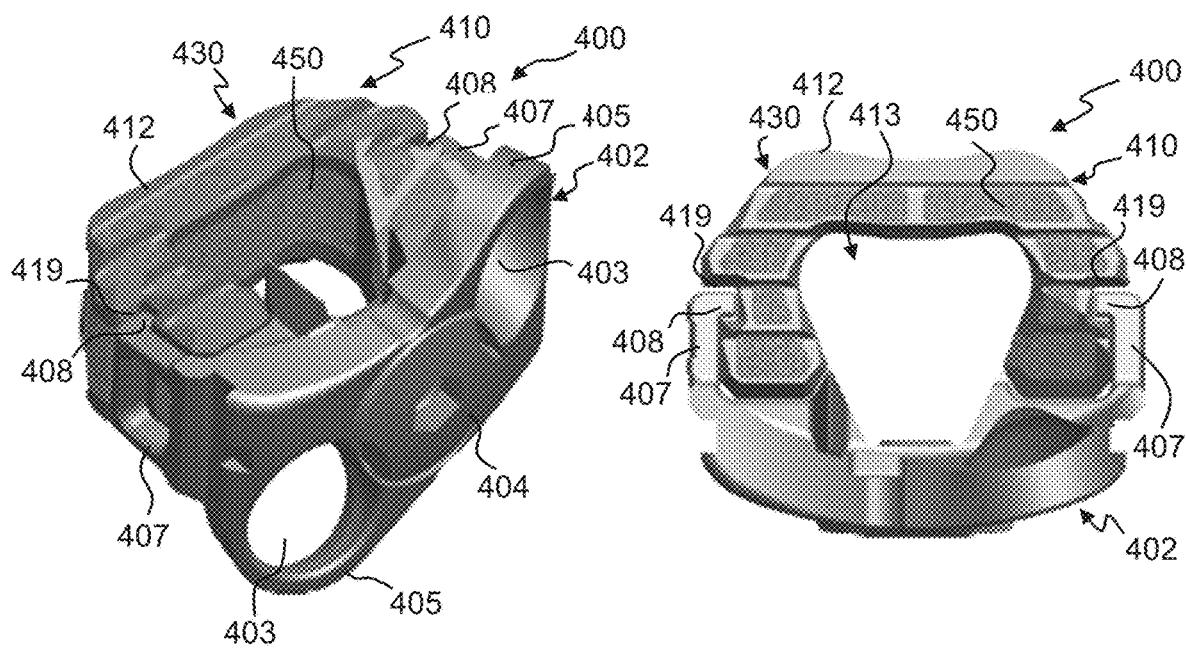
FIGS. 76 and 77 are perspective and top views, respectively, of an intervertebral implant according to another embodiment of the disclosure with the porous portions shown textured.
Figures 78, 79:
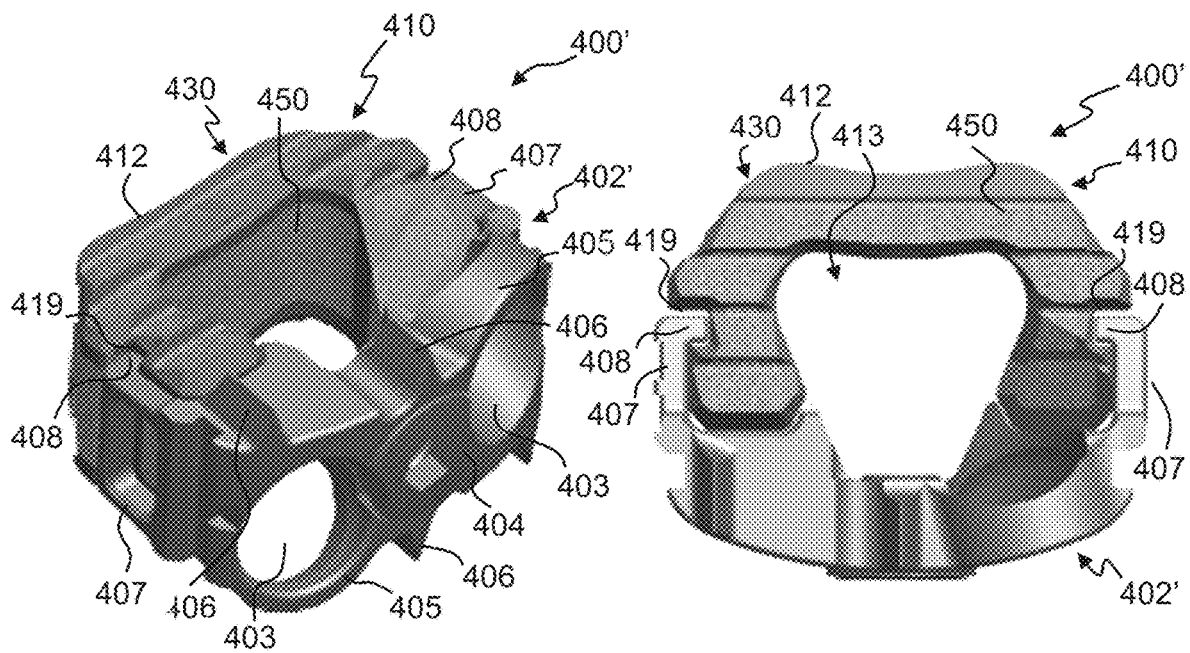
FIGS. 78 and 79 are perspective and top views, respectively, of an intervertebral implant according to another embodiment of the disclosure with the porous portions shown textured.
Figures 80, 81:
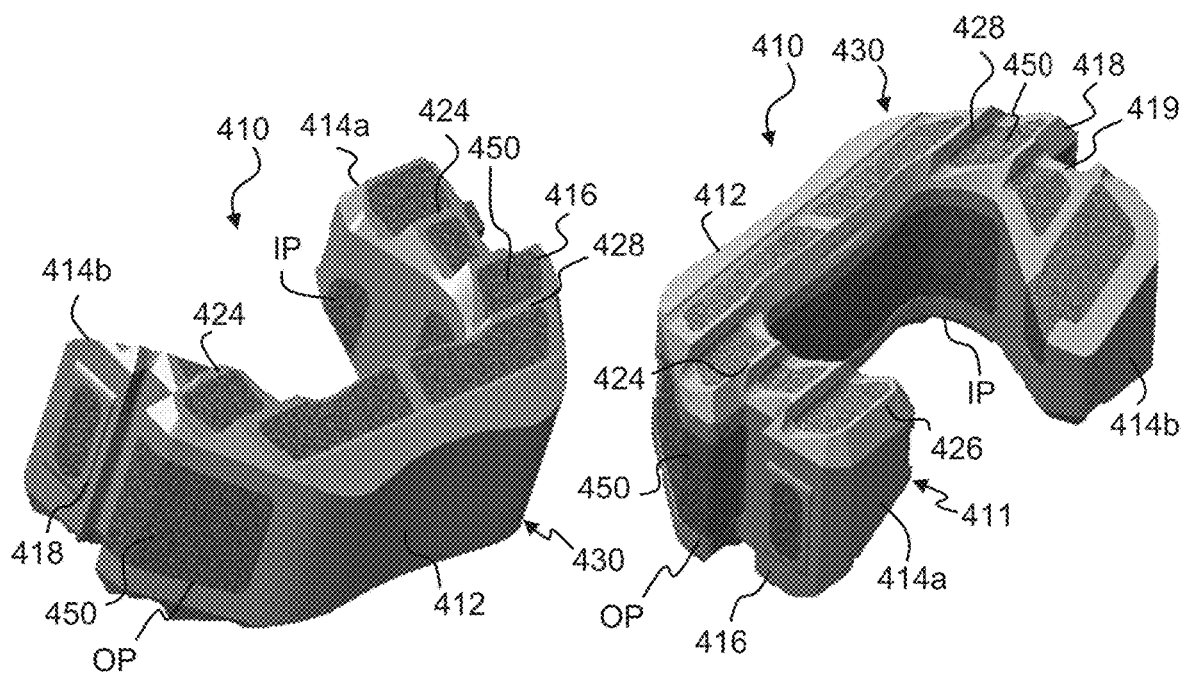
FIGS. 80-83 are front perspective, rear perspective, top and side views, respectively, of the spacer portion of the implants of FIGS. 76-79 with the porous portions shown textured.
Figures 82, 83:
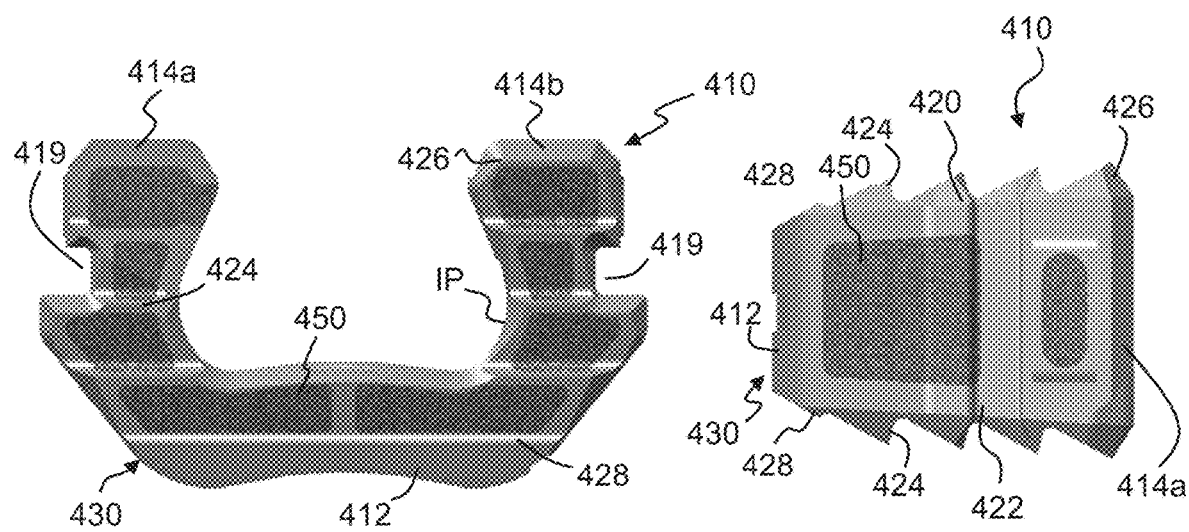

Referring now to FIGS. 70-72, an LLIF implant 310''' in accordance with another embodiment of the disclosure will be described. The implant 310''' is similar to the embodiment illustrated in FIGS. 65-67 except for slight modification in the structure of the support structure 330''' and a corresponding modification in the porous structure 350'''. Compared to the embodiment illustrated in FIGS. 65-67, the rims 332, 334, 336, 338 do not have cross struts extending therebetween. Additionally, external struts 366 are provided along the outside perimeter OP along each side wall 316''', 318''' and external struts 368 are provided along the inside perimeter IP along each side wall 316''', 318'''. Again, in the implant 310''', the open spaces are filled with the porous structure 350''' such that the porous structure 350''' encapsulates the struts 344 and extends from the upper surface 320 to the lower surface 322 and from the outer perimeter OP to the inner perimeter IP. The struts 366 are coplanar with the porous structure 350''' along the outer perimeter OP and the struts 368 are coplanar with the porous structure 350''' along the inner perimeter IP. In the illustrated embodiment, the porous structure 350''' substantially defines the inner perimeter IP and defines a substantial portion of the side walls 316''', 318''' along the outer perimeter OP.

Referring now to FIGS. 73-75, an LLIF implant 310$^{iv}$ in accordance with another embodiment of the disclosure will be described. The implant 310$^{iv}$ is similar to the previous embodiment except for slight modification in the structure of the support structure 330$^{iv}$ and a corresponding modification in the porous structure 350$^{iv}$. Compared to the previous embodiment, the rims 332, 334, 336, 338 have cross struts 331' extending therebetween but do not include X-shaped struts within the side walls 316$^{iv}$, 318$^{iv}$. Again, in the implant 310$^{iv}$, the open spaces are filled with the porous structure 350$^{iv}$ such that the porous structure 350$^{iv}$ extends from the upper surface 320 to the lower surface 322 and from the outer perimeter OP to the inner perimeter IP. The struts 366 are coplanar with the porous structure 350$^{iv}$ along the outer perimeter OP and the struts 368 are coplanar with the porous structure 350$^{iv}$ along the inner perimeter IP. In the illustrated embodiment, the porous structure 350$^{iv}$ substantially defines the inner perimeter IP and defines a substantial portion of the side walls 316$^{iv}$, 318$^{iv}$ along the outer perimeter OP.

Referring now to FIGS. 139-143, an LLIF implant 310$^{v}$ in accordance with another embodiment of the disclosure will be described. The implant 310$^{v}$ is similar to the embodiment illustrated in FIGS. 58-64 except for slight modification in the structure of the support structure 330$^{v}$ and a corresponding modification in the porous structure 350$^{v}$. In the present embodiment, the implant body 311' has a wedge configuration, tapering from a thickest height along the outer edge of the side wall 318$^{v}$ to a thinnest height along the outer edge of the side wall 316$^{v}$. The front wall 340'' and rear wall 335'' are correspondingly tapered. Additionally, the serration 328'' along the front wall 340'' does not include micro serrations. As in the embodiment illustrated in FIGS. 58-64, the rims 332, 334, 336, 338 have cross struts 331 extending therebetween, but do not include X-shaped struts within the side walls 316$^{v}$, 318$^{v}$. Instead, each side wall 316$^{v}$, 318$^{v}$ has a single linear strut 369 extending perpendicularly between the upper outer rim 332 and the lower outer rim 336 at an approximate mid-point of the side wall 316$^{v}$, 318$^{v}$. Again, in the implant 310$^{v}$, the open spaces are filled with the porous structure 350$^{v}$ such that the porous structure 350$^{v}$ extends from the upper surface 320 to the lower surface 322 and from the outer perimeter OP to the inner perimeter IP. The struts 369 are coplanar with the porous structure 350$^{v}$ along the outer perimeter OP. In the illustrated embodiment, the porous structure 350$^{v}$ substantially defines the inner perimeter IP and defines a substantial portion of the side walls 316$^{v}$, 318$^{v}$ along the outer perimeter OP.

Referring now to FIGS. 144-147, an LLIF implant 310$^{vi}$ in accordance with another embodiment of the disclosure will be described. The implant 310$^{vi}$ is similar to the embodiment illustrated in FIGS. 139-143 except for slight modification in the structure of the support structure 330$^{v}$ and a corresponding modification in the porous structure 350$^{vi}$. As in the previous embodiment, the implant body 311'' of the present embodiment has a wedge configuration, tapering from a thickest height along the outer edge of the side wall 318$^{vi}$ to a thinnest height along the outer edge of the side wall 316$^{v'}$. The front wall 340''' and rear wall 335''' are correspondingly tapered. In the present embodiment, the serrations 328'' along the front wall 340''' and the serrations 326 along the rear wall 335''' include micro serrations.

As in the previous embodiment illustrated, the rims 332, 334, 336, 338 have cross struts 331 extending therebetween, but do not include X-shaped struts within the side walls 316$^{vi}$, 318$^{vi}$. Furthermore, the side walls 316$^{vi}$, 318$^{vi}$ do not include the linear struts of the previous embodiment, but instead, the rims 332, 334, 336, 338 are only interconnected at the front wall 340''' and the rear wall 335'''. As seen in the figures, contoured portions 333 extend forwardly and rearwardly from each of the cross struts 331 along the upper rims 332, 334 and the lower rims 336, 338. The cross struts 331 along with contoured portions 333 of the rims 332, 334, 336, 338 define the contour of the serrations 324'.

Again, in the implant 310$^{vi}$, the open spaces are filled with the porous structure 350$^{vi}$ such that the porous structure 350$^{vi}$ extends from the upper surface 320 to the lower surface 322 and from the outer perimeter OP to the inner perimeter IP. In the illustrated embodiment, the porous structure 350$^{vi}$ substantially defines the inner perimeter IP and defines a substantial portion of the side walls 316$^{vi}$, 318$^{vi}$ along the outer perimeter OP. The porous structure 350$vi$ also follows the contoured portions 333 in defining the shape of each of the serrations 324'.

Referring now to FIGS. 76-86, embodiments of two-piece cervical implants 400, 400' will be described. Each of the implants 400, 400' includes a plate 402, 402' and connectable spacer 410. Each of the plates 402, 402' defines bone screw holes 403 and one or more blocking set screws 404. The plates 402, 402' may have varying configurations with tabs 405 and projections 406. The plate configurations are not limited to those shown. Each of the plates 402, 402' includes arms 407 with inward projections 408 which engage in slots 419 in the spacer 410 to connect the spacer 410 with the respective plate 402, 402'. The illustrated plates 402, 402' are solid structures and do not include porous structure, however, the plates may be made with portions having a porous structure.

Referring to FIGS. 80-86, the spacer 410 has body 411 with a generally U-shaped configuration. The body 411 is defined by a tapered front end 412 with side walls 416 and 418 extending to free ends 414$a$, 414$b$. The spacer 410 has an outer perimeter OP extending about the body 411 and an inner perimeter IP within the U-shape of the body 411. When the spacer 410 is connected with a plate 402, 402', a hollow interior chamber 413 is defined which is configured to receive bone growth promoting materials. The spacer 410 has an upper surface 420 and a substantially parallel lower surface 422, with both surfaces having a tapering portion 423 at the front end 412. The upper and lower surfaces 420, 422 define a plurality of serrations 424 along the side walls 416, 418, a serration 428 along the front end 412 and serrations 426 at the free ends 414$a$, 414$b$. Each side wall 416, 418 defines a connection slot 419 forward of the respective free end 414$a$, 414$b$. The slots 419 are engaged by the projections 408 on the plate arms 407 to attach the spacer 410 to the respective plate 402, 402'. The spacer 410 is defined by a solid support structure 430 with an interfiled, integral porous structure 450.

Figure 84:
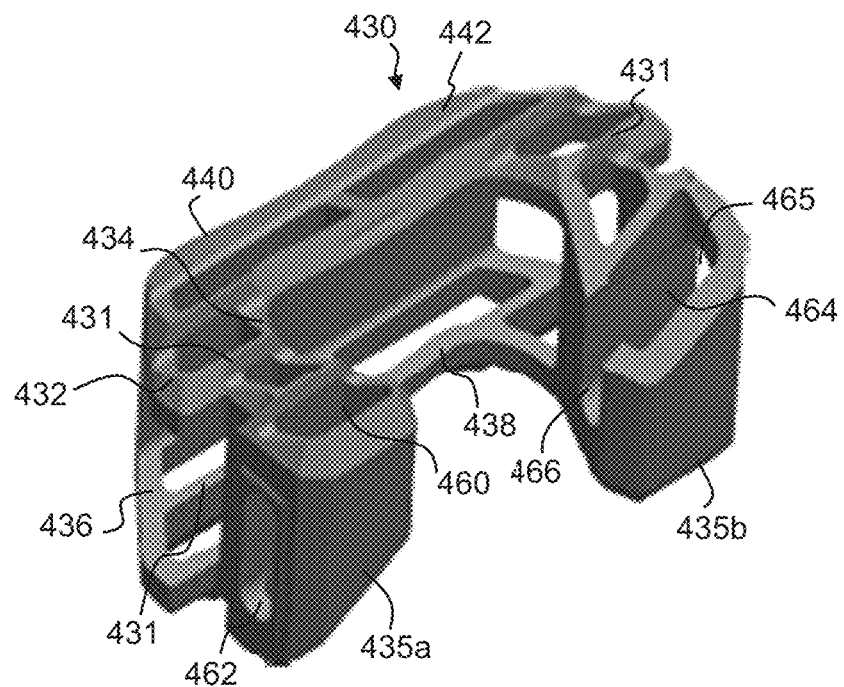
FIGS. 84-86 are perspective, top and side views, respectively, of the spacer portion of FIGS. 80-83 with the porous portions removed to show the support structure.
Figure 85:
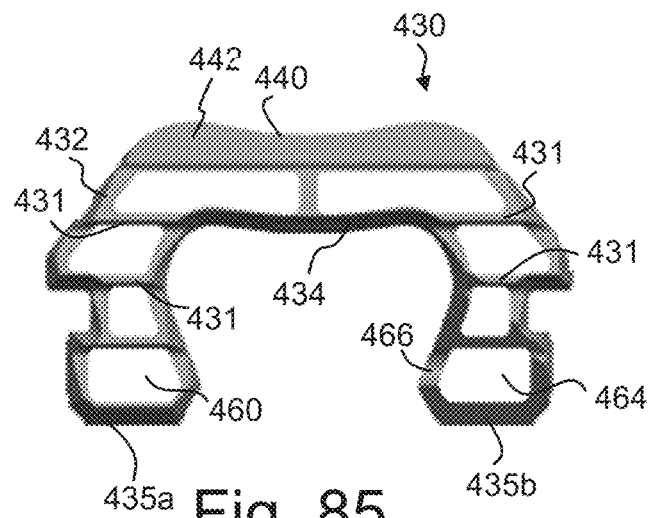
Figure 86:
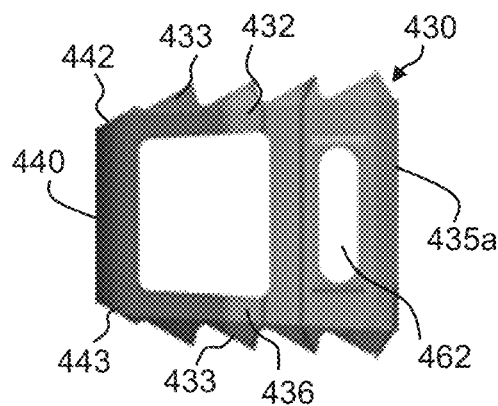

Referring to FIGS. 84-86, the solid support structure 430 includes an outer rim 432 extending about the outer perimeter OP of the upper surface 420 and an inner rim 434 extending about the inner perimeter IP of the upper surface 420. Similarly, an outer rim 436 extends about the outer perimeter OP of the lower surface 422 and an inner rim 438 extends about the inner perimeter IP of the lower surface 422. A plurality of cross struts 431 extend between the outer rims 432, 436 and the respective inner rims 434, 438 along the side wall areas. As seen in the figures, the cross struts 431 along with contoured portions 433 of the rims 432, 434, 436, 438 define the contour of the serrations 424.

A solid front wall 440 interconnects the outer rims 432, 436 along the front end area. The front wall 440 includes an upper sloped portion 442 and a lower sloped portion 443. While the rims and walls are described as specific elements for clarity, it is understood that the elements are formed as a unitary structure and may be formed as a smooth structure without any distinction between the elements. A portion of the front wall 440 defines the serration 428. A rear wall structure 435a, 435b at each free end 414a, 414b additionally interconnects the outer rims 432, 436 and the respective inner rims 434, 438 along the rear end area as well as further connecting the upper and lower structures together. The rear wall structure 435a extends about an open area 460 with a side opening 462 and rear wall structure 435b extends about an open area 464 with opposed side openings 465, 466.

In the illustrations of the support structure 430 in FIGS. 84-86, it is seen that there is significant open space between the upper rims 432, 434 and the lower rims 436, 438, between the inside surface of the front wall 440 and the inner rims 434, 438 and within the open areas 460, 462. As illustrated in FIGS. 80-83, in the spacer 410, the open spaces are filled with the porous structure 450 such that it extends from the upper surface 420 to the lower surface 422 and from the outer perimeter OP to the inner perimeter IP. In the illustrated embodiment, the porous structure 450 substantially defines the inner perimeter IP and defines a substantial portion of the side walls 416, 418 along the outer perimeter OP.

Referring now to FIGS. 164-169, a spacer 410' in accordance with another embodiment of the disclosure will be described. The spacer 410' is similar to the previous embodiment except for slight modification in the structure of the support structure 430' and a corresponding modification in the porous structure 450'. In the present embodiment, a lateral window 470 is defined through each of the side walls 416', 418'. The lateral windows 470 may, for example, aid in assessing bony fusion in post-operative X-ray images. In the present embodiment, each lateral window 470 includes a respective solid window frame 471, however, it is understood that the lateral windows may be defined in the side walls 416', 418' by the porous structure 450' only without any solid frame or the like.

In the present embodiment, each of the illustrative solid frames 471 includes an outer frame ring 472. Each frame ring 472 has a width approximately equal to the width of the outer rims 432, 436, however, the width may be different therefrom. For example, the width may be such that the frame 471 extends from the outer perimeter OP to the inner perimeter IP. As another alternative, the solid frames 471 may include inner and outer rings with cross struts extending therebetween. The rear ends of the outer rings 472 each connect with the rear wall 435 to cantileverly support each of the solid frames 471.

As in the previous embodiments, all of the open spaces of the spacer 410' are filled with the porous structure 450'' such that it extends from the upper surface 420 to the lower surface 422. The porous structure 450'' will still substantially define the inner perimeter IP and will define a substantial portion of the side walls 416'', 418', with the lateral windows 470 extending therethrough.

Referring now to FIGS. 89-96, an embodiment of an articulating TLIF implant 510 will be described. As illustrated, the implant 510 has a body 511 with a generally arcuate shape. The body 511 is defined by a tapered front end 512, a rectangular rear end 514 and arcuate side walls 516 and 518 extending therebetween. The implant 510 has an outer perimeter OP extending about the body 511. A hollow interior chamber 513 is defined within an inner perimeter IP of the body 511. The hollow interior chamber 513 is configured to receive bone growth promoting materials. The implant 510 has an upper surface 520 and a substantially parallel lower surface 522, with both surfaces having a tapering portion 523 at the front end 512. The upper and lower surfaces 520, 522 define a plurality of serrations 524 along the side walls 516, 518 and a plurality of serrations 526 along the rear end 514. The rear end 514 of the implant 510 includes a hole 525 through one of the surfaces 522 and a slot 527 in communication therewith. An articulating member 570 is positioned within the hole 525 and slot 527 and is pivotal relative to the body 511. The articulating member 570 includes a body 572 received in and rotatable within the hole 525. A threaded tool receiving opening 574 extends from the body 572 and is aligned within the slot 527. A threaded implant tool is received in the threaded tool receiving opening 574 and may be utilized for implanting and articulating the position of the implant 510 in a known manner. The articulating member 570 may be manufactured during the 3D manufacturing process of the body 511 or may be manufactured separately and thereafter positioned within the body 511. The implant 510 is defined by a solid support structure 530 with an interfiled, integral porous structure 550.

The solid support structure 530 includes an outer rim 532 extending about the outer perimeter OP of the upper surface 520 and an inner rim 534 extending about the inner perimeter IP of the upper surface 520, i.e. about the interior chamber 513. Similarly, an outer rim 536 extends about the outer perimeter OP of the lower surface 522 and an inner rim 538 extends about the inner perimeter IP of the lower surface 522. A plurality of cross struts 531 extend between the outer rims 532, 536 and the respective inner rims 534, 538 along the side wall areas. As seen in the figures, the cross struts 531 along with contoured portions 533 of the rims 532, 534, 536, 538 define the contour of the serrations 524. In addition to interconnecting the rims within a given upper or lower surface, external linear struts 560, 562 additionally interconnect the rims 532, 534, 536, 538. An outer linear strut 560 extends along each of the side walls 516, 518 along the outer perimeter OP. The outer linear struts 560 extend substantially perpendicular to the upper and lower rims at an approximate midpoint of the respective wall. An inner linear strut 562 extends along each of the side walls 516, 518 along the inner perimeter IP. The inner linear struts 562 extend substantially perpendicular to the upper and lower rims at an approximate midpoint of the respective wall.

The solid rear wall 535 additionally interconnects the outer rims 532, 536 and the respective inner rims 534, 538 along the rear end area as well as further connecting the upper and lower structures together. The solid rear wall 535 defines the hole 525 and slots 527. Recessed areas 539 and 541 on the upper and lower sides of the rear wall 535 extend between the cross struts 537 and define the serrations 526, however, in the present embodiment, these recesses generally do not receive porous structure, as seen in FIGS. 89-92. It is understood that these recesses could receive porous structure as in previous embodiments. The solid front wall 540 also interconnects the outer rims 532, 536 and the respective inner rims 534, 538 along the front end area. The front wall 540 includes an upper sloped portion 542 extending between the upper outer rim 532 and inner rim 534 and a lower sloped portion 543 extending between the lower outer rim 536 and inner rim 538. While the rims and walls are described as specific elements for clarity, it is understood that the elements are formed as a unitary structure and may be formed as a smooth structure without any distinction between the elements.

In the illustrations of the support structure 530 in FIGS. 93-96, it is seen that there is significant open space between the upper rims 532, 534 and the lower rims 536, 538 and between the inside surface of the front wall 540 and the inner rims 534, 538. As illustrated in FIGS. 89-92, in the implant 510, the open spaces are filled with the porous structure 550 such that it extends from the upper surface 520 to the lower surface 522 and from the outer perimeter OP to the inner perimeter IP. In the present embodiment, the struts 560, 562 are not encapsulated in the porous structure 550, but instead the struts 560 are coplanar with the porous structure 550 along the outer perimeter OP and the struts 562 are coplanar with the porous structure 550 along the inner perimeter IP. Again, the porous structure 550 substantially defines the inner perimeter IP and defines a substantial portion of the side walls 516, 518 along the outer perimeter OP.

Figure 97:
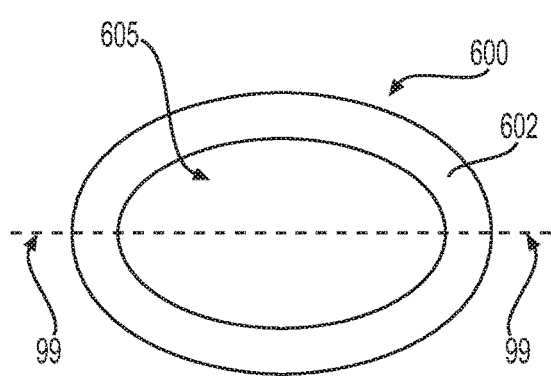
FIGS. 97 and 98 are top and side views, respectively, of an intervertebral implant according to another embodiment of the disclosure
Figure 98:
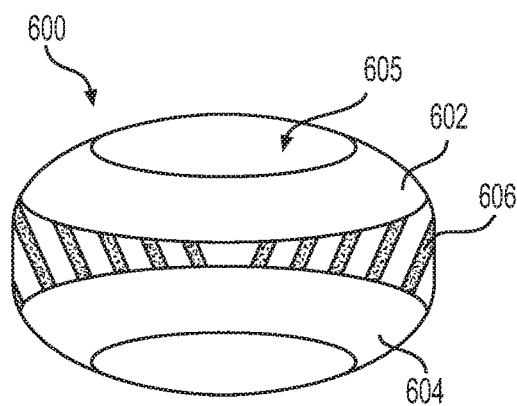
Figure 99:
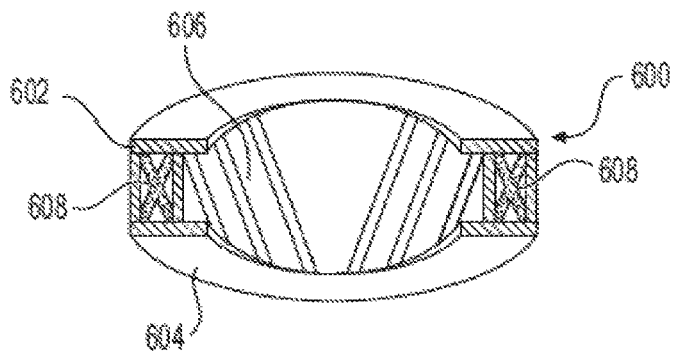
FIG. 99 is a cross-sectional view along the line 99-99 in FIG. 97.

Referring to FIGS. 97-99, another embodiment of an intervertebral implant 600 will be described. The implant 600 includes an upper plate 602 and a lower plate 604 supported by a plurality of solid struts 606, 608 extending therebetween. An open graft window 605 is defined within the implant 600. The struts 606, 608 are configured to provide desired load bearing properties of the implant 600. The end plates 602, 604 may be formed as a porous structure, for example, having a trabecular porosity. In addition to the porosity, the surfaces of the end plates 602, 604 may have a nanoscale roughness formed thereon. As seen in FIG. 98, in the illustrated embodiment, the end plates 602, 604 and the struts 606, 608 are configured such that the implant 600 has a biconvex superior and inferior geometry.

Figure 100:
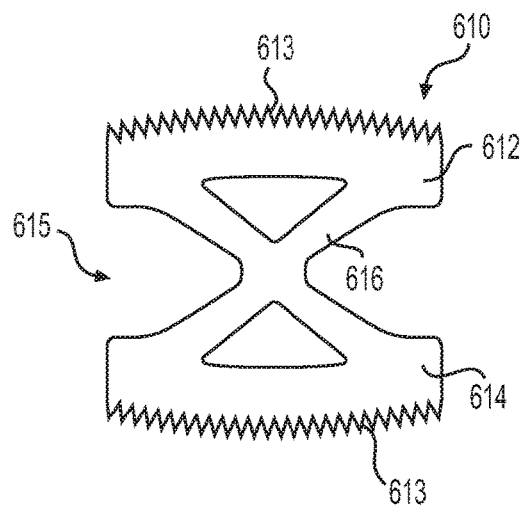
FIGS. 100 and 101 are side views of an intervertebral implant according to another embodiment of the disclosure, with FIG. 101 illustrating an insertion tool extending through the implant.
Figure 101:
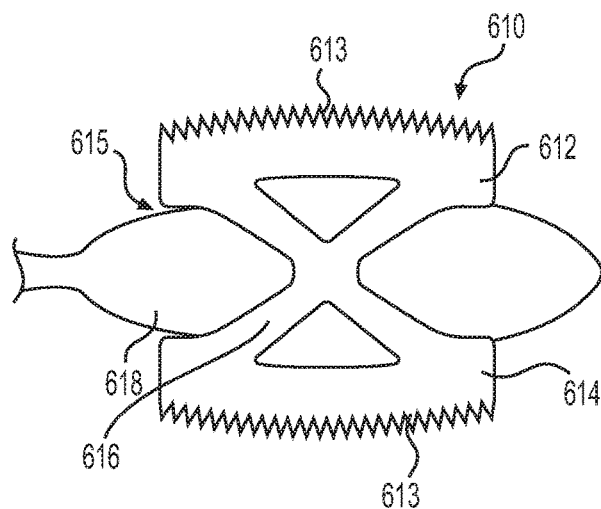
Figure 102:
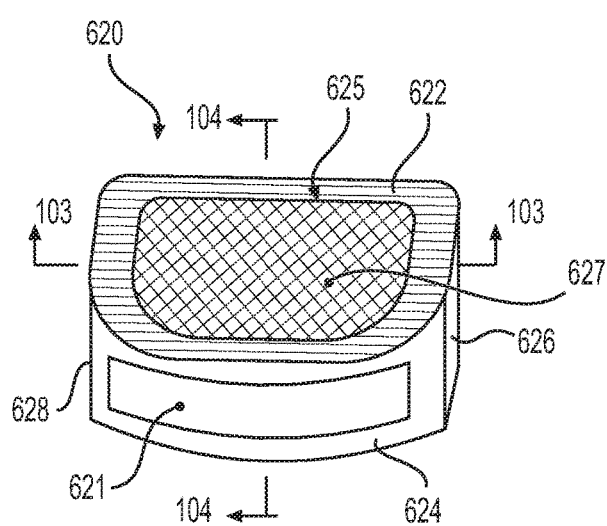
FIG. 102 is a perspective view of an intervertebral implant according to another embodiment of the disclosure, FIG.
Figure 103:
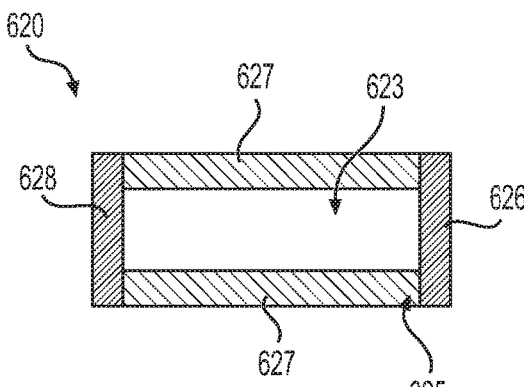
Figure 104:
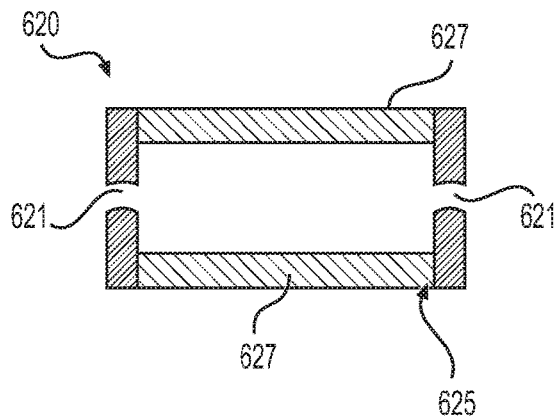
FIG. 104 is a cross-sectional view along the line 104-104 in FIG. 102.
Figure 110:
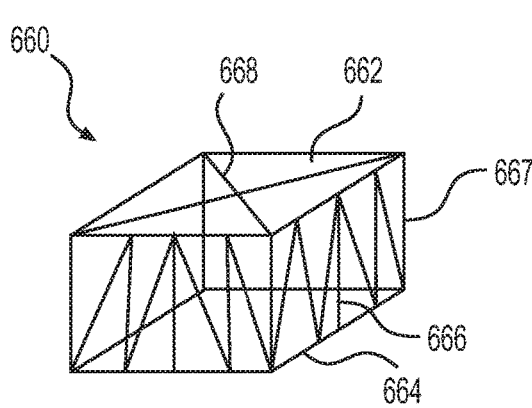
FIGS. 110-112 are perspective, side and top views, respectively, of an intervertebral implant according to another embodiment of the disclosure
Figure 111:
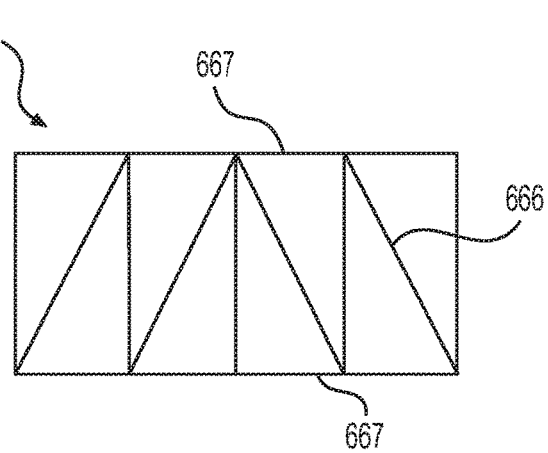
Figure 112:
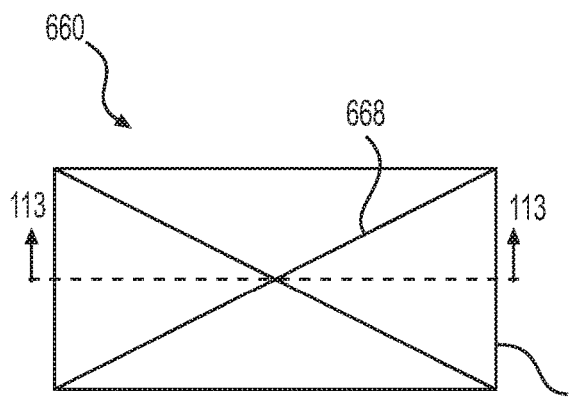
Figure 113:
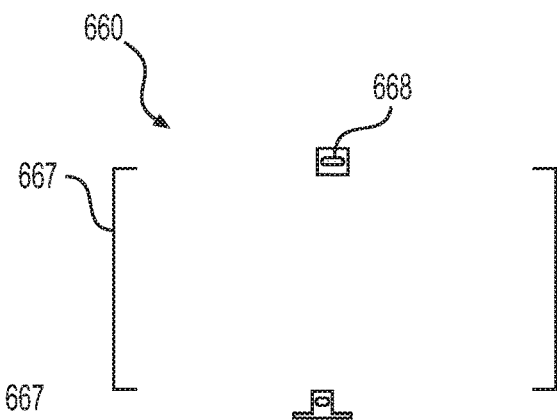
FIG. 113 is a cross-sectional view along the line 113-113 in FIG. 112.

Referring to FIGS. 100 and 101, another embodiment of an intervertebral implant 610 will be described. The implant 610 includes an upper plate 612 and a lower plate 614 supported by X-shaped struts 616 extending between the plates 612, 614 on each lateral side of the implant 610. An open graft window 615 is defined within the implant 610 between the plates 612, 614. As shown in FIG. 101, the window 615 may be configured to receive an insertion tool 618. The end plates 602, 604 and struts 616 may be formed as a porous structure. Alternatively, the struts 616 may be formed as a solid structure. In addition to the porosity, the surfaces of the end plates 612, 614 may have a roughness 613 formed thereon.

Referring to FIGS. 102-106, another embodiment of an intervertebral implant 620 will be described. The implant 620 includes an upper plate 622 and a lower plate 624 supported by opposed solid walls 626, 628 extending therebetween. Anterior and/or lateral windows 621 open into an interior chamber 623 configured to receive graft material. Each of the upper and lower plates 622, 624 has a central open area 625 wherein a porous webbing surface 627 is formed. FIGS. 105 and 106 illustrate examples of a porous webbing surface 627. The webbing may be formed with a grid or honeycomb pattern which is porous to bone ingrowth. The webbing may also be configured such that is may appear opaque when turned past a critical angle. Such a feature may be used for assessing the implants orientation or position.

Referring to FIGS. 107 and 108, intervertebral implants 630, 640 illustrating various features will be described. The implant 630 of FIG. 107 includes a body 632 with an upper surface 634 and a lower surface 636. One or both of the surfaces 634, 636 may be formed with a complex configuration to optimize end plate contact. For example, the upper surface 634 has a biconcave configuration. Similarly, the implant 640 of FIG. 108 includes a body 642 with an upper surface 644 and a lower surface 646. One or both of the surfaces 644, 646 may be formed with various teeth or surface roughness features to minimize subsidence or migration. For example, the upper surface 646 has a plurality of teeth 648 defined thereon. For each of the implants 630, 640, the body 632, 642 may include both solid structure and porous structure as described herein.

Referring to FIG. 109, another embodiment of an intervertebral implant 650 will be described. The implant 650 includes an upper plate 652 and a lower plate 654 supported by a plurality of solid struts 656 extending therebetween. The density of the struts 656 increases moving posteriorly to provide a varying A-P stiffness to the implant, for example, to optimize the load of an anterior graft.

Figure 114:
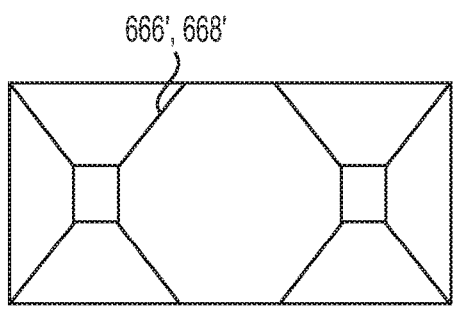
FIGS. 114 and 115 illustrate alternative strut patterns of an illustrative support structure.
Figure 115:
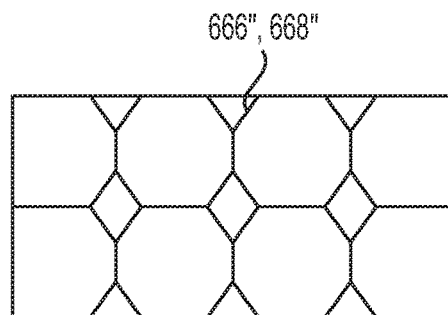

Referring to FIGS. 110-113, another embodiment of an intervertebral implant 660 will be described. The implant 660 includes an upper surface 662 and a lower surface 664 supported by a plurality of solid struts 666 extending therebetween. The upper and lower surfaces 662, 664 are defined by perimeter struts 667 and diagonal struts 668. As illustrated, the struts 666, 667, 668 that make up the support structure extend generally along the supporting edges while the remainder of the implant structure remains open for either porous structure or ingrowth chambers. FIGS. 114 and 115 illustrate alternative strut configurations for either the side walls or top or bottom surfaces of the implant 650. In the embodiment illustrated in FIG. 114, the struts 666', 668' have a rectangular central region with radial supports extending from the corners thereof. In the embodiment illustrated in FIG. 115, the struts 666", 668" have a diamond shaped central region with octagon patterned struts thereabout.

Figure 116:
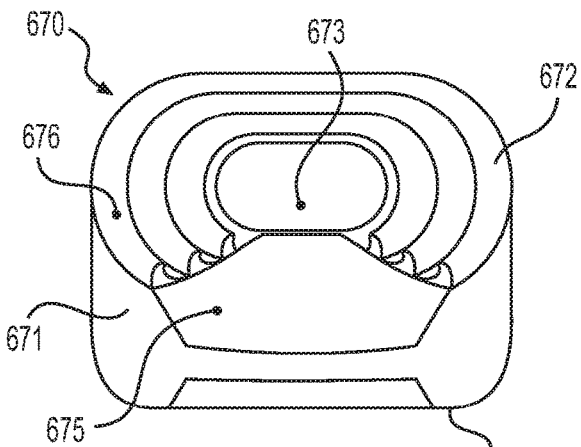
FIG. 116 is a perspective view of an intervertebral implant according to another embodiment of the disclosure.

Referring to FIG. 116, another embodiment of an intervertebral implant 670 will be described. The implant 670 includes a body 671 with an upper surface 672 and a lower surface 672 extending about an opening 613 into an ingrowth cavity. The front end of the implant 670 includes sloped surfaces 675 to define a smooth leading edge. One or both of the surfaces 672, 672 may include a radial sawtooth configuration 676. As in previous embodiments, the body 671 may include both solid structure and porous structure as described herein.

Figure 117:
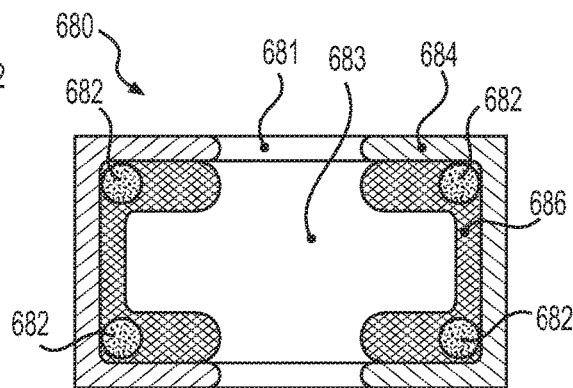
FIG. 117 is a cross-sectional view of an intervertebral implant according to another embodiment of the disclosure.

Referring to FIG. 117, another embodiment of an intervertebral implant 680 will be described. The implant 680 includes a solid support frame 682 encased within porous structure 684, 686. The implant 680 defines at least one opening 681 into an ingrowth chamber 683. In the illustrated embodiment, the porous structure includes areas of different densities. In the illustrated embodiment, the outer porous structure 684 has a lower density than the inner porous structure 686. As described herein, the various implants may be formed with porous structures having varying densities, not just with respect to outer and inner layers, but also within a given layer at different areas of the implant, e.g. anterior versus posterior.

Figure 118:
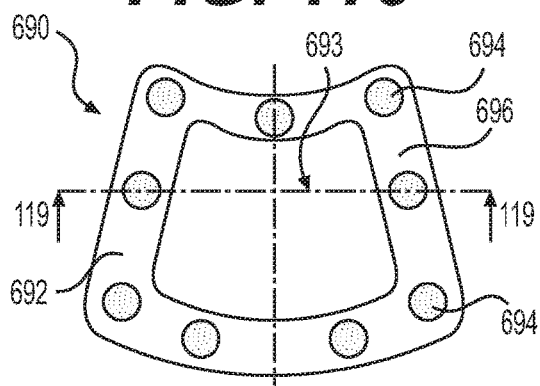
FIG. 118 is a top view of an intervertebral implant according to another embodiment of the disclosure and FIG. 119 is a cross-sectional view along the line 119-119 in FIG. 118.
Figure 119:
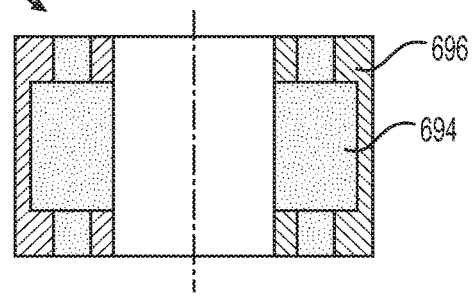

Referring to FIGS. 118 and 119, another embodiment of an intervertebral implant 690 will be described. The implant 690 includes a body 692 extending about an ingrowth chamber 693. The body 692 is defined by a porous portion 696 surrounding a plurality of support struts 694. The support struts 694 are not interconnected to one another. The support struts 694 may be a solid structure or may be a porous structure with a greater density than the porous portion 696. For example, the struts 694 may be a porous structure having a cancellous density while the porous structure 696 has a cortical density. Since the body 692 includes a significant porous structure, the ingrowth chamber 693 may be smaller than compared to an implant having a non-porous body.

Figure 120:
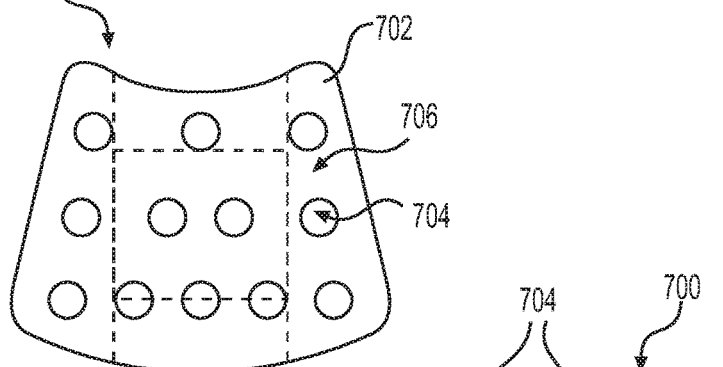
FIGS. 120 and 121 are top and rear views, respectively, of an intervertebral implant according to another embodiment of the disclosure
Figure 122:
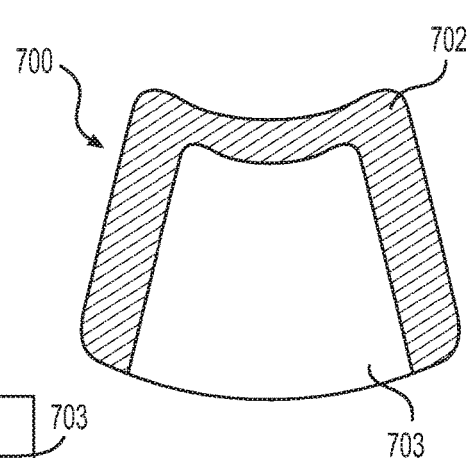
FIG. 122 is a cross-sectional view along the line 122-122 in FIG. 121.
Figure 121:
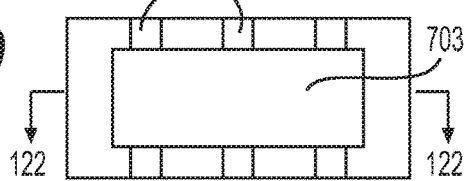

Referring to FIGS. 120-122, another embodiment of an intervertebral implant 700 will be described. The implant 700 includes a body 702 with an ingrowth pocket 703 extending into the posterior side thereof. The body 702 is defined by a porous portion 706 surrounding a plurality of support struts 704. The support struts 704 are not interconnected to one another. The support struts 704 may be a solid structure or may be a porous structure with a greater density than the porous portion 706. For example, the struts 704 may be a porous structure having a cancellous density while the porous structure 706 has a cortical density.

Figure 123:
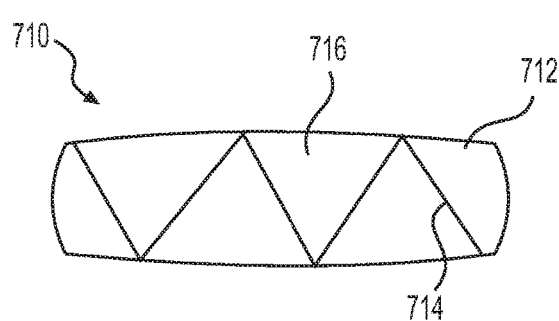
FIG. 123 is a side view of an intervertebral implant according to another embodiment of the disclosure.

Referring to FIG. 123, another embodiment of an intervertebral implant 710 will be described. The implant 710 includes a body 712. The body 712 is defined by an external area of higher density porous structure 714 surrounding a less dense porous structure 716. The higher density porous structure 714 acts as struts to provide the implant 710 strength. The area of higher density porous structure 714 is shown in a zig zag pattern, but may have other patterns and configurations.

Figure 124:
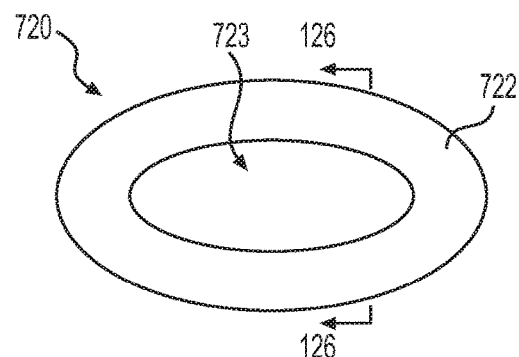
FIGS. 124 and 125 are top and side views, respectively, of an intervertebral implant according to another embodiment of the disclosure
Figure 125:
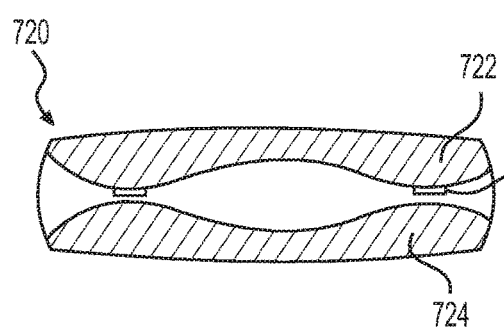
Figure 126:
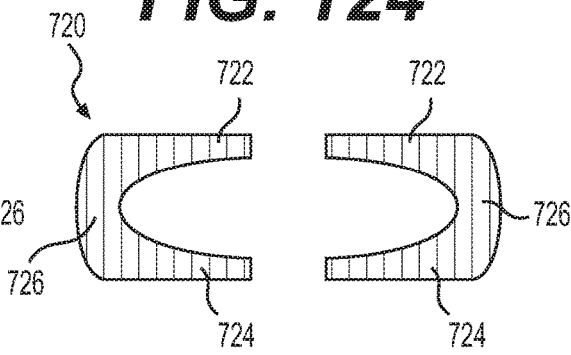
FIG. 126 is a cross-sectional view along the line 126-126 in FIG. 124.

Referring to FIGS. 124-126, another embodiment of an intervertebral implant 720 will be described. The implant 720 includes an upper plate 722 and a lower plate 724. Each of the plates 722 and 724 has a wave configuration with minimum struts 726 interconnecting the plates 722, 724. With such a configuration, the implant 720 has spring between the plates. An open graft window 723 is defined within the implant 720. The plates 722, 724 and the struts 726 may include both solid structure and porous structure, as described herein.

Figure 127:
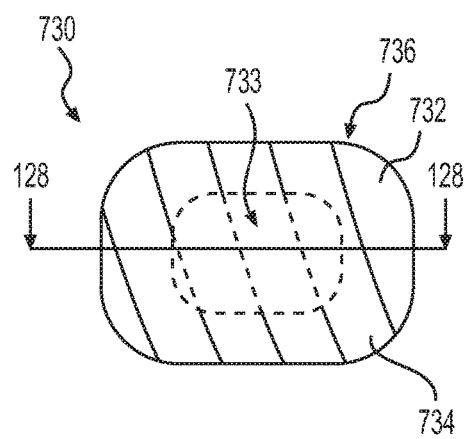
FIG. 127 is a side view of an intervertebral implant according to another embodiment of the disclosure and FIG. 128 is a cross-sectional view along the line 128-128 in FIG. 127.
Figure 128:
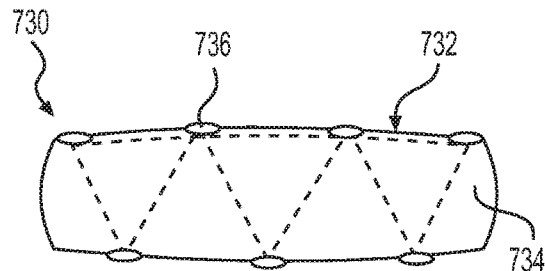

Referring to FIGS. 127 and 128, another embodiment of an intervertebral implant 730 will be described. The implant 730 includes a body 732 surrounding an ingrowth chamber 733. The body 732 is defined by a porous portion 734 which is surrounded a continuously wrapped support rib 736. The support rib 736 may be a solid structure or may be a porous structure with a greater density than the porous portion 734.

Referring to FIG. 129, another embodiment of an intervertebral implant 740 will be described. The implant 740 includes interconnectable body portions 742 and 744. In the illustrated embodiment, the upper body portion 742 includes a post 743 configured to friction fit within a hole 745 of the lower body portion 744. Various interconnectable upper and lower body portions 742, 744 may be printed and interconnected to form a customized implant 740. In the illustrated embodiment, three additional lower body portions 744', 744", 744''' and provided and all may be interconnected with the upper body portion 742 to achieve implants having different configurations.

Referring to FIGS. 130-132, another embodiment of an intervertebral implant 750 and a method of implantation thereof will be described. The implant 750 includes a central body 752 and a pair of expandable wings 753, 755. The implant 750 is connected to a hollow insertion tool 756 and moved within an intervertebral space 759. Once in position, graft material 757 is fed through the tool 756 and into the implant 750 whereby the wings 753, 755 are caused to expand. Graft material 757 is supplied until the area within the central body 752 and the expanded wings 753, 755 is filled. The packed graft material 757 maintains the expanded configuration of the implant 750.

Referring to FIGS. 133-135, another embodiment of an intervertebral implant 760 and a method of inserting such implant will be described. The implant 760 includes a body 762 extending about an ingrowth chamber 763. The body 762 is generally defined by a porous structure 764. Solid bore holes 766 are defined within the body 762 and are configured to receive screws or other anchors to facilitate fixation of the implant 760. The body 762 also defines a tool receiving opening 765. In the illustrated embodiment, an expandable tool 770 is inserted through the opening 765. The expandable tool 770 includes a pair of legs 772 with flanges 773 on the end thereof. In a collapsed condition, the flanges 773 pass through the opening 765. To engage the implant 760, a needle 775 or the like is extended between the legs 772, thereby forcing the flanges 773 outward such that the engaged the inside surface of the implant and do not pass through the opening 765 until the needle 775 is removed.

Referring to FIGS. 136 and 137, another tool and implant opening interconnection assembly will be described. In the present embodiment, the implant 780 has a tool receiving opening 782 with a wider central region 783 and narrower end regions 784. The insertion tool 790 has a head 792 with a complimentary configuration. The head 792 is positioned within the opening 782 with the orientation of the head 792 matching that of the opening 782 such that the head 792 passes through the opening 782. Once inside, the tool head 792 is rotated, for example, a quarter turn, such that the tool head 792 engages the inside surface of the implant 780 and is no longer removable through the opening 782. A securing sleeve 794 is threadably advanced along the tool 790 and engages the outside surface of the implant 780, securing the implant 780 between the tool head 792 and the sleeve 794.

Figure 138:
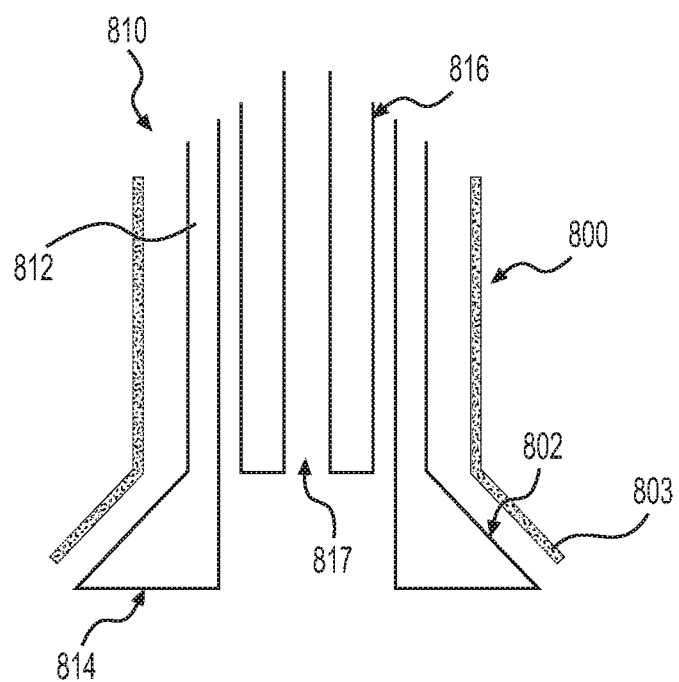
FIG. 138 is a schematic view of an example delivery tool in accordance with an embodiment of the disclosure.
Figure 139:
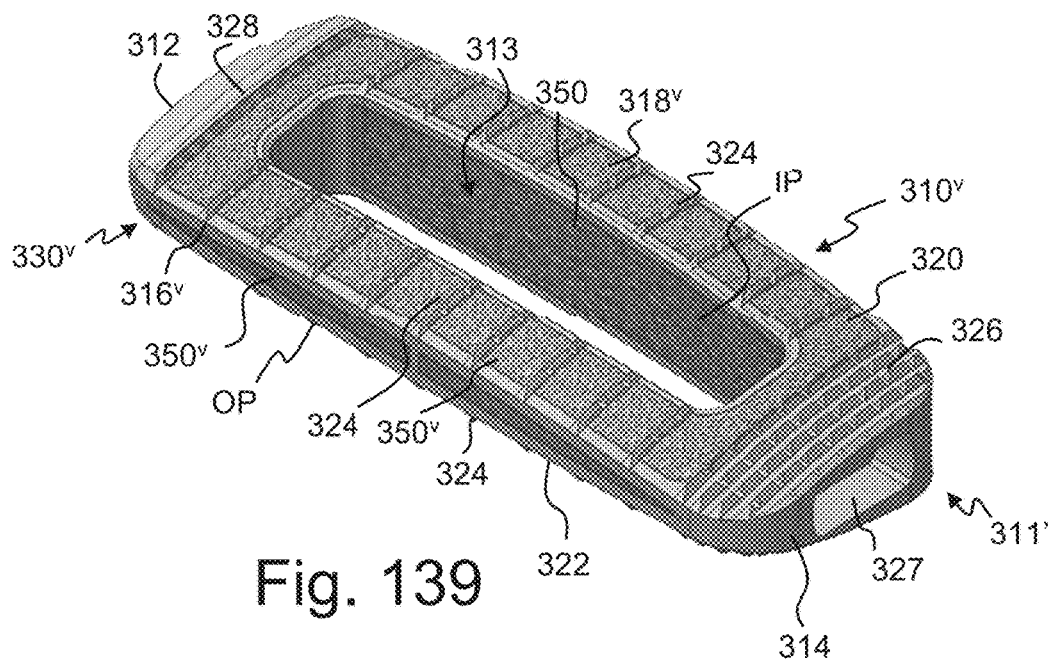
FIGS. 139-141 are perspective, top and side views, respectively, of an intervertebral implant according to another embodiment of the disclosure with the porous portions shown textured.
Figure 140:
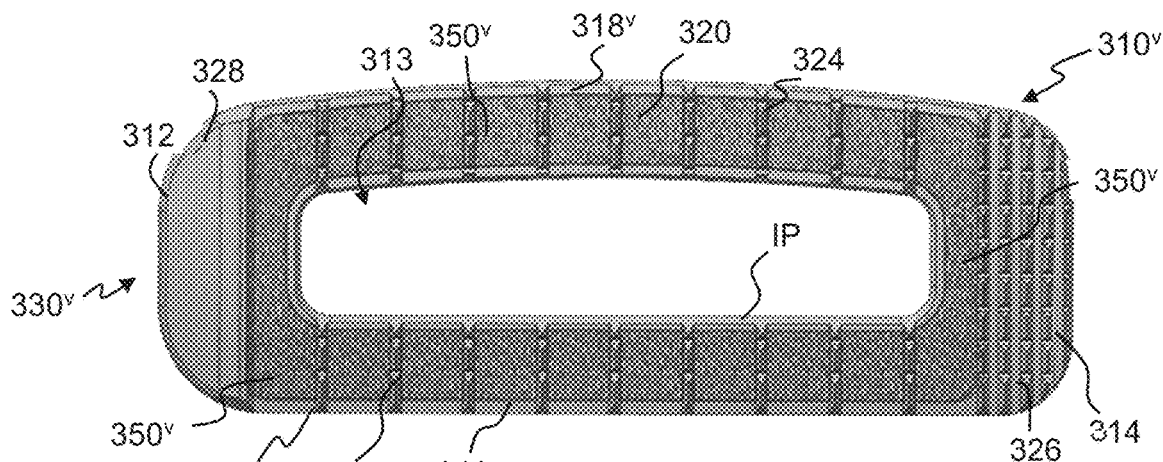
Figure 141:
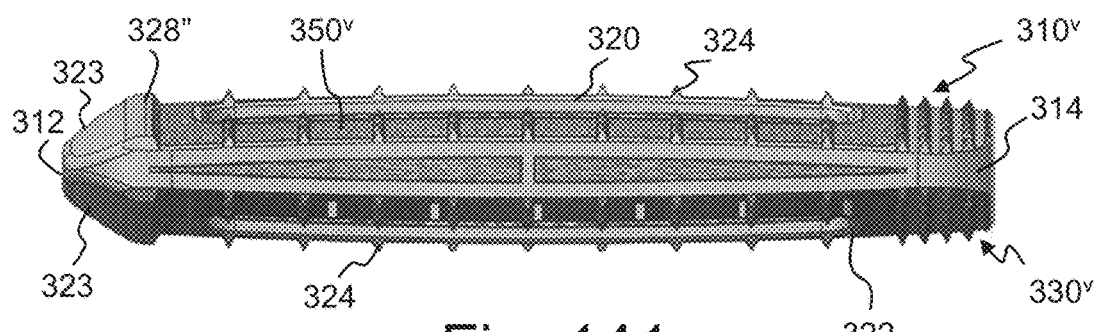
Figure 142:
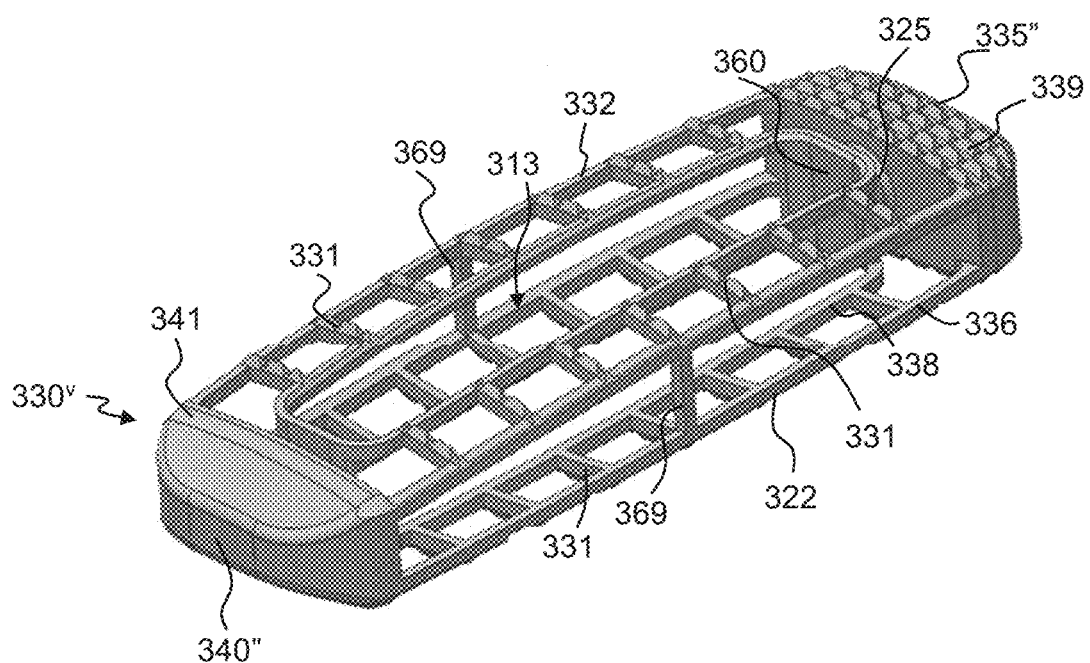
FIGS. 142 and 143 are perspective and top views, respectively, of the intervertebral implant of FIGS. 139-141 with the porous portions removed to show the support structure.
Figure 143:
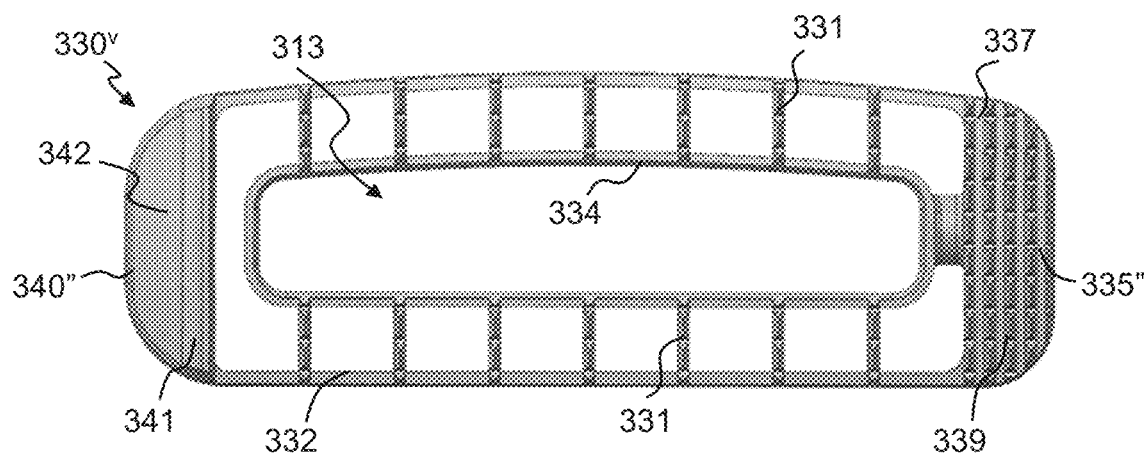
Figure 144:
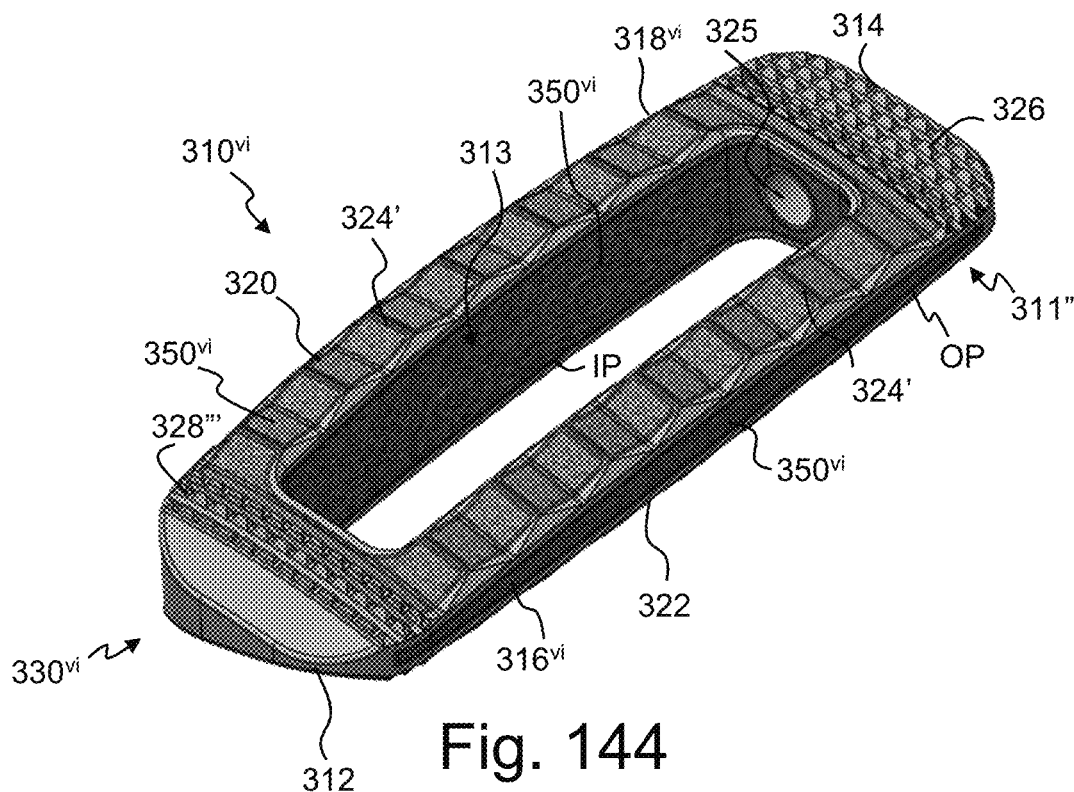
FIGS. 144 and 145 are perspective and top views, respectively, of an intervertebral implant according to another embodiment of the disclosure with the porous portions shown textured.
Figure 145:
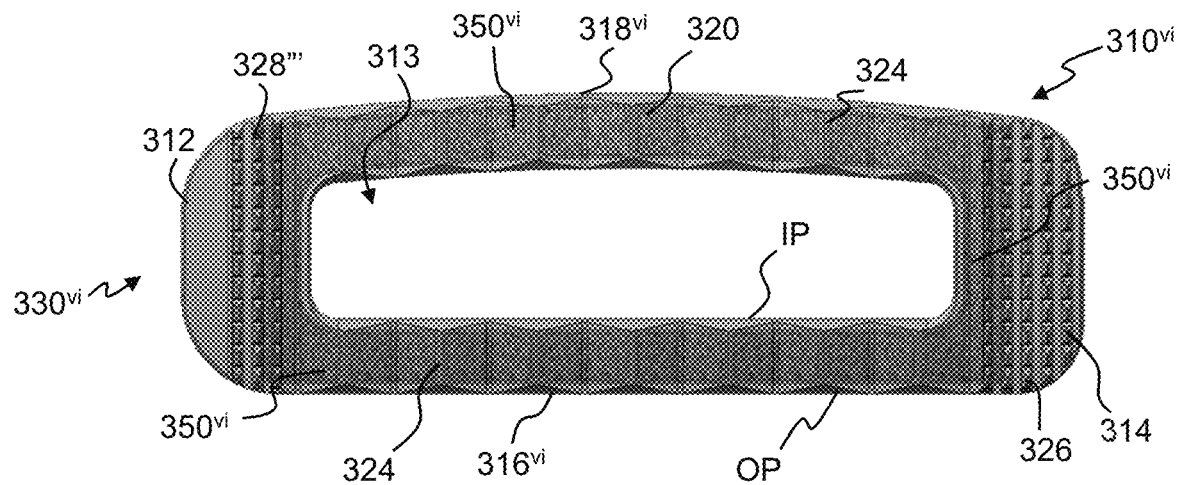
Figure 146:
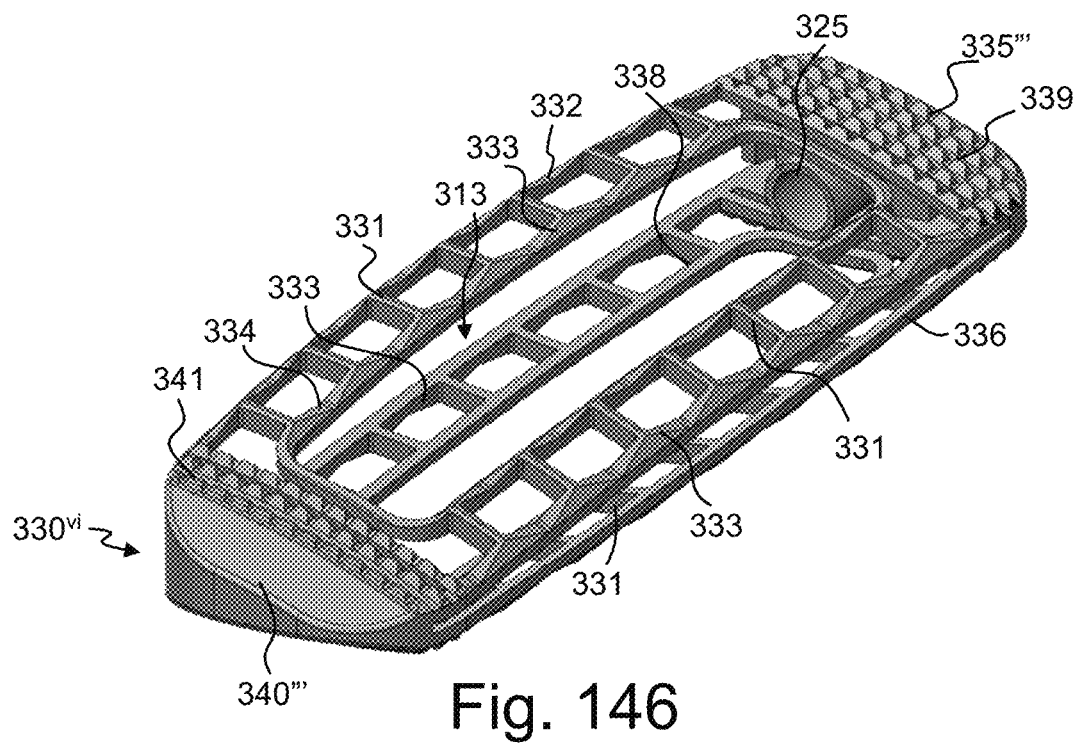
FIGS. 146 and 147 are perspective and top views, respectively, of the intervertebral implant of FIGS. 144 and 145 with the porous portions removed to show the support structure.
Figure 147:
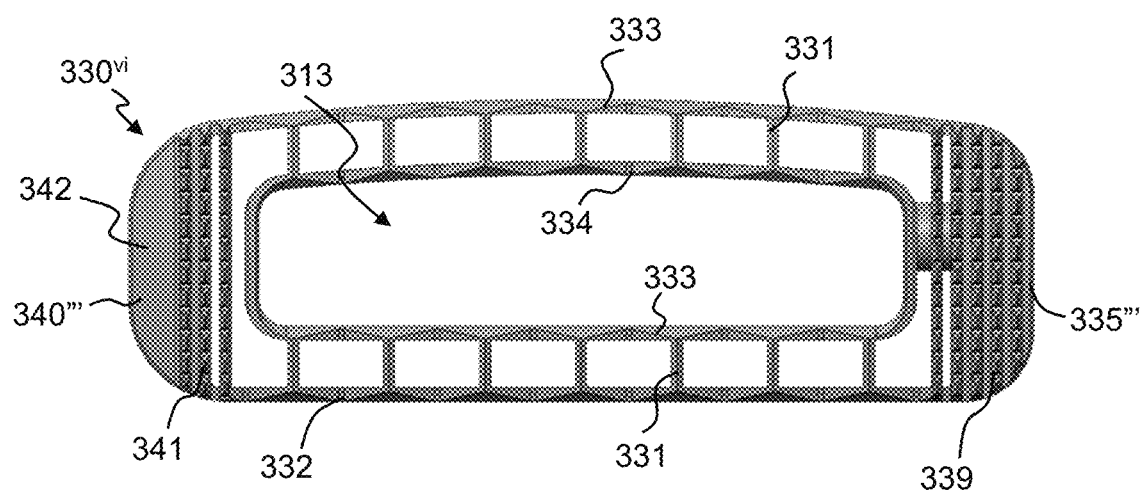

Referring to FIG. 138, another tool and implant opening interconnection assembly will be described. In the present embodiment, the implant 800 has a tool receiving opening 802 with an outward taper 803 at the inner side of the opening 802. The insertion tool 810 has an outer hollow tube 812 with a collet 814 on the free end thereof and an inner hollow tube 816 with a through passage 817. The inner hollow tube 816 is axially moveable relative to the outer hollow tube 812. Initially, the inner hollow tube 816 is withdrawn into the outer hollow tube 812 such that it is clear of the collet 814 such that the collet 814 may collapse and pass through the implant opening 802. Once the collet 814 passes through the opening 802, the inner hollow tube 816 is moved forward such that the collet 814 is expanded outward and maintained in the outward position, engaging the tapered portion 803 of the implant opening 802. Graft material or the like may be passed into the implant 800 through the through passage 817.

As described herein, the implants of the disclosure generally comprise a solid or higher density support structure and a porous structure formed integral therewith. The solid support structure may include solid front and rear walls interconnected by upper and lower implant surfaces. In several of the embodiments, the upper and lower surfaces include spaced apart rims with cross struts interconnecting the rims. In many embodiments, the solid support structure of the upper and lower surfaces includes a plurality of openings in which the integral porous structure is formed such that the porous structure extends along at least a portion of the upper and lower implant surfaces. The side walls extending between the front and rear walls generally have a minimal solid structure, for example, a plurality of struts extending between the upper and lower rims, but otherwise have open area therebetween in which the integral porous structure is formed. The configuration of the solid structure is selected to provide the implant sufficient structural integrity and mechanical stability while maximizing the area of porous structure which facilitates better integration/incorporation with the adjacent bone. In several embodiments of the disclosure, the solid structure generally encases the corners of the porous structure or otherwise houses the porous structure therein to maintain the structural integrity of the porous structure.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. An intervertebral implant for implantation in an intervertebral space between vertebrae, the implant comprising:
a body extending from an upper surface to a lower surface, the body having a front end, a rear end and a pair of spaced apart first and second side walls extending between the front and rear ends such that an internal chamber is defined within the front and rear ends and the first and second side walls, the body defining an outer perimeter and an inner perimeter extending about the internal chamber,
wherein at least one of the first and second side walls is defined by an integral porous structure extending from the upper surface to lower surface and from the outer perimeter to the inner perimeter, and at least one of the first and second side walls is free of any vertical solid support structure between the upper and lower surfaces, the integral porous structure having an average pore size of less than 800 μm in diameter.

2. The intervertebral implant of claim 1, wherein both of the first and second side walls are defined by the integral porous structure extending from the upper surface to lower surface and from the outer perimeter to the inner perimeter, and both of the first and second side walls are free of any vertical solid support structure between the upper and lower surfaces, the average porosity of the integral porous structure being greater than 50%.

3. The intervertebral implant of claim 1, wherein the first and second side walls include spaced apart solid upper rim members in the upper surface and spaced apart solid lower rim members in the lower surface, and a solid horizontal support structure includes at least one strut extending along the upper surface or the lower surface.

4. The intervertebral implant of claim 3, wherein the at least one strut includes one or more cross struts extending between the solid upper rim members and one or more cross struts extending between the solid lower rim members.

5. The intervertebral implant of claim 4, wherein each of the cross struts defines a portion of a surface serration or tooth configured to engage with adjacent vertebrae.

6. The intervertebral implant of claim 1, wherein a lateral window is defined through at least one of the first and second side walls and the porosity of the integral porous structure is greater than 60%.

7. The intervertebral implant of claim 6, wherein a solid support frame extends about the lateral window.

8. The intervertebral implant of claim 7, wherein the solid support frame includes at least one frame ring supported by a portion of a support structure defining a rear wall at the rear end.

9. The intervertebral implant of claim 1, wherein the lateral window is defined through at least one of the first and second side walls and wherein:
the integral porous structure has an average pore size of between 400 μm and 700 μm in diameter; and
the porosity of the integral porous structure is greater than 60%.

10. The intervertebral implant of claim 1, wherein the rear end is defined substantially by a solid wall.

11. The intervertebral implant of claim 1, wherein the rear end is defined in part by a solid wall and in part by the porous structure with portions of the porous structure defining a part of the rear end.

12. An intervertebral implant for implantation in an intervertebral space between vertebrae, the implant comprising:
a body having a front end, a rear end and opposed side walls extending between the ends, the body having an outer perimeter and an inner perimeter about an internal chamber, the body comprising:
an upper surface and a lower surface, the upper surface defined by a solid upper outer rim and a spaced apart solid upper inner rim and the lower surface defined by a solid lower outer rim and a spaced apart solid lower inner rim;
a solid front wall extending at the front end between at least the solid upper outer rim and the solid lower outer rim;
a solid rear wall extending at the rear end between at least the solid upper outer rim and the solid lower outer rim;
each of the side walls free of any solid struts extending between the upper and lower surfaces; and
a porous structure integrally formed with the solid upper rims, the solid lower rims, and the solid front and rear walls, the porous structure extending from the outer perimeter to the inner perimeter of the body and having an average pore size of less than 800 μm in diameter.

13. The intervertebral implant of claim 12, wherein one or more cross struts extend between the solid upper rims and one or more cross struts extend between the solid lower rims.

14. The intervertebral implant of claim 13, wherein each of the cross struts defines a portion of a surface serration or tooth configured to engage with adjacent vertebrae.

15. The intervertebral implant of claim 12, wherein a lateral window is defined through at least one of the side walls and the porosity of the integral porous structure is greater than 60%.

16. The intervertebral implant of claim 15, wherein a solid support frame extends about the lateral window.

17. The intervertebral implant of claim 16, wherein the solid support frame includes at least one frame ring supported by a portion of the solid rear wall.

18. The intervertebral implant of claim 12, wherein a lateral window is defined through at least one of the side walls and wherein:
- the integral porous structure has an average pore size of between 400 μm and 700 μm in diameter; and
- the porosity of the integral porous structure is greater than 60%.

19. A method of forming an intervertebral implant for implantation in an intervertebral space between vertebrae, the method comprising:
- forming an upper surface defined by a solid upper outer rim and a spaced apart solid upper inner rim;
- forming a lower surface defined by a solid lower outer rim and a spaced apart solid lower inner rim;
- forming a solid front wall extending at a front end between at least the solid upper outer rim and the solid lower outer rim;
- forming a solid rear wall extending at a rear end between at least the solid upper outer rim and the solid lower outer rim;
- forming side walls extending between the front and rear ends with each of the side walls free of any solid struts extending between the upper and lower surfaces; and
- integrally forming a porous structure with the solid upper rims, the solid lower rims and the solid front and rear walls, the porous structure extending from an outer perimeter of the implant to an inner perimeter extending about an internal chamber of the implant.

20. The method of claim 19, further comprising defining a lateral window through at least one of the side walls wherein the step of forming a porous structure includes forming by, thermal sintering, the porous structure having an average pore size of less than 800 μm in diameter and a porosity of greater than 60%.

\* \* \* \* \*